United States Patent
Gordon et al.

(10) Patent No.: US 6,743,903 B1
(45) Date of Patent: Jun. 1, 2004

(54) NUCLEIC ACIDS FOR THE DIAGNOSIS AND TREATMENT OF GIANT CELL ARTERITIS

(75) Inventors: Lynn K. Gordon, Tarzana, CA (US); Lee Goodglick, Los Angeles, CA (US); Melissa Goldman, Los Angeles, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 09/484,577

(22) Filed: Jan. 18, 2000

(51) Int. Cl.⁷ .................. C07H 21/04; C07H 15/09; C07H 15/11; C07H 15/63; C12Q 1/68
(52) U.S. Cl. ............... 536/23.1; 435/69.1; 435/455; 435/471; 435/252.3; 435/320.1; 435/810; 435/6
(58) Field of Search ................ 536/23.1; 435/69.1, 435/455, 471, 252.3, 320.1, 810, 6

(56) References Cited

PUBLICATIONS

Abu El–Asrar, et al., "Retinal vasculitis"; Current Opinion in Ophthalmology, vol. 8, No. 3, Jun. 1997.

Gordon, et al., "Identification of Candidate Microbiol Sequences Associated With Inflammatory Lesions of Giant Cell Arteritis (GCA)"; 1999 ARVO submission, Selected as an oral presentation given at ARVO, Fort Lauderdale, FL, May 1999.

Gordon, et al., "Molecular Approaches to Identify Candidate Pathogens in Giant Cell Arteritis"; Abstract submitted to the 1999 North American Neuro–Ophthalmology Society annual meeting, oral presentation, Snowmass, Colorado, Mar. 1999.

Brian E. Wind, DO, "Temporal arteritis, Aggessive treatment prevents visual complications"; The Practical PeerReviewed Journal for Primary Care Physicians, Postgraduate Medicine, vol. 91, No. 6, May 1, 1992.

Gordon, et al., "Visual Loss in Giant Cell Arteritis"; JAMA, vol. 280, No. 4, Jul. 22/29, 1998.

Jose L. Tovilla–Canales, MD, "Ocular manifestations of giant cell arteritis"; Current Opinion in Opthamology, vol. 9, No. 6, Dec. 1998.

Ghanchi, et al., "Current Concepts in Giant Cell (Temporal) Arteritis"; Survey of Ophthalmology, vol. 42, No. 2, Sep.–Oct. 1997.

*Primary Examiner*—Phillip Gambel
*Assistant Examiner*—Jessica H. Roark
(74) *Attorney, Agent, or Firm*—Smith, Gambrell & Russell LLP; Suzannah K. Sundby

(57) ABSTRACT

This invention provides nucleic acids and methods for making and using them. The compositions and methods of the invention are used to diagnose and treat Giant Cell Arteritis (GCA).

18 Claims, 3 Drawing Sheets

BINDING OF FUSION PROTEIN GCA1b-GST TO HUMAN SERUM IgG

BINDING OF FUSION PROTEIN GCA17-GST TO HUMAN SERUM IgG

BINDING OF GCA FUSION PROTEINS TO HUMAN SERUM IgG

NUCLEIC ACIDS FOR THE DIAGNOSIS AND TREATMENT OF GIANT CELL ARTERITIS

FIELD OF THE INVENTION

This invention generally pertains to the fields of medicine and medical diagnostics. In particular, this invention provides novel genes and polypeptides and methods for making and using them. Specifically, the compositions and methods of the invention are used to diagnose and treat Giant Cell Arteritis (GCA).

BACKGROUND OF THE INVENTION

Giant cell arteritis (GCA) is a systemic vasculitis that is a serious and potentially blinding rheumatologic disease of the elderly. Current treatment of GCA requires systemic immunosuppression with profound morbidity in the affected elderly population. GCA is widely believed to be immune-mediated; however, the etiology and pathogenesis of this systemic vasculitis remains unidentified. Furthermore, diagnosis of GCA is difficult because it relies on a constellation of nonspecific signs and symptoms and a diagnostic arterial biopsy. Significantly, blindness may be the first symptom of GCA. Thus, if a way were found to better diagnose or even screen for early onset or predisposition for GCA at an earlier stage of the disease, many cases of blindness and many lives would be saved.

Currently, corticosteroids are critical in the treatment of giant cell arteritis; they reduce the incidence of blindness and rapidly relieve symptoms. However, the amounts of steroids (e.g., prednisone) needed are significant and not without side effects, particularly as they usually must be given over an extended period of time, usually about two years. Steroid treatment is not unformly effective and causes significant morbidity in up to 40% of patients because of hypertension, osteoporosis, infection, glucose dysregulation, fluid overload, and aseptic necrosis of the hip or shoulder. Alternative use of nonsteroidal anti-inflammatory drugs (NSAIDs) will lessen the painful symptoms, but they do not prevent the blindness or vascular problems. Accordingly, new methods of treating GCA are needed. The present invention addresses these and other needs.

SUMMARY OF THE INVENTION

The present invention provides novel compositions and methods in the screening for, diagnosis of and treatment of GCA.

The invention provides an isolated or recombinant nucleic acid comprising a nucleic acid sequence having at least 75% sequence identity to SEQ ID NO:1 or a nucleic acid encoding a polypeptide, wherein the polypeptide has a sequence as set forth in SEQ ID NO:2; or a nucleic acid sequence having at least 75% sequence identity to SEQ ID NO:3 or a nucleic acid encoding a polypeptide, wherein the polypeptide has a sequence as set forth in SEQ ID NO:4; or a nucleic acid sequence having at least 85% sequence identity to SEQ ID NO:5 or a nucleic acid encoding a polypeptide, wherein the polypeptide has a sequence as set forth in SEQ ID NO:6; or a nucleic acid sequence having at least 75% sequence identity to SEQ ID NO:7 or a nucleic acid encoding a polypeptide, wherein the polypeptide has a sequence as set forth in SEQ ID NO:8. In various embodiments, the sequence identity to SEQ ID NO:1 is at least 80%, 85%, 90%, 95%, and 98%; the sequence identity to SEQ ID NO:3 is at least 80%, 85%, 90%, 95%, and 98%; the sequence 8 identity to SEQ ID NO:5 is at least 900%, 95%, and 98%; and, the sequence identity to SEQ ID NO:7 is at least 80%, 85%, 90%, 95%, and 98%. The nucleic acid can also comprises a sequence as set forth in SEQ ID NO:1; SEQ ID NO:3; SEQ ID NO:5; or SEQ ID NO:7.

The invention also provides an isolated or recombinant nucleic acid comprising a nucleic acid sequence having at least 75% sequence identity to SEQ ID NO:9, SEQ ID NO:10; SEQ ID NO:11; SEQ ID NO:13; SEQ ID NO:14, SEQ ID NO:15 or SEQ ID NO:16; or has a sequence as set forth in SEQ ID NO:12. In alternative embodiments, the sequence identity to SEQ ID NO:9, SEQ ID NO:10; SEQ ID NO:11; SEQ ID NO:13; SEQ ID NO:14, SEQ ID NO:15 or SEQ ID NO:16 is at least 80%, 85%, 90%, 95%, and 98%. The nucleic acid can also have a sequence as set forth in SEQ ID NO:9, SEQ ID NO:10; SEQ ID NO:11; SEQ ID NO:13; SEQ ID NO:14, SEQ ID NO:15 or SEQ ID NO:16.

The invention provides an isolated or recombinant nucleic acid which specifically hybridizes to a nucleic acid comprising a sequence as set forth in SEQ ID NO:1, SEQ ID NO:3, SEQ ID NO:5, SEQ ID NO:7, SEQ ID NO:9, SEQ ID NO:10, SEQ ID NO:11, SEQ ID NO:13, SEQ ID NO:14, SEQ ID NO:15 or SEQ ID NO:16 under stringent conditions, wherein the stringent conditions include a wash step comprising a wash in 0.2×SSC at a temperature of about 65° C. for about 15 minutes. The nucleic acid can be between about 15 and about 200 residues in length; between about 25 and about 100 residues in length; or between about 35 and about 75 residues in length.

The invention provides an expression vector comprising at least one nucleic acid operably linked to a promoter, wherein the nucleic acid comprises a nucleic acid sequence of the invention. In the expression vector, the nucleic acid can be operably linked to the promoter in the sense orientation or the antisense orientation. Also provided is a transformed cell comprising the nucleic acids and/or expression vectors of the invention.

The invention provides a polymerase chain reaction (PCR) primer pair that can amplify a nucleic acid sequence of the invention, or a subsequence thereo, under in situ or in vitro conditions.

The invention provides an isolated or recombinantly expressed polypeptide, said polypeptide encoded by nucleic acid which specifically hybridizes to a nucleic acid comprising a sequence as set forth in SEQ ID NO:1, SEQ ID NO:3, SEQ ID NO:5, SEQ ID NO:7, SEQ ID NO:9, SEQ ID NO:10, SEQ ID NO:11, SEQ ID NO:13, SEQ ID NO:14, SEQ ID NO:15 or SEQ ID NO:16 under stringent conditions, wherein the stringent conditions include a wash step comprising a wash in 0.2×SSC at a temperature of about 65° C. for about 15 minutes.

The invention provides a polypeptide encoded by SEQ ID NO:1, SEQ ID NO:3, SEQ ID NO:5, SEQ ID NO:7, SEQ ID NO:9, SEQ ID NO:10, SEQ ID NO:11, SEQ ID NO:12, SEQ ID NO:13, SEQ ID NO:14, SEQ ID NO:15 or SEQ ID NO:16 in any reading frame on either strand (e.g., coding strand or complementary strand); such exemplary polypeptide and peptide sequences of the invention are set forth herein.

The invention provides an isolated or recombinantly expressed polypeptide having 75% sequence identity to SEQ ID NO:2, 75% sequence identity to SEQ ID NO:4, having 85% sequence to SEQ ID NO:6 or 75% sequence identity to SEQ ID NO:8. In alternative embodiments, the polypeptide has 80%, 85%, 90%, 95%, and 98% sequence identity to an amino acid sequence as set forth in SEQ ID NO:2, SEQ ID NO:4, and SEQ ID NO:8; and, 90%, 95%, and 98% sequence identity to an amino acid sequence as set forth in SEQ ID NO:6. The isolated or recombinantly expressed polypeptide of the invention can have an amino acid sequence as set forth in SEQ ID NO:2, SEQ ID NO:4, SEQ ID NO:6, or SEQ ID NO:8. The isolated or recombinantly expressed polypeptide can be between about 15 and about 200 residues in length; between about 25 and about 100 residues in length; or between about 35 and about 75 residues in length.

The invention further provides an immunogenic peptide comprising a subsequence of a polypeptide of the invention, exemplary sequences of which are provided herein. For example, the immunogenic peptide can have a sequence as set forth from about residue 1 to residue 92 of SEQ ID NO:2; about residue 1 to 124 of SEQ ID NO:4; about residue 1 to 48 of SEQ ID NO:6; or about residue 1 to 81 of SEQ ID NO:8. The invention also provides a fusion protein comprising a polypeptide, particularly an immunogenic peptide, and a heterologous sequence. The heterologous sequence can be any sequence not GCA-associated; for example, a sequence that aids in the expression, isolation/purification of the fusion protein.

The invention provides an isolated or recombinant antibody or binding fragment thereof which specifically binds to a polypeptide or peptide or an immunogenic fragment thereof, of the invention. The antibody can be a monoclonal antibody or a polyclonal antibody or binding fragment thereof. The invention further provides a hybridoma cell line comprising (e.g., producing) a monoclonal antibody of the invention.

The invention provides kits for detecting the presence of nucleic acid sequences associated with GCA (typically from, e.g., a serum, urine, tissue or biopsy sample) comprising a nucleic acid of the invention, or combinations thereof, where a nucleic acid in the sample detectably hybridizes to a nucleic acid of the invention under in situ or in vitro conditions. Also provided are kits for detecting the presence of nucleic acid sequences associated with GCA (also typically from, e.g., a serum, urine, tissue or biopsy sample) comprising an amplification primer pair that can amplify a sample nucleic acid having a sequence as set forth in claim 1, claim 5 or claim 9 under in situ or in vitro conditions. Further provided are kits for detecting the presence of polypeptide sequences associated with GCA comprising an antibody of the invention.

The invention also provides kits, e.g., ELISA kits, for detecting the presence of human antibodies associated with GCA in a sample comprising a polypeptide of the invention. The polypeptides or peptides in the kit can be immobilized. The kit can further comprise a non-human antibody or antisera that specifically binds to a human antibody under in situ or in vitro conditions. As described below, the non-human antibody in the kit can further comprise a detectable tag (e.g., an enzyme, a radionuclide, biotin, and the like, as discussed below), or the invention can comprise a second antibody capable of binding to the first non-human antibody.

The invention provides arrays (also called "DNA chips" or "microarrays") of oligonucleotide probes for the identification of GCA-associated nucleic acid in a sample. The nucleic acid in these arrays are typically immobilized on a solid support comprising, amongst other nucleic acids, a GCA-associated nucleic acid of the invention.

The invention provides methods for diagnosing or determining predisposition for GCA comprising the following steps: (a) providing an antibody that specifically binds to a polypeptide associated with GCA, wherein the antibody has the same specificity as an antibody of the invention (that binds to a GCA-associated peptide or polypeptide); or, a nucleic acid that can detectably hybridizes to a nucleic acid of the invention under in situ or in vitro conditions; (b) providing a tissue or fluid (e.g., whole blood, serum or urine) sample; (c) contacting the antibody or nucleic acid with the sample; and (d) detecting whether the antibody specifically binds to a polypeptide in the tissue or serum sample or the nucleic acid hybridizes to a nucleic acid in the tissue or serum sample; wherein the specific binding or hybridization is diagnostic for or determines a predisposition for GCA.

The invention provides methods for diagnosing or determining predisposition for GCA comprising the following steps: (a) providing a nucleic acid amplification primer pair of the invention that can amplify a GCA-associated nucleic acid under in situ or in vitro conditions; (b) providing a tissue or fluid (eg., whole blood, serum or urine) sample; (c) contacting the primer in pair with the tissue or fluid (e.g., whole blood, serum or urine) sample under amplification reaction conditions; and (d) detecting whether the primer pair has amplified a nucleic acid in the sample; wherein hybridization is diagnostic for or determines a predisposition for GCA.

The invention provides methods for diagnosing or determining predisposition for GCA comprising the following steps: (a) providing a polypeptide or peptide of the invention (a GCA-associated polypeptide); (b) providing a tissue or fluid (e.g., whole blood, serum or urine) sample; (c) contacting the sample with the polypeptide or peptide under physiologic conditions; and (d) detecting whether an antibody in the sample specifically binds to a polypeptide or peptide of step (a); wherein antibody binding is diagnostic for or determines a predisposition for GCA. In this method the detection in step (d) can be an ELISA assay or equivalent thereof, as discussed below.

The invention provides methods for isolating nucleic acid sequences associated with GCA comprising the following steps: (a) providing a first tissue sample from a tissue or fluid specimen not showing histologic or other signs of GCA and a second tissue sample from a tissue or fluid specimen showing histologic or other signs of GCA; (b) isolating the nucleic acid from both samples; (c) subtracting nucleic acid from the first sample from the second sample to isolate nucleic acid only present in the second sample, wherein the isolated nucleic acid from the second sample is associated with GCA-affected tissue and not normal tissue. This aspect of the invention can incorporate all variations and equivalents of subtractive hybridization techniques, as described below. In this method, the first and the second tissue sections can be taken from a "skip" lesion of a temporal artery of a GCA patient.

The invention provides methods for isolating lymphocytes involved in the pathogenesis of GCA comprising the following steps: (a) incubating a GCA-associated polypeptide or peptide of the invention with a plurality of adherent, irradiated antigen presenting cell cultures; (b) contacting a sample of isolated lymphocytes from a GCA patient with the polypeptide-incubated adherent antigen presenting cell cultures of step (a); (c) culturing the cells contacted in step (b) for sufficient time to allow for cytokine secretion or cell proliferation; and (d) detecting which cell culture comprises proliferating cells or cells secreting cytokines, wherein proliferation or secretion of cytokines indicates the isolated lymphocytes are involved in the pathogenesis of GCA. In this method, the lymphocytes can be B cells, stem cells or T cells. The cells can be cultured for about 2 to 5 days before cell proliferation or cytokine secretion is analyzed.

The invention provides methods for generating antibodies for the diagnosis or treatment of GCA comprising administering a GCA-associated polypeptide or peptide of the invention in amounts sufficient to generate an immune response. The immune response can be primarily humoral, cell-based, or a combination thereof. The GCA-associated polypeptides can be administered to non-human animals to generate non-human antibodies for diagnostic tests (they can also be administered to human Ab-gene-carrying mice to generate all-human antibodies, as discussed below). The GCA-associated polypeptides also can be administered to humans as vaccines for the treatment or prevention of GCA.

The invention provides methods for making the nucleic acids, polypeptides, and antibodies of the invention, as described herein. These can be isolated from nature, made in recombinant expression systems or can be entirely synthetic, as described herein. For example, nucleic acids within the scope of the invention can be identified and isolated using, e.g., nucleic acid hybridization techniques, including in situ hybridization, traditional techniques such as dot-blotting of cDNA or genomic libraries, or amplification techniques, such as PCR. Amplification primers can be designed directly from the GCA-associated nucleic acids described herein, or they can be modified, degenerate primers, as discussed below. Polypeptides can be identified and isolated using a variety of methods, including, e.g., analysis of ORFs from GCA-associated nucleic acids, binding with GCA-associated antibodies, wherein the antibodies can be, e.g., isolated from human patients or generated using the polypeptides or peptides of the invention, and the binding can be, e.g., in tissue samples or expression libraries. Antibodies can be made by inoculation of mammalian recipients using, e.g., the polypeptides or peptides of the invention, or, they can be isolated from immunized animals or expression libraries, e.g., phage (antibody binding site) expression libraries.

A further understanding of the nature and advantages of the present invention is realized by reference to the remaining portions of the specification, the figures and claims.

All publications, patents and patent applications cited herein are hereby expressly incorporated by reference for all purposes.

DETAILED DESCRIPTION

Figure 1:
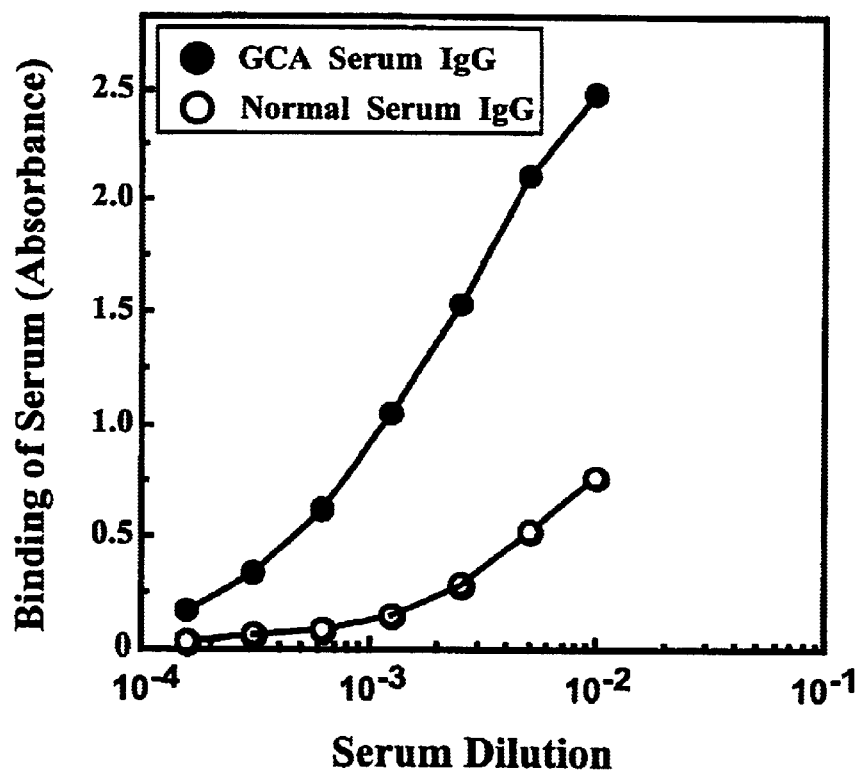
FIG. 1 illustrates a representative experiment using the fusion protein GCA1b-GST in serum ELISA using various dilution of human serum from a GCA+ and GCA− individual and detecting for bound human IgG.

The present invention provides a novel strategy for the detection, diagnosis and treatment of Giant Cell Arteritis (GCA). The invention provides for compositions and methods useful for early diagnosis of (including assessing the predisposition for acquiring GCA) and the treatment of GCA. Use of the invention to screen elderly patients for predisposition to GCA and early diagnosis of GCA is particularly needed to prevent a common cause of blindness in our aging population. GCA is seen especially in the elderly, usually at a mean age of about 70 years old. Blindness is the most serious and irreversible feature of GCA, where it can be sudden, painless and permanent. Involvement of both eyes can occur. Significantly, blindness may be the initial clinical presentation of GCA. Accordingly, use of the methods and composition of the invention will prevent or ameliorate (in addition to treating) significant numbers of incidents of blindness in our aging population.

The invention is based on the discovery that novel sequences can be associated with GCA lesions. While the invention is not limited by any particular theory or mechanism, these unique-GCA associated sequences may be associated with a pathology initiating or causative microorganism. Accordingly, subtractive hybridization of normal (non-involved) from GCA-involved tissue led to the discovery of the novel GCA-associated sequences of the invention. Translation of exemplary sequences to recombinant polypeptides (in the form of fusion proteins for convenience of isolation and manipulation) led to the discovery that GCA patients have circulating antibodies that specifically bind to the polypeptides of the invention. Accordingly, the peptides and polypeptides of the invention are used in kits and methods for diagnosing GCA by identifying circulating anti-GCA antibodies in the serum, urine or tissue samples of patients. Because blindness may be the first presenting symptom of GCA, the diagnostic methods of the invention can be used to screen for GCA on patients that, while having no symptoms of GCA, do have a relatively high probability of suffering from GCA, such as elderly patients.

DEFINITIONS

Unless defined otherwise, all technical and scientific terms used herein have the meaning commonly understood by a person skilled in the art to which this invention belongs. As used herein, the following terms have the meanings ascribed to them unless specified otherwise.

The term "amplifing" and "amplification" as used herein incorporates its common usage and refers to the use of any suitable amplification methodology for generating or detecting recombinant or naturally expressed nucleic acid, as described in detail, below. For example, the invention provides methods and reagents (e.g., specific degenerate oligonucteotide primer pairs) for amplifying (eg., by polymerase chain reaction, PCR) naturally expressed (e.g., genomic or mRNA) or recombinant (e.g., cDNA) nucleic acids of the invention (e.g., GCA-associated sequences of the invention) in vivo or in vitro.

The term "antibody" includes both intact antibodies having at least two heavy (H) chains and two light (L) chains interconnected by disulfide bonds and antigen binding fragments thereof either isolated from natural sources, recombinantly generated or partially or entirely synthetic. Examples of antigen binding fragments include, e.g., (i) a Fab fragment, a monovalent fragment consisting of the VL, VH, CL and CH1 domains; (ii) a F(ab')2 fragment, a bivalent fragment comprising two Fab fragments linked by a disulfide bridge at the hinge region; (iii) a Fd fragment consisting of the VH and CH1 domains; (iv) a Fv fragment consisting of the VL and VH domains of a single arm of an antibody, (v) a dAb fragment (Ward et al., (1989) Nature 341:544–546), which consists of a VH domain; and (vi) an isolated complementarity determining region (CDR). Although the two domains of the Fv fragment, VL and VH, are coded for by separate genes, they can be joined, using recombinant methods, by a synthetic linker that enables them to be made as a single protein chain in which the VL and VH regions pair to form monovalent molecules (known as single chain Fv (scFv); See e.g., Bird et al., (1988) *Science* 242:423426; and Huston et al. (1988) *Proc. Natl. Acad. Sci. USA* 85:5879–5883). Single chain antibodies are also antibodies of the invention. Fragments can be also prepared by enzymatic or chemical cleavage of intact antibodies. "Specific binding" refers to antibody binding to a predetermined antigen. Typically, the antibody binds with an association constant ($K_a$) of at least about $1\times10^6$ $M^{-1}$ or $10^7$ $M^{-1}$, or about $10^8$ $M^{-1}$ to $10^9$ $M^{-1}$, or about $10^{10}$ $M^{-1}$ to $10^{11}$ $M^{-1}$ or higher, and binds to the predetermined antigen with an affinity that is at least two-fold greater than its affinity for binding to a non-specific antigen (e.g., BSA, casein) other than the predetermined antigen or a closely-related antigen. The phrases "an antibody recognizing an antigen" and "an antibody specific for an antigen" are used interchangeably herein with the term "an antibody which binds specifically to an antigen." The term "high affinity" for an IgG antibody refers to an equilibrium association constant ($K_a$) of at least about $10^7 M^{-1}$, at least about $10^8 M^{-1}$, at least about $10^9 M^{-1}$, at least about $10^{10} M^{-1}$, at least about $10^{11} M^{-1}$, or at least about $10^{12} M^{-1}$ or greater, e.g., up to $10^{13} M^{-1}$ or $10^{14} M^{-1}$ or greater. However, "high affinity" binding can vary for other antibody isotypes.

The term "array" includes any array of probes, e.g., nucleic acids stably associated with the surface of a solid support under hybridization conditions sufficient to produce a hybridization pattern, as discussed in detail, below.

The term "expression vector" refers to any recombinant expression system for the purpose of expressing a nucleic acid sequence of the invention in vitro or in vivo, constitutively or inducibly, in any cell, including prokaryotic, yeast, fungal, plant, insect or mammalian cell. The term includes linear or circular expression systems. The term includes expression systems that remain episomal or integrate into the host cell genome. The expression systems can have the ability to self-replicate or not, i.e., drive only transient expression in a cell. The term includes recombinant "expression cassettes" which contain only the minimum elements needed for transcription of the recombinant nucleic acid.

The term "fusion protein" or "fusion polypeptide" includes polypeptides having sequences which are normally unrelated to each other, e.g., a polypeptide of the invention (e.g., SEQ ID NO:2, SEQ ID NO:4, SEQ ID NO:6, SEQ ID NO:8) linked to a "heterologous sequence" (see definition below), as discussed in detail, below.

The term "giant cell arteritis" or "GCA" describes the chronic inflammatory disease characterized by the progressive inflammation of many arteries of the body (panartenitis), and is sometimes also known as "temporal arteritis," "Horton's disease," "cranial artertis," or "granulomatous arteritis." It is typically diagnosed by clinical symptoms and by histopathologic analysis, as described below.

The term "heterologous" when used with reference to a nucleic acid or polypeptide, indicates that a sequence that comprises two or more subsequences which are not found in the same relationship to each other as normally found in nature, or is recombinantly engineered so that its level of expression, or physical relationship to other nucleic acids or other molecules in a cell, or structure, is not normally found in nature. For instance, a heterologous nucleic acid is typically recombinantly produced, having two or more sequences from unrelated genes arranged in a manner not found in nature; e.g., a nucleic acid open reading frame (ORF) of the invention operatively linked to a promoter sequence inserted into an expression cassette, e.g., a vector, of the invention. As another example, a polypeptide of the invention is linked to tag, e.g., a detection- and purification-facilitating domain, as a fusion protein.

As used herein, the term "immune response" includes any humoral (antibody) or cellular immune response or combination thereof.

As used herein, "isolated," when referring to a molecule or composition, such as, e.g., an isolated infected cell comprising a nucleic acid sequence derived from a library of the invention, means that the molecule or composition (including, e.g., a cell) is separated from at least one other compound, such as a protein, DNA, RNA, or other contaminants with which it is associated in vivo or in its naturally occurring state. Thus, a nucleic acid or polypeptide or peptide sequence is considered isolated when it has been isolated from any other component with which it is naturally associated. An isolated composition can, however, also be substantially pure. An isolated composition can be in a homogeneous state. It can be in a dry or an aqueous solution. Purity and homogeneity can be determined, e.g., using any analytical chemistry technique, as described herein.

The term "nucleic acid" or "nucleic acid sequence" refers to a deoxy-ribonucleotide or ribonucleotide oligonucleotide, including single- or double-stranded, or coding or non-coding (e.g., "antisense") forms. The term encompasses nucleic acids, i.e., oligonucleotides, containing known analogues of natural nucleotides. The term also encompasses nucleic-acid-like structures with synthetic backbones, see e.g., Oligonucleotides and Analogues, a Practical Approach, ed. F. Eckstein, Oxford Univ. Press (1991); Antisense Strategies, Annals of the N.Y. Academy of Sciences, Vol 600, Eds. Baserga et al. (NYAS 1992); Milligan (1993) J. Med. Chem. 36:1923–1937; Antisense Research and Applications (1993, CRC Press), WO 97/03211; WO 96/39154; Mata (1997) Toxicol. Appl. Pharmacol. 144:189–197; Strauss-Soukup (1997) Biochemistry 36:8692–8698; Samstag (1996) Antisense Nucleic Acid Drug Dev 6:153–156.

As used herein, the term "operably linked," refers to a functional relationship between two or more nucleic acid (e.g., DNA) segments. Typically, it refers to the functional relationship of a transcriptional regulatory sequence to a transcribed sequence. For example, a promoter (defined below) is operably linked to a coding sequence, such as a nucleic acid of the invention, if it stimulates or modulates the transcription of the coding sequence in an appropriate host cell or other expression system. Generally, promoter transcriptional regulatory sequences that are operably linked to a transcribed sequence are physically contiguous to the transcribed sequence, i.e., they are cis-acting. However, some transcriptional regulatory sequences, such as enhancers, need not be physically contiguous or located in close proximity to the coding sequences whose transcription they enhance. For example, in one embodiment, a promoter is operably linked to an ORF-containing nucleic acid sequence of the invention, as exemplified by, e.g., SEQ ID NO:1, SEQ ID NO:3, SEQ ID NO:5 and SEQ ID NO:7.

The terms "polypeptide," "protein," and "peptide" include compositions of the invention that also include "analogs," or "conservative variants" and "mimetics" ("peptidomimetics") with structures and activity that substantially correspond to the exemplary sequences, such as SEQ ID NO:2; SEQ ID NO:4; SEQ ID NO:6; or SEQ ID NO:8. Thus, the terms "conservative variant" or "analog" or "mimetic" also refer to a polypeptide or peptide which has a modified amino acid sequence, such that the change(s) do not substantially alter the polypeptide's (the conservative variant's) structure and/or activity (e.g., immunogenicity, ability to bind to human antibodies, etc.), as defined herein. These include conservatively modified variations of an amino acid sequence, i.e., amino acid substitutions, additions or deletions of those residues that are not critical for protein activity, or substitution of amino acids with residues having similar properties (e.g., acidic, basic, positively or negatively charged, polar or non-polar, etc.) such that the substitutions of even critical amino acids does not substantially alter structure and/or activity. Conservative substitution tables providing functionally similar amino acids are well known in the art. For example, one exemplary guideline to select conservative substitutions includes (original residue followed by exemplary substitution): alaigly or ser arg/lys; asn/gln or his; asp/glu; cys/ser; gln/asn; gly/asp; gly/ala or pro; his/asn or gin; ile/leu or val; leu/ile or val; lys/arg or gln or glu; met/leu or tyr or ile; phe/met or leu or tyr; ser/thr; thr/ser; trp/tyr; tyr/trp or phe; val/ile or leu. An alternative exemplary guideline uses the following six groups, each containing amino acids that are conservative substitutions for one another: 1) Alanine (A), Serine (S), Threonine (T); 2) Aspartic acid (D), Glutamic acid (E); 3) Asparagine (N), Glutamine (Q); 4) Arginine (R), Lysine (K); 5) Isoleucine (I), Leucine (L), Methionine (M), Valine (V); and 6) Phenylalanine (F), Tyrosine (Y), Tryptophan (W); (see also, e.g., Creighton (1984) Proteins, W.H. Freeman and Company; Schulz and Schimer (1979) Principles of Protein Structure, Springer-Verlag). One of skill in the art will appreciate that the above-identified substitutions are not the only possible conservative substitutions. For example, for some purposes, one may regard all charged amino acids as conservative substitutions for each other whether they are positive or negative. In addition, individual substitutions, deletions or additions that alter, add or delete a single amino acid or a small percentage of amino acids in an encoded sequence can also be considered "conservatively modified variations."

The terms "mimetic" and "peptidomimetic" refer to a synthetic chemical compound that has substantially the same structural and/or functional characteristics of the polypeptides of the invention (e.g., ability to bind, or "capture," human antibodies in an ELISA). The mimetic can be either entirely composed of synthetic, non-natural analogues of amino acids, or, is a chimeric molecule of partly natural peptide amino acids and partly non-natural analogs of amino acids. The mimetic can also incorporate any amount of natural amino acid conservative substitutions as long as such substitutions also do not substantially alter the mimetics' structure and/or activity. As with polypeptides of the invention which are conservative variants, routine experimentation will determine whether a mimetic is within the scope of the invention, i.e., that its structure and/or function is not substantially altered. Polypeptide mimetic compositions can contain any combination of non-natural structural components, which are typically from three structural groups: a) residue linkage groups other than the natural amide bond ("peptide bond") linkages; b) non-natural residues in place of naturally occurring amino acid residues; or c) residues which induce secondary structural mimicry, i.e., to induce or stabilize a secondary structure, e.g., a beta turn, gamma turn, beta sheet, alpha helix conformation, and the like. A polypeptide can be characterized as a mimetic when all or some of its residues are joined by chemical means other than natural peptide bonds. Individual peptidomimetic residues can be joined by peptide bonds, other chemical bonds or coupling means, such as, e.g., glutaraldehyde, N-hydroxysuccinimide esters, bifunctional maleimides, N,N'-dicyclohexylcarbodiimide (DCC) or N,N'-diisopropylcarbodiimide (DIC). Linking groups that can be an alternative to the traditional amide bond ("peptide bond") linkages include, e.g., ketomethylene (e.g., —C(=O)CH$_2$— for —C(=O)—NH—), aminomethylene (CH$_2$—NH), ethylene, olefin (CH=CH), ether (CH$_2$—O), thioether (CH$_2$—S), tetrazole (CN$_4$—), thiazole, retroamide, thioamide, or ester (see, e.g., Spatola (1983) in Chemistry and Biochemistry of Amino Acids, Peptides and Proteins, Vol. 7, pp 267–357, "Peptide Backbone Modifications," Marcell Dekker, NY). A polypeptide can also be characterized as a mimetic by containing all or some non-natural residues in place of naturally occurring amino acid residues; non-natural residues are well described in the scientific and patent literature.

The term "pharmaceutical composition" refers to a composition suitable for pharmaceutical use in a subject. The pharmaceutical compositions of this invention are formulations that comprise a pharmacologically effective amount of a composition comprising, e.g., a nucleic acid (including, e.g., ribozymes, antisense oligonucleotides, and other inhibitory nucleic acid variations), a vector, or an antibody of the invention, and a pharmaceutically acceptable carrier.

As used herein, the term "promoter" includes all sequences capable of driving transcription of a coding sequence in an expression system. Thus, promoters used in the constructs of the invention include cis-acting transcriptional control elements and regulatory sequences that are involved in regulating or modulating the timing and/or rate of transcription of a nucleic acid of the invention. For example, a promoter can be a cis-acting transcriptional control element, including an enhancer, a promoter, a transcription terminator, an origin of replication, a chromosomal integration sequence, 5' and 3' untranslated regions, or an intronic sequence, which are involved in transcriptional regulation. These cis-acting sequences typically interact with proteins or other biomolecules to carry out (turn on/off, regulate, modulate, etc.) transcription.

As used herein, "recombinant" refers to a polynucleotide synthesized or otherwise manipulated in vitro (e.g., "recombinant polynucleotide"), to methods of using recombinant polynucleotides to produce gene products in cells or other biological systems, or to a polypeptide ("recombinant protein") encoded by a recombinant polynucleotide. "Recombinant means" also encompass the ligation of nucleic acids having various coding regions or domains or promoter sequences from different sources into an expression cassette or vector for expression of, e.g., inducible or constitutive expression of polypeptide coding sequences in the vectors of invention.

As used herein, the "sequence" of a nucleic acid or gene refers to the order of nucleotides in the polynucleotide, including either or both strands (sense and antisense) of a double-stranded DNA molecule, e.g., the sequence of both the coding strand and its complement, or of a single-stranded nucleic acid molecule (sense or antisense). For example, in alternative embodiments, promoters drive the transcription of sense and/or antisense polynucleotide sequences of the invention, as exemplified by SEQ ID NO:1, SEQ ID NO:3, SEQ ID NO:5, and SEQ ID NO:7.

The terms "identical" or percent "sequence identity," in the context of two or more nucleic acids or polypeptide sequences, refer to two or more sequences or subsequences that are the same or have a specified percentage of nucleotides (or amino acid residues) that are the same, when compared and aligned for maximum correspondence over a comparison window, as measured using one of the following sequence comparison algorithms or by manual alignment and visual inspection. This definition also refers to the complement (antisense strand) of a sequence. For example, in alternative embodiments, nucleic acids within the scope of the invention include those with a nucleotide sequence identity that is at least about 60%, at least about 65%, at least about 70%, at least about 75%, at least about 80%, at least about 85%, at least about 90%, and at least about 95% of the exemplary sequences set forth in SEQ ID NO:1, SEQ ID NO:3, SEQ ID NO:5, and SEQ ID NO:7; or, SEQ ID NO:9 through SEQ ID NO:14.

In alternative embodiments, polypeptides within the scope of the invention include those with an amino acid sequence identity that is at least about 60%, at least about 65%, at least about 70%, at least about 75%, at least about 80%, at least about 85%, at least about 90%, and at least about 95% of the exemplary sequences set forth in SEQ ID NO:2, SEQ ID NO:4, SEQ ID NO:6, and SEQ ID NO:8.

Two sequences with these levels of identity are "substantially identical" and within the scope of the invention. Thus, if a nucleic acid sequence has the requisite sequence identity to SEQ ID NO:1, SEQ ID NO:3, SEQ ID NO:5, or SEQ ID NO:7, or, SEQ ID NO:9 through SEQ ID NO:14, or a subsequence thereof, it also is a polynucleotide sequence within the scope of the an invention. If a polynucleotide sequence has the requisite sequence identity to SEQ ID NO:2, SEQ ID NO:4, SEQ ID NO:6, and SEQ ID NO:8, or a subsequence thereof, it also is a polypeptide within the scope of the invention.

The percent identity can exists over a region of the sequence that is at least about 25 nucleotides or amino acid residues in length, or, alternatively, over a region that is at least about 50 to 100 nucleotides or amino acids in length. Parameters (including, e.g., window sizes, gap penalties and the like) to be used in calculating "percent sequence identities" between two nucleic acids or polypeptides to identify and determine whether one is within the scope of the invention are described in detail, below.

The phrase "selectively (or specifically) hybridizes to" refers to the binding, duplexing, or hybridizing of a molecule to a particular nucleotide sequence under stringent hybridization conditions when that sequence is present in a complex mixture (e.g., total cellular or library DNA or RNA), wherein the particular nucleotide sequence is detected at least at about 10 times background. In one embodiment, a nucleic acid can be determined to be within the scope of the invention (e.g., is substantially identical to SEQ ID NO:1, 3, 5, or 7, or, SEQ ID NO:9 through SEQ ID NO:14) by its ability to hybridize under stringent conditions to a nucleic acid otherwise determined to be within the scope of the invention (such as the exemplary sequences described herein).

The phrase "stringent hybridization conditions" refers to conditions under which a probe will primarily hybridize to its target subsequence, typically in a complex mixture of nucleic acid, but to no other sequences in significant amounts, is described in detail below. A positive signal (e.g., identification of a nucleic acid of the invention) is about 10 times background hybridization.

Nucleic Acids, Vectors and Primer Pairs

This invention provides novel nucleic acids for use in the diagnosis and treatment of Giant Cell Arthritis (GCA) and means to make and express those nucleic acids. As the genes and vectors of the invention can be made and expressed in vitro or in vivo, the invention provides for a variety of means of making and expressing these genes and vectors. One of skill will recognize that desire phenotypes associated with altered gene activity can be obtained by modulating the expression or activity of the genes and nucleic acids (e.g., promoters) within the vectors of the invention. Any of the known methods described for increasing or decreasing expression or activity can be used for this invention. The invention can be practiced in conjunction with any method or protocol known in the art, which are well described in the scientific and patent literature.

General Techniques

The nucleic acid sequences of the invention and other nucleic acids used to practice this invention, whether RNA, cDNA, genomic DNA, vectors, viruses or hybrids thereof, may be isolated from a variety of sources, genetically engineered, amplified, and/or expressed recombinantly. Any recombinant expression system can be used, including, in addition to bacterial cells, e.g., mammalian, yeast, insect or plant cell expression systems.

Alternatively, these nucleic acids can be synthesized in vitro by well-known chemical synthesis techniques, as described in, e.g., Carruthers (1982) Cold Spring Harbor Symp. Quant. Biol. 47:411–418; Adams (1983) J. Am. Chem. Soc. 105:661; Belousov (1997) Nucleic Acids Res. 25:3440–3444; Frenkel (1995) Free Radic. Biol. Med. 19:373–380; Blommers (1994) Biochemistry 33:7886–7896; Narang (1979) Meth. Enzymol. 68:90; Brown (1979) Meth. Enzymol. 68:109; Beaucage (1981) Tetra. Lett. 22:1859; U.S. Pat. No. 4,458,066. Double stranded DNA fragments may then be obtained either by synthesizing the complementary strand and annealing the strands together under appropriate conditions, or by adding the complementary strand using DNA polymerase with an appropriate primer sequence.

Techniques for the manipulation of nucleic acids, such as, e.g., generating mutations in sequences, subcloning, labeling probes, sequencing, hybridization and the like are well described in the scientific and patent literature, see, e.g., Sambrook, ed., MOLECULAR CLONING: A LABORATORY MANUAL (2ND ED.), Vols. 1–3, Cold Spring Harbor Laboratory, (1989); CURRENT PROTOCOLS IN MOLECULAR BIOLOGY, Ausubet, ed. John Wiley & Sons, Inc., New York (1997); LABORATORY TECHNIQUES IN BIOCHEMISTRY AND MOLECULAR BIOLOGY: HYBRIDIZATION WITH NUCLEIC ACID PROBES, Part I. Theory and Nucleic Acid Preparation, Tijssen, ed. Elsevier, N.Y. (1993).

Nucleic acids, vectors, capsids, polypeptides, and the like can be analyzed and quantified by any of a number of general means well known to those of skill in the art. These include, e.g., analytical biochemical methods such as NMR, spectrophotometry, radiography, electrophoresis, capillary electrophoresis, high performance liquid chromatography (HPLC), thin layer chromatography (TLC), and hyperdiffusion chromatography, various immunological methods, e.g. fluid or gel precipitin reactions, immunodiffusion, immuno-electrophoresis, radioimmunoassays (RIAs), enzyme-linked immunosorbent assays (ELISAs), immuno-fluorescent assays, Southern analysis, Northern analysis, dot-blot analysis, gel electrophoresis (e.g., SDS-PAGE), RT-PCR, quantitative PCR, other nucleic acid or target or signal amplification methods, radiolabeling, scintillation counting, and affinity chromatography.

Classical Diagnosis, Biopsies and Microdissections of Arteritis Lesions

The invention provides compositions and methods for isolating novel GCA-associated nucleic acids and polypeptides within the scope of the invention. A preferred source of such GCA-associated tissue is from arteritis lesions. Temporal artery segments biopsied from the same individual can yield both normal and arteritis tissue samples. Histopathological analysis can confirm both "normal" and arteritis samples.

In addition to the diagnostic methods provided by the invention, GCA diagnosis can be complemented by histopathologic analysis. The histopathology of a GCA lesion typically shows chronic granulomatous inflammation, often with abnormally large multinucleated cells (giant cells), and destruction of the internal elastic lamina of the artery. Chronic inflammation is sometimes confined to the different branches of the heart's main artery (aorta) and any large arteries can become inflamed. The temporal arteries of the head are most frequently affected (temporal arteritis). In rare cases, veins may also be affected by giant cell arteritis.

Examination of the cellular inflammatory infiltrate in GCA lesions primarily reveals macrophages and CD4+ T cells. Immunohistochemistry demonstrates the diffuse presence of IL-6 or IL-1β expressing CD68+ macrophages. CD68+ cells expressing 72 kD type IV collagenase and the inducible nitric oxide synthase (iNOS) are found in the intima and intima-media of the artery. It is interesting to note that B cells are infrequent in GCA lesions. Lesional B cells and plasma cells are identified in GCA lesions by expression of CD20 and light chain, respectively. These cells can be found in GCA-affected adventitia, both scattered and located in perivascular clusters, in the same tissue microenvironment as the antigenically-activated T cells. These observations suggest that the artery is the site for antigenic encounter and suggest that GCA is mediated by antigen-specific pathogenic T cells.

Clinical symptoms can also help diagnose GCA. The symptoms of GCA may include fatigue, malaise, weight loss, stiffness, muscle pain, fever, and/or headaches. Generalized muscle pain, claudication of the jaw or tongue, or localized scalp or temporal pain, swelling, and tenderness are also common manifestations of GCA. Headache, usually temporal, is present in about 66% of cases. Headache usually begins early in the course of the disease and may be the presenting symptom. The pain is severe and localized to the temple. Scalp tenderness is common. The local vessels are thickened, and tender. Occasionally they are visible. Visual disturbances have been seen in about 25 to 50% of cases. Blindness is the most serious and irreversible feature of GCA, where it can be sudden, painless and permanent. Involvement of both eyes can occur. Blindness may be the initial clinical presentation of SCA.

Neuro-ophthalmic complications include arteritic anterior ischemic optic neuropathy, posterior optic neuropathy, choroidal ischemia, diplopia, retinal arterial occlusions, and ocular ischemic syndromes and occur in up to 70% of GCA. Notably, it is estimated that 15 to 2% of patients with GCA suffer permanent and potentially bilateral visual loss from ischemic infarction of the optic nerve.

Currently used methods to diagnosis GCA rely on an extracranial arterial biopsy that demonstrates a necrotizing vasculitis with mononuclear cell infiltration or granulomatous inflammation. Pathologic evidence of GCA in arterial biopsies can confirm the diagnosis but, because the arterial involvement is discontinuous and may show skip areas, a negative biopsy does not rule out GCA. Thus, in the absence of pathologic confirmation, diagnosis would rely on the presence of a constellation of non-specific signs or symptoms. However, the invention provides additional, more definitive diagnostic (and treatment) procedures.

One exemplary means to biopsy, or isolate, GCA lesions is by dissection with laser-capture microdissection (LCM), either freshly biopsied or archival pathology specimens of GCA-positive arteries from both histopathologically involved and uninvolved areas. Because the vasculitis of GCA occurs in an irregular, or discontinuous pattern (the so-called "skip lesion"), isolation of one artery (or vein, if appropriate) sample can yield both involved and uninvolved tissue samples. Retrieval of selected cells is achieved by activation of a transfer film placed in contact with a tissue section, by a laser beam (30 or 60 micron diameter) that is focused on a selected area of tissue using an inverted microscope. In LCM, a thermoplastic polymer coating (e.g., ethylene vinyl acetate) attached to a rigid support is placed in contact with a tissue section. The EVA polymer over microscopically selected cell clusters is precisely activated by a near-infrared laser pulse and bonds to the targeted area. Removal of the EVA and its support from the tissue section procures the selected cell aggregates for molecular analysis. A computer-controlled arm can precisely position a 40-micron-wide strip of a cylindrical EVA surface onto a sample with a light contact force. Techniques of laser-capture microdissection are known in the art, e.g., the PixCell laser capture microdissection (LCM) system, see, e.g., Kohda (2000) Kidney Int. 57:321–331; Goldsworthy (1999) Mol. Carcinog. 25:86–91; Banks (1999) Electrophoresis 20:689–700; Emmert-Buck (1996) Science 274:998–1001; U.S. Pat. Nos. 5,985,085; 5,859,699.

Hybridization for Identifying Nucleic Acids of the Invention

Nucleic acids within the scope of the invention include isolated or recombinant nucleic acids which specifically hybridize to an exemplary nucleic acid of the invention. Stringent conditions are sequence-dependent and will be different in different circumstances. Longer sequences hybridize specifically at higher temperatures. An extensive guide to the hybridization of nucleic acids is found in Tijssen, Techniques in Biochemistry and Molecular Biology—Hybridization with Nucleic Probes, "Overview of principles of hybridization and the strategy of nucleic acid assays" (1993). Generally, stringent conditions are selected to be about 5 to 10° C. lower than the thermal melting point (Tm) for the specific sequence at a defined ionic strength and pH. The Tm is the temperature (under defined ionic strength, pH, and nucleic acid concentration) at which 50% of the probes complementary to the target hybridize to the target sequence at equilibrium (as the target sequences are present in excess, at Tm, 50% of the probes are occupied at equilibrium). Stringent conditions will be those in which the salt concentration is less than about 1.0 M sodium ion, typically about 0.01 to 1.0 M sodium ion concentration (or other salts) at pH 7.0 to 8.3 and the temperature is at least about 30° C. for short probes (e.g., 10 to 50 nucleotides) and at least about 60° C. for long probes (e.g., greater than 50 nucleotides). Stringent conditions may also be achieved with the addition of destabilizing agents such as formamide.

For selective or specific hybridization, a positive signal (e.g., identification of a nucleic acid of the invention) is about 10 times background hybridization. "Stringent" hybridization conditions that are used to identify substantially identical nucleic acids within the scope of the invention include hybridization in a buffer comprising 50% formamide, 5×SSC, and 1% SDS at 42° C., or hybridization in a buffer comprising 5×SSC and 1% SDS at 65° C., both with a wash of 0.2×SSC and 0.1% SDS at 65° C. Exemplary "Moderately stringent hybridization conditions" include a hybridization in a buffer of 40% formamide, 1 M NaCl, and 1% SDS at 37° C., and a wash in 1×SSC at 45° C. Those of ordinary skill will readily recognize that alternative but comparable hybridization and wash conditions can be utilized to provide conditions of similar stringency.

Nucleic acids which do not hybridize to each other under moderately stringent or stringent hybridization conditions are still substantially identical if the polypeptides which they encode are substantially identical. This may occur, e.g. when a copy of a nucleic acid is created using the maximum codon degeneracy permitted by the genetic code, as discussed herein (see discussion on "conservative substitutions").

However, the selection of a hybridization format is not critical—it is the stringency of the wash conditions that set forth the conditions which determine whether a nucleic acid is within the scope of the invention. Wash conditions used to identify nucleic acids within the scope of the invention include, e.g.: a salt concentration of about 0.02 molar at pH 7 and a temperature of at least about 50° C. or about 55° C. to about 60° C.; or, a salt concentration of about 0.15 M NaCl at 72° C. for about 15 minutes; or, a salt concentration of about 0.2×SSC at a temperature of at least about 50° C. or about 55° C. to about 60° C. for about 15 to about 20 minutes; or, the hybridization complex is washed twice with a solution with a salt concentration of about 2×SSC containing 0.1% SDS at room temperature for 15 minutes and then washed twice by 0.1×SSC containing 0.1% SDS at 68° C. for 15 minutes; or, equivalent conditions. See Sambrook, Tijssen and Ausubel for a description of SSC buffer and equivalent conditions.

Amplification of Nucleic Acids

The invention provides oligonucleotide primers that can amplify nucleic acid encoding GCA-associated nucleic acids. Thus, nucleic acids of the invention can be, e.g., subcloned or measured quantitatively using amplification techniques. Amplification can also be used to identify complementary GCA-associated nucleic acids in tissue biopsies (e.g., from arteritis lesions) or fluid (e.g., serum, whole blood, urine) samples to aid in the diagnosis or treatment of GCA (see below).

Using the exemplary degenerate primer pair sequences of the invention (see below), the skilled artisan can select and design suitable oligonucleotide amplification primers. Amplification methods are also well known in the art, and include, e.g., polymerase chain reaction, PCR (PCR PROTOCOLS, A GUIDE TO METHODS AND APPLICATIONS, ed. Innis, Academic Press, N.Y. (1990) and PCR STRATEGIES (1995), ed. Innis, Academic Press, Inc., N.Y., ligase chain reaction (LCR) (see, e.g., Wu (1989) Genomics 4:560; Landegren (1988) Science 241:1077; Barringer (1990) Gene 89:117); transcription amplification (see, e.g., Kwoh (1989) Proc. Natl. Acad. Sci. USA 86:1173); and, self-sustained sequence replication (see, e.g., Guatelli (1990) Proc. Natl. Acad. Sci. USA 87:1874); Q Beta replicase amplification (see, e.g., Smith (1997) J. Clin. Microbiol. 35:1477–1491), automated Q-beta replicase amplification assay (see, e.g., Burg (1996) Mol. Cell. Probes 10:257–271) and other RNA polymerase mediated techniques (e.g., NASBA, Cangene, Mississauga, Ontario); see also Berger (1987) Methods Enzymol. 152:307–316; Sambrook; Ausubel; U.S. Pat. Nos. 4,683,195 and 4,683,202; Sooknanan (1995) Biotechnology 13:563–564. A continuous amplification reaction method is described by, e.g., U.S. Pat. No. 5,981,179.

Once amplified, the libraries can be cloned, if desired, into any of a variety of vectors using routine molecular biological methods; methods for cloning in vitro amplified nucleic acids are described, eg., U.S. Pat. No. 5,426,039. To facilitate cloning of amplified sequences, restriction enzyme sites can be "built into" the PCR primer pair.

Degenerate Primer Design

In alternative embodiments, primer pairs of the invention are also designed to selectively amplify new nucleic acid sequences found only in arteritis lesions and not in normal vasculature or other normal tissues. To amplify GCA-associated nucleic acids within the scope of the invention, degenerate primer pairs are designed based on the exemplary nucleic acids of the invention, e.g., SEQ ID NO:1, SEQ ID NO:3, SEQ ID NO:5, and SEQ ID NO:7; or, SEQ ID NO:9 through SEQ ID NO:14.

Paradigms to design degenerate primer pairs are well known in the art. For example, a COnsensus-DEgenearte Hybrid Oligonucleotide Primer (CODEHOP) strategy computer program is acessible and is directly linked from the BlockMaker multiple sequence alignment site for hybrid primer prediction beginning with a set of related protein sequences, (see, e.g., Rose (1998) Nucleic Acids Res. 26:1625–1635; Singh (1998) Biotechniques 24:318–319).

Means to synthesize oligonucleotide primer pairs, including degenerate primer pairs, are well known in the art. "Natural" base pairs or synthetic base pairs can be used. For example, use of artificial nucleobases offers a versatile approach to manipulate primer sequence and generate a more complex mixture of amplification products. Various families of artificial nucleobases are capable of assuming multiple hydrogen bonding orientations through internal bond rotations to provide a means for degenerate molecular recognition. Incorporation of these analogs into a single position of a PCR primer allows for generation of a complex library of amplification products. See, e.g., Hoops (1997) Nucleic Acids Res. 25:4866–4871. Nonpolar molecules can also be used to mimic the shape of natural DNA bases. A non-hydrogen-bonding shape mimic for adenine can replicate efficiently and selectively against a nonpolar shape mimic for thymnine (see, e.g., Morales (1998) Nat. Struct. Biol. 5:950954). For example, two degenerate bases can be the pyrimidine base 6H, 8H-3,4-dihydropyrimido[4,5-c][1,2]oxazin-7-one or the purine base N6-methoxy-2,6-diaminopurine (see, e.g., Hill (1998) Proc. Natl. Acad. Sci. USA 95:4258–4263). Exemplary primers of the invention can also incorporate the nucleobase analog 5'-Dimethoxytrityl-N-benzoyl-2'-deoxy-Cytidine, 3'-[(2-cyanoethyl)(N,N-diisopropyl)]-phosphoramidite. This pyrimidine analog hydrogen bonds with purines, including A and G residues.

Generating and Isolating Novel Nucleic Acids Derived From GCA Lesions

The invention provides compositions and methods for identifying the GCA-associated nucleic acids of the invention in biopsies and tissue samples for diagnostic purposes and to identify new GCA associated nucleic acids and polypeptides. In addition using degenerate primers, as described above, subtractive hybridization of nucleic acids from normal tissue against nucleic acids from arteritis tissue samples (e.g., from biopsies) can be used to isolate GCA-associated nucleic acids within the scope of the invention.

The isolation of nucleic acids may be accomplished by a number of techniques, all well known in the art. For instance, oligonucleotide probes (e.g., PCR primers or hybridization probes) based on the sequences disclosed herein can be used to identify desired nucleic acids in a cDNA or a genomic DNA library. To construct genomic libraries, large segments of genomic DNA are generated by random fragmentation, e.g. using restriction endonucleases, and are ligated with vector DNA to form concatemers that can be packaged into the appropriate vector. To prepare a cDNA library, mRNA is isolated (e.g., from a GCA lesion biopsy), and a cDNA library containing sequences encoding GCA-associated polypeptides is prepared from the mRNA. The cDNA or genomic library can then be screened using a probe based upon the sequence of a cloned gene disclosed herein. Probes may be used to hybridize with genomic DNA or cDNA sequences to isolate homologous genes (new GCA associated sequences) or to diagnose GCA. As discussed herein, defined stringent hybridization conditions can be used to identify nucleic acid sequences within the scope of the invention.

Alternatively, antibodies raised against a GCA-associated polypeptide (see below) can be used to screen a cDNA expression library. Alternatively, the nucleic acids of interest can be amplified from nucleic acid samples using amplification techniques.

As noted above, subtractive hybridization of nucleic acid of normal from GCA-involved tissue is another exemplary means of isolating GCA-associated nucleic acid Subtractive hybridization techniques are well known in the an, e.g., as micro-genomic representational difference analysis (RDA); see, e.g., Lisitsyn (1993) Science 259:946–951; Michiels (1998) Nucleic Acids Res. 26:3608–3610; Wan (1996) Nat. Biotechnol. 14:1685–1691; U.S. Pat. Nos. 6,013,437; 5,958,738; 5,935,788; 5,882,874; 5,525,471.

Cloning and Construction of Expression Vectors

The invention provides libraries of expression vectors comprising the GCA polypeptide-encoding sequences of the invention. These nucleic acids may be introduced into a genome or into the cytoplasm or a nucleus of a cell and expressed by a variety of conventional techniques, well described in the scientific and patent literature. See, e.g., Roberts (1987) Nature 328:731; Berger (1987) supra; Schneider (1995) Protein Expr. Purif. 6435:10; Sambrook, Tijssen or Ausubel. Product information from manufacturers of biological reagents and experimental equipment also provide information regarding known biological methods. The vectors can be isolated from natural sources, obtained from such sources as ATCC or GenBank libraries, or prepared by synthetic or recombinant methods.

The nucleic acids of the invention can be expressed in expression cassettes, vectors or viruses which are stably or transiently expressed in cells (e.g., episomal expression systems). Selection markers can be incorporated into expression cassettes and vectors to confer a selectable phenotype on transformed cells and sequences. For example, selection markers can code for episomal maintenance and replication such that integration into the host genome is not required. For example, the marker may encode antibiotic resistance (e.g., chloramphenicol, kanamycin, G418, bleomycin, hygromycin) or herbicide resistance (e.g., chlorosulfuron or Basta) to permit selection of those cells transformed with the desired DNA sequences (see, e.g., Blondelet-Rouault (1997) Gene 190:315–317; Aubrecht (1997) J. Pharmacol. Exp. Ther. 281:992–997). Because selectable marker genes conferring resistance to substrates like neomycin or hygromycin can only be utilfed in tissue culture, chemoresistance genes can be used as selectable markers in vitro and in vivo.

Alignment Analysis of Gene Sequences

The nucleic acid sequences of the invention include genes and gene products identified and characterized by analysis using the exemplary nucleic acid and protein sequences of the invention, including, e.g., the exemplary SEQ ID NO:1 and SEQ ID NO:2; SEQ ID NO:3 and SEQ ID NO:4; SEQ ID NO:5 and SEQ ID NO:6; SEQ ID NO:7 and SEQ ID NO:8, respectively. For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Default program parameters are used unless alternative parameters are designated herein. The sequence comparison algorithm then calculates the percent sequence identity for the test sequence(s) relative to the reference sequence, based on the designated or default program parameters. A "comparison window", as used herein, includes reference to a segment of any one of the number of contiguous positions selected from the group consisting of from 25 to 600, usually about 50 to about 200, more usually about 100 to about 150 in which a sequence may be compared to a reference sequence of the same number of contiguous positions after the two sequences are optimally aligned.

Methods of alignment of sequences for comparison are well-known in the art. Optimal alignment of sequences for comparison can be conducted, e.g., by the local homology algorithm of Smith & Waterman, Adv. Appl. Math. 2:482 (1981), by the homology alignment algorithm of Needleman & Wunsch, J. Mol. Biol. 48:443 (1970), by the search for similarity method of Pearson & Lipman, Proc. Natl. Acad. Sci. USA 85:2444 (1988), by computerized implementations of these algorithms (CLUSTAL, GAP, BESTFIT, FASTA, and TFASTA in the Wisconsin Genetics Software Package, Genetics Computer Group, 575 Science Dr., Madison, Wis.), or by manual alignment and visual inspection.

In a preferred embodiment, CLUSTAL algorithm is used, particularly, the CLUSTAL W program, see, e.g., Thompson (1994) Nuc. Acids Res. 22:4673–4680; Higgins (1996) Methods Enzymol 266:383–402. Variations can also be used, such as CLUSTAL X, see Jeanmougin (1998) Trends Biochem Sci 23:403–405; Thompson (1997) Nucleic Acids Res 25:4876–4882 CLUSTAL is a particularly preferred program for determining if sequences are so substantially identical they are within the scope of the invention because, if a comparison set consists of enough closely related sequences so that the first alignments are accurate, then CLUSTAL W will usually find an alignment that is very close to ideal. In one embodiment, the CLUSTAL W program described by Thompson (1994) supra, is used with the following parameters: K tuple (word) size: 1, window size: 5, scoring method: percentage, number of top diagonals: 5, gap penalty: 3, to determine whether a nucleic acid has sufficient sequence identity to an exemplary nucleic acid (SEQ ID NO:1, 3, 5, or 7) to be with the scope of the invention Another algorithm is PILEUP, which can be used to determine whether a nucleic acid has sufficient sequence identity to SEQ ID NO:1, 3,5, or 7, or SEQ ID NO:9 through SEQ ID NO:14, to be with the scope of the invention. This program creates a multiple sequence alignment from a group of related sequences using progressive, pairwise alignments to show relationship and percent sequence identity. It also plots a tree or dendogram showing the clustering relationships used to create the alignment. PILEUP uses a simplification of the progressive alignment method of Feng & Doolittle, J. Mol. Evol. 35:351–360 (1987). The method used is similar to the method described by Higgins & Sharp, CABIOS 5:151–153 (1989). Using PILEUP, a reference sequence (e.g., an exemplary GCA-associated sequence of the invention) is compared to another sequence to determine the percent sequence identity relationship (i.e., that the second sequence is substantially identical and within the scope of the invention) using the following parameters: default gap weight (3.00), default gap length weight (0.10), and weighted end gaps. In one embodiment, PILEUP obtained from the GCG sequence analysis software package, e.g., version 7.0 (Devereaux (1984) Nuc. Acids Res. 12:387–395), using the parameters described therein, is used to identify nucleic acids within the scope of the invention.

Another example of an algorithm that is suitable for determining percent sequence identity (i.e., substantial similarity or identity) in this invention is the BLAST algorithm, which is described in Altschul (1990) *J. Mol. Biol.* 215:403–410. Software for performing BLAST analyses is publicly available through the National Center for Biotechnology Information. This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul (1990) supra). These initial neighborhood word hits act as seeds for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residues; always >0) and N (penalty score for mismatching residues, always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. In one embodiment, to determine if a nucleic acid sequence is within the scope of the invention, the BLASTN program (for nucleotide sequences) is used incorporating as defaults a wordlength (W) of 11, an expectation (E) of 10, M=5, N=4, and a comparison of both strands. For amino acid sequences, the BLASTP program uses as default parameters a wordlength (W) of 3, an expectation (E) of 10, and the BLOSUM62 scoring matrix (see, e.g., Henikoff (1989) Proc. Natl. Acad. Sci. USA 89:10915).

Exemplary GCA-Associated Nucleic Acids and Polypeptides

The invention provides novel GCA-associated nucleic acids and polypeptides. All possible polypeptides encoded by these nucleic acids are within the scope of the invention, including alterative in-frame ORFs and ORFs read from either strand (e.g., including the complementary strand). For example:

```
>GCA 1a = 1c.T7 cloned sequence of GCA1 and deduced protein sequence

1- GATCCCCGCTTTCGCGGGGATGACAGCGGTACTCAATTCACGCGCAGCGATGCCAGCGAA      -60

61- CTAAACGGAGGATCCCACGAACATCCGCTCCAACCCCGACACCACGCTCCCCGCCGTCAC     -120
       -                                                L  P  A  V  T

121- GACAGGCTCGCTGCCCTCCTCGCGCAAGTTCTTTGCAATCCCTGAGGCCGCGCCCGACAT     -180
       -  T  G  S  L  P  S  S  R  K  F  F  A  I  P  E  A  A  P  D  I

181- CCGCGTTCCCTTGCGCGAGATCATCCTGTCCGAGGGCGCCGGCGAGCCGAACCTGCCGGT     -240
       -  R  V  P  L  R  E  I  I  L  S  E  G  A  G  E  P  N  L  P  V

241- CTATGACACCTCGGGCCCCTACACCGATCCGGCCGTGACGATCGACGTCAACAGCGGCCT     -300
       -  Y  D  T  S  G  P  Y  T  D  P  A  V  T  I  D  V  N  S  G  L

301- GCCGCGCAATCGCCTCGCCTGGGTCAACGAACGCGGCGGCGTCGAGGAATATCAGGCCGC     -360
       -  P  R  N  R  L  A  W  V  K  E  R  G  G  V  E  E  Y  Q  A  A

361- ACCATCAAGCCGGAGGACAACGGCAATGTCGGCGCATCCCACGCCGCCAAGGCGTTCACC     -420
       -  P  S  S  R  R  T  T  SEQ ID NO:2

421- GGCACCACAAGCCGCTGCGCGGCTCGACGGCACAAGATCACCCACTCGAGTTCGCCGCGC     -490

481- CGGCATTATACCAAGGAGATGATCTACCTCGCCGAGCGTGAGAATCTTGGCGCAAGCAGC     -540

541- AGCTGAGCGCGCCGAGGCCGGCTGCCGACGGAAGAGTTTTGGCGCCGCGGTGCCGGCTTA     -600

601- TTACGCCGGAATTTGTCGCAAGAGATCGCGCGGCGGCCATTATTTCCTTTAAAATTAACA     -660

661- TTGCCCAGCTTGAACCGATGAA  -682 SEQ ID NO:1

GCA1a: full length clone

GATCCCCGCTTTCGCGGGGATGACAGCGGTACTCAATTCACGCGCAGCGA                       -50

TGCCAGCGAACTAAACGGAGGATCTCACGAACATCCGCTCCAACCCCGAC                       -100

ACCACGCTCCCCGCCGTCACGACAGGCTCGCTGCCCTCCTCGCGCAAGTT                       -150

CTTTGCAATCCCTGAGGCCGCGCCCGACATCCGCGTTCCCTTGCGCGAGA                       -200

TCATCCTGTCCGAGGGCGCCGGCGAGCCGAACCTGCCGGTCTATGACACC                       -250
```

-continued

```
TCGGGCCCCTACACCGATCCGGCCGTGACGATCGACGTCAACAGCGGCCT        -300
GCCGCGCAATCGCCTCGCCTGGGTCAAGCAACGCGGCGGCGTCGAGGAAT        -350
ATCANGGCCGCACCATCAAGCCGGAGGACAACGGCAATGTCGGCGCATCC        -400
CACGCCGCCAAGGCGTTCACCGNGCACCACAAGCCGCTGCGCGGNCTCGA        -450
CGGCACAAGATCACCCACTCGAGTTCGCCGCGCCGGCATTATACCAAGGA        -500
GATGATCTACGTCGCCGAGCGTGAGAATCTTGGNCGCAAGCAGCAGCTNG        -550
AGCGCGCCGANGGCCGGCTNGCCGACGGNAAGAGTTTTGGCGCCGCGGTG        -600
CCGGNCTTNATTACGCCGGAATTTGTNCGCAANGAGATCGNCGCGGNCGN        -700
GCCATTATTTCCTTTNAAAATTAANCATTGCCGAGCTTGAACCGATGAAN
N -701 (SEQ ID NO:17) SEQ ID NO:1
```

Cloned fragment of GCA 1a used in GCA 1a-GST fusion protein

```
  1- CTCCCCGCCGTCACGACAGGCTCGCTGCCCTCCTCGCGCAAGTTCTTTGCAATCCCTGAG        -60
   - L   P   A   V   T   T   G   S   L   P   S   S   R   K   F   F   A   I   P   E

61- GCCGCGCCCGACATCCGCGTTCCCTTGCGCGAGATCATCCTGTCCGAGGGCGCCGGCGAG       -120
   - A   A   P   D   I   R   V   P   L   R   E   I   I   L   S   E   G   A   G   E

121- CCGAACCTGCCGGTCTATGACACCTCGGGCCCCTACACCGATCCGGCCGTGACGATCGAC       -180
   - P   N   L   P   V   Y   D   T   S   G   P   Y   T   D   P   A   V   T   I   D

181- GTCAACAGCGGCCTGCCGCGCAATCGCCTCGCCTGGGTCAAGGAACGCGGCGGCGTCGAG       -240
   - V   N   S   G   L   P   R   N   R   L   A   W   V   K   E   R   G   G   V   E

241- GAATATCAGGCCGCACCATCAAGCCGGAGGACAACGGC -278
   - E   Y   Q   A   A   P   S   S   R   R   T   T   SEQ ID NO:2
```

>GCA 1b = 1cT3 cloned sequence of GCA1 and deduced protein sequence

```
  1- ACTCTCCAGCCTCTCACCGAGGATGAAGTCGGCTCGTGAAGTGGTTGCGGTCGGGGGCAA        -60
   - L   S   S   L   S   P   R   M   K   S   A   R   E   V   V   A   V   G   G   K

61- AACCCGGGACGAGCTGGCCTTCCTGCCGGCCGCCCTCGAAATTGTCGAGACGCCGCCATC       -120
   - T   R   D   E   L   A   F   L   P   A   A   L   E   I   V   E   T   P   P   S

121- TCCCACCGCGAGACTCACGGCCGCCTTGCTTGCTGCCTTGTTCTACTGCGCCGTGGCGTG       -180
   - P   T   A   R   L   T   A   A   L   L   A   A   L   F   Y   C   A   V   A   W

181- GGCGGGTCTCGGCAGGATCGACATCGTTGCTTCTGCATCCAGAAAGATCGTGCCGGGCGA       -240
   - A   G   L   G   R   I   D   I   V   A   S   A   S   R   K   I   V   P   G   D

241- CCGTGTAAAGCTGGTTCAGCCGCTCGAGGTCGGCGTGGTGCGGGCCACTCATGTCCGCGA       -300
   - R   V   K   L   V   Q   P   L   E   V   G   V   V   R   A   T   M   V   R   D

301- TGGCCAAACCGTCAAGGCCGGCGAGATTCTGATCGAGCTGGATCCATTCGCGGGTGGTGT       -360
   - G   Q   T   V   K   A   G   E   I   L   I   E   L   D   P   F   A   G   G   V

361- GGATGTTGCGCCCCGTCAGAGGTCCATCACGGTGTCGGCGCCCCACGGATCGCCACACCA       -420
   - D   V   A   T   SEQ ID NO:4

421- TCTTGTCGACCTTTCTTCACCGACGAGTCACCGCCGAGTTGCCGATATTGCGTGATCTTA       -480

481- TCAGAATGCGGCGATGATCAT -501 SEQ ID NO:3
```

GCA1b: full length clone

```
ACTCTCCAGCCTCTCACCGAGGATGAAGTCGGCTCGTGAAGTGGTTGCGG       -50
TCGGGGGCAAAACCCGGGACGAGCTGGCCTTCCTGCCGGCCGCCCTCGAA      -100
ATTGTCGAGACGCCGCCATCTCCCACCGCGAGACTCACGGCCGCCTTGCT      -150
TGCTGCCTTGTTCTACTGCGCCGTGGCGTGGGCGGGTCTCGGCAGGATCG      -200
ACATCGTTGCTTCTGCATCCAGAAAGATCGTGCCGGGCCACCGTGTAAAG      -250
CTGGTTCAGCCGCTCGAGGTCGGCGTGGTGCGGGCCACTCATGTCCGCGA      -300
TGGCCAAACCGTCAAGGCCGGCGAGATTCTGATCGAGCTGGATCCATTCG      -350
```

```
                       -continued
CGGGTGGTGTGGATGTTGCGCCCCGTCNAGAGGTCCATCACGGTGTCGGC            -400

GCCCCANCGGATCGCCACACCATCTTGTCGACCTNTTCTTCACCGACGAN            -450

GTCACCGCCGAGTTGCCGATATTGCGNTGATCTTANTCANGAANNTGCGG            -500

NCGATGATCAT -511 (SEQ ID NO:18) SEQ ID NO:3
```

Cloned fragment of GCA 1b used in used in GCA 1b-GST fusion

```
  1- CTCTCCAGCCTCTCACCGAGGATGAAGTCGGCTCGTGAAGTGGTTGCGGTCGGGGCAAA   -60
   - L  S  S  L  S  P  R  N  K  S  A  R  E  V  V  A  V  G  G  K

61- ACCCGGGACGAGCTGGCCTTCCTGCCGGCCGCCCTCGAAATTGTCGAGACGCCGCCATCT -120
      T  R  D  E  L  A  F  L  P  A  A  L  E  I  V  E  T  P  P  S

121- CCCACCGCGAGACTCACGGCCGCCTTGCTTGCTGCCTTGTTCTACTGCGCCGTGGCGTGG -180
      P  T  A  R  L  T  A  A  L  L  A  A  L  F  Y  C  A  V  A  W

181- GCGGGTCTCGGCAGGATCGACATCGTTGCTTCTGCATCCAGAAAGATCGTGCCGGGCGAC -240
      A  G  L  G  R  I  D  I  V  A  S  A  S  R  K  I  V  P  G  D

241- CGTGTAAAGCTGGTTCAGCCGCTCGAGGTCGGCGTGGTGCGGGCCACTCATGTCCGCGAT -300
      R  V  K  L  V  Q  P  L  E  V  G  V  V  R  A  T  H  V  R  D

301- GGCCAAACCGTCAAGGCCGCCGAGATTCTGATCGAGCTGGATCCATTCGCGGGTGGTGTG -360
      G  Q  T  V  K  A  G  E  I  L  I  E  L  D  P  F  A  G  G  V

361- GATGTTGCGC -370
      D  V  A         SEQ ID NO:4
```

>GCA 14 - Cloned Sequence of GCA14 and deduced protein sequence

```
  1- ACCGACGTCGACTATCCATGAACGGATCCCTGCAACGACATCGTGCGTACGGCCTATGAA   -60
  -                  D  P  C  N  D  I  V  R  T  A  Y  E

61- GCGCTCGCCGCCGTGCTCGGTGGCACGCAGTCGCTCCACACCAACTCGTTCGACGAGGCG -120
   - A  L  A  A  V  L  G  G  T  Q  S  L  H  T  N  S  F  D  E  A

121- ATCGCGCTGCCGATTGACTTCTCCGCCCGGATCGCCCGCAACACGAGCTGATCCAGCAGC -180
   - I  A  L  P  I  D  F  S  A  R  I  A  R  N  T  S  *  SEQ ID NO:6

181- ACGAGACAGACGTCACGGACGCGGTCGACACTCTGGCGGGGTCCTACTACGTGGAGCGCC -240

241- TGACGGATGACCTCGCCAAGCGGGCCTGGGAGCTGATGGAAGAGGTCGAGAAGATGGGTG -300

301- GCATGGCGCAGGCGATCGCGACCGGTTGGCCGAAGCGCCTGATCGAGCAATCTGCGACGC -360

361- AAAAGCAGGCCGCGATCGATCGCGGCGATCAGGTGATCGTGGGCGTGAACCGCTACCGGC -420

421- CCGAACAGGAGCAACCGATCGACATTATTGAGATCGACAACTCGACGCTTCGGGCCTCCC -480

481- AGATCCGGTGTCTCGCCGAAATCGAAAAGGCGCGTGATTCAAGGAAGGTTGAGTCCGCGC -540

541- TCGGGGAGCTGGCGTGTATTGCCCGCACGCGTGAGGGAAATCTGCTGGCTGCAGCGACCG -600

601- AGCCCGCTCGCGCGCGGGCTACCGTCGGGGAGATGTCCGACGCCATGCGGCAAGCATTCG -660

661- GCGACCACGAGGCGGTGCCGGAGGTAGTGTCGGACGTTTACGGCCGTGCCTATGGCACGG -720

721- ATCCGTTCATGGATACTCGACGTCGGT -747 SEQ ID NO:5
```

Cloned fragment of GCA14 used in GCA 14-GST fusion

```
  1- GATCCCTGCAACGACATCGTGCGTACGGCCTATGAAGCGCTCGCCGCCGTGCTCGGTGGC   -60
   - D  P  C  N  D  I  V  R  T  A  Y  E  A  L  A  A  V  L  G  G

61- ACGCAGTCGCTCCACACCAACTCGTTCGACGAGGCGATCGCGCTGCCGATTGACTTCTCC -120
   - T  Q  S  L  H  T  N  S  F  D  E  A  I  A  L  P  I  D  F  S

121- GCCCGGATCGCCCGCAACACCAGCTGAATCTCCAGCAGCACGAGACAGACGTCACGGACG -180
   - A  R  I  A  R  N  T  S  *  SEQ ID NO:6

181- CGGTCGACACTCTGGCGGGGTCCTACTACGTGGAGCGCCTGACGGATGACCTCGCCAAGC -240

241- GGGCCTGGGAGCTGATGGAAGAGGTCGAGAAGATGGGTGGCATGGCGCAGGCGATCGCGA -300

301- CCGGTTGGCCGAAGCGCCTGATCGAGCAATCTGCGACGCAAAAGCAGGCCGCGATCGATC -360

361- GCGGCGATCAGGTGATCGTGGGCGTGAACCGCTACCGGCCCGAACAGGAGCAACCGATCG -420
```

-continued

```
421- ACATTATTGAGATCGACAACTCGACGGTTCGGGCCTCCCAGATCCGGTGTCTCGCCGAAA   -480

481- TCGAAAAGGCGCGTGATTCAAGGAAGGTTGAGTCC -515 SEQ ID NO:5
```

GCA17 cloned total sequence and deduced protein sequence

```
  1- ACTCTCCAGCCTCTCACCGAGGATCATCGACGACATTAAGCAGCTGGCCGACAACGGCGT   -60
   -                I  I  D  D  I  K  Q  L  A  D  N  G  V

61- GCGCGAATTCACGCTGATCGGACAGAATGTCAACGCCTACCACGGCGGAGGGCCCGACGG   -120
   -  R  E  F  T  L  I  G  Q  N  V  N  A  Y  H  G  G  G  P  D  G

121- CCGCGTCTGGCCGCTCGGCAAATTGCTGCAGCGACTCGCGGACATTCCAGGCGTCATGCG   -190
   -  R  V  W  P  L  G  K  L  L  Q  R  L  A  D  I  P  G  V  M  R

181- GCTGCGTTATTCGATCAGCCATCCGCGCGACGTCGACGACAGCCTGATCGCCGCGCATCG   -240
   -  L  R  Y  S  I  S  H  P  R  D  V  D  D  S  L  I  A  A  H  R

241- CGATTTGCCCGGACTGATGCCGGTCGTGCACCTGCCGGTGCAATCGGGGGCGGACCGGAT   -301
   -  D  L  P  G  L  M  P  F  V  H  L  P  V  Q  S  G  A  D   SEQ ID NO:8

301- C -301 SEQ ID NO:7
```

Cloned fragment of GCA17 used in GCA17-GST Fusion protein

```
  1- ATCATCGACGACATTAAGCAGCTGGCCGACAACGGCGTGCGCGAATTCACGCTGATCGGA   -60
   -  I  I  D  D  I  K  Q  L  A  D  N  G  V  R  E  F  T  L  I  G

61- CAGAATGTCAACGCCTACCACGGCGGAGGGCCCGACGGCCGCGTCTGGCCGCTCGGCAAA   -120
   -  Q  N  V  N  A  Y  H  G  G  G  P  D  G  R  V  W  P  L  G  K

121- TTGCTGCAGCGACTCGGGGACATTCCAGGCGTCATGCGGCTGGGTTATTCGATGAGCCAT   -180
   -  L  L  Q  R  L  A  D  I  P  G  V  M  R  L  R  Y  S  I  S  H

181- CCGCGCGACGTCGACGACAGCCTGATCGCCGCGCATCGCGATTTGCCCGGACTGATGCCG   -240
   -  P  R  D  V  D  D  S  L  I  A  A  H  R  D  L  P  G  L  M  P

241- TTCGTGCACCTGCCGGTGCAATCGGGGGCGGACCG -275 SEQ ID NO:7
   -  F  V  H  L  P  V  Q  S  G  A  D     SEQ ID NO:8
```

GCA2a

```
ACTCTCCANCCTCTCACCGAGGATCAGAATAGGTGAAGAGCGAAGACACC              -50

GAGAACGTCTGGCCTTGAACGGACAGCGTGCTTGAGTTGGTCGGGGTCAC              -100

CACCGGACCCGTGTCCACCGGCGCAGTCACNGTGAAAGCACTTGACCATG              -150

ATCCCAGACGGTGCCGTCATCCGCGCGGACCCACANCGTNTCCGCGCCCG              -200

ACCGGATTGATAGCICAGCGACACCAGCTGGGCTGCCGTGACGTANTTGT              -250

GCTGGTTNGGTGCAAGTGCCACCCCGCTCAAGACAAANTGGCCGCACCTG              -300

TGCCCGTGTCCCAAACGTCATATTGGGTCGCAGCACTGTCGAACGGATCA              -350

CTGTANGTGCACAGCGACNAANCCGCATANCTCTNGCCGTGGGGCGCAAC              -400

GATGTTNNACACCGTCTCAACGGGTACCGTGTCNAGGGGANCATTTACNG              -450

GGAAAGCATTCGACCACTCCCCCACACCGTGCCCGCATTTGCGCCGATTC              -500

CTTTCATTGATATGTCCACGTCGGTNGGNCTTTAAGCNGGCGGCAACCGC              -550

GGTGNAGCTNCACTTTTTGTTCCTTTTATTGANGGTTAATTTGCGCGCTT              -600

TGGNCGTAANTNTTTGAAN -620 SEQ ID NO:9
```

5'3' GCA2a Frame 1

```
actctccancctctcaccgaggateagaataggtgaagagcgaagacaccgagaacgtct
  T  L  X  P  L  T  E  D  Q  N  R  -  R  A  K  T  P  R  T  S ggccttgaacggacagcgtgcttgagttggtcggggtcaccaccggacccgtgtccaccg
  G  L  E  R  T  A  C  L  S  W  S  G  S  P  P  D  P  C  P  P gcgcagtcacngtgaaagcacttgaccatgatcccagacggtgccgtcatccgcgcggac
  A  Q  S  X  -  K  H  L  T  M  I  P  D  G  A  V  I  R  A  D
```

-continued

```
ccacancgtntccgcgcccgaccggattgatagctcagcgacaccagctgggctgccgtg
 P  X  R  X  R  A  R  P  D  -  -  L  S  D  T  S  W  A  A  V acgtanttgtgctggttnggtgcaagtgccaccccgctcaagacaaantggccgcacctg
 T  X  L  C  W  X  G  A  S  A  T  P  L  K  T  X  W  P  H  L tgcccgtgtcccaaacgtcatattgggtcgcagcactgtcgaacggatcactgtangtgc
 C  P  C  P  K  R  H  I  G  S  Q  H  C  R  T  D  H  C  X  C acagcgacnaanccgcatanctctngccgtggggcgcaacgatgttnnacaccgtctcaa
 T  A  X  X  P  H  X  S  X  R  G  A  Q  R  C  X  T  P  S  Q cgggtaccgtgtcnaggggancatttacngggaaagcattcgaccactcccccacaccgt
 R  V  P  C  X  G  X  H  L  X  G  K  H  S  T  T  P  P  H  R gcccgcatttgcgccgattcctttcattgatatgtccacgtcggtnggnctttaagcngg
 A  R  I  C  A  D  S  F  H  -  Y  V  H  V  G  X  X  L  S  X cggcaaccgcggtgnagctncacttttgttccttttattgangggttaatttgcgcgctt
 R  Q  P  R  X  S  X  T  F  C  S  F  Y  -  X  L  I  C  A  L tggncgtaantntttngaan (SEQ ID NO:19)
 W  X  -  X  F  X  X  (SEQ ID NO:20)
```

5'3' GCA2a Frame 2

```
actctccancctctcaccgaggatcagaataggtgaagagcgaagacaccgagaacgtctg
  L  S  X  L  S  P  R  I  R  I  G  E  E  R  R  H  R  E  R  L gccttgaacggacagcgtgcttgagttggtcggggtcaccaccggacccgtgtccaccgg
  A  L  N  G  Q  R  A  -  V  G  R  G  H  H  R  T  R  V  H  R cgcagtcacngtgaaagcacttgaccatgatcccagacggtgccgtcatccgcgcggacc
  R  S  H  X  E  S  T  -  P  -  S  Q  T  V  P  S  S  A  R  T cacancgtntccgcgcccgaccggattgatagctcagcgacaccagctgggctgccgtga
  H  X  X  S  A  P  D  R  I  D  S  S  A  T  P  A  G  L  P  - cgtanttgtgctggttnggtgcaagtgccaccccgctcaagacaaantggccgcacctgt
  R  X  C  A  G  X  V  Q  V  P  P  R  S  R  Q  X  G  R  T  C gcccgtgtcccaaacgtcatattgggtcgcagcactgtcgaacggatcactgtangtgca
  A  R  V  P  N  V  I  L  G  R  S  T  V  E  R  I  T  V  X  A cagcgacnaagccgcatanctctngccgtggggcgcaacgatgttnnacaccgtctcaac
  Q  R  X  X  R  I  X  X  A  V  G  R  N  D  V  X  H  R  L  N gggtaccgtgtcnaggggancatttacngggaaagcattcgaccactcccccacaccgtg
  G  Y  R  V  X  G  X  I  Y  X  E  S  I  R  P  L  P  H  T  V cccgcatttgcgccgattcctttcattgatatgtccacgtcggtnggncttaagcnggc
  P  A  F  A  P  I  P  F  I  D  M  S  T  S  X  X  L  -  X  G ggcaaccgcggtgnagctncacttttgttccttttattgangggttaatttgcgcgcttt
  G  N  R  G  X  A  X  L  F  V  P  F  I  X  G  -  F  A  R  F ggncgtaantntttngaan (SEQ ID NO:21)
  X  R  X  X  X  E  X  (SEQ ID NO:22)
```

5'3' GCA2a Frame 3

```
actctccancctctcaccgaggatcagaataggtgaagagcgaagacaccgagaacgtctgg
   S  P  X  S  H  R  G  S  E  -  V  K  S  E  D  T  E  N  V  W ccttgaacggacagcgtgcttgagttggtcggggtcaccaccggacccgtgtccaccggc
  P  -  T  D  S  V  L  E  L  V  G  V  T  T  G  P  V  S  T  G gcagtcacngtgaaagcacttgaccatgatcccagacggtgccgtcatccgcgcggaccc
  A  V  X  V  K  A  L  D  H  D  P  R  R  C  R  H  P  R  G  P acancgtntccgcgcccgaccggattgatagctcagcgacaccagctgggctgccgtgac
  T  X  X  P  R  P  T  G  L  I  A  Q  R  H  Q  L  G  C  R  D gtanttgtgctggttnggtgcaagtgccaccccgctcaagacaaantggccgcacctgtg
  V  X  V  L  V  X  C  K  C  H  P  A  Q  D  K  X  A  A  P  V cccgtgtcccaaacgtcatattgggtcgcagcactgtcgaacggatcactgtangtgcac
  P  V  S  Q  T  S  Y  W  V  A  A  L  S  N  G  S  L  X  V  H agcgacnaanccgcatanctctngccgtggggcgcaacgatgttnnacaccgtctcaacg
```

-continued

```
                      S  D  X  X  A  X  L  X  P  W  G  A  T  N  X  X  T  V  S  T ggtaccgtgtcnagggancatttacngggaaagcattcgaccactcccccacaccgtgc
 G  T  V  X  R  G  X  F  X  G  K  A  F  D  H  S  P  T  P  C ccgcatttgcgccgattccttcattgatatgtccacgtcggtnggnctttaagcnggcg
 P  H  L  R  R  F  L  S  L  I  C  P  R  R  X  X  F  K  K  A gcaaccgcggtgnagctncactttttgttccttttattganggttaatttgcgcgctttg
 A  T  A  V  X  X  H  F  L  F  L  L  L  X  V  N  L  R  A  L gncgtaantntttngaan (SEQ ID NO:23)
 X  V  X  X  X  X  (SEQ ID NO:24)

3'5' GCA2a Frame 1 nttcnaaanantttacgnccaaagcgcgcaaattaaccntcaataaaaggaacaaaaagtg
 X  X  X  X  Y  X  Q  S  A  Q  I  N  X  Q  -  K  E  Q  K  V nagctncaccgcggttgccgccngcttaaagnccaccgacgtggacatatcaatgaaag
 X  X  H  R  G  C  R  X  L  K  X  X  P  T  W  T  Y  Q  -  K gaatcggcgcaaatgcgggcacggtgtggggagtggtcgaatgctttcccngtaaatgn
 E  S  A  Q  N  R  A  R  C  G  G  V  V  E  C  F  P  X  K  X tccccctngacacggtacccgttgagacggtgtnnaacatcgttgcgccccacggcnagag
 S  P  X  H  G  T  R  -  D  G  X  X  H  R  C  A  P  R  X  E ntatgcggnttngtcgctgtgcacntacagtgatccgttcgacagtgctgcgacccaata
 X  C  X  X  V  A  V  H  X  Q  -  S  V  R  Q  C  C  D  P  I tgacgtttgggacacgggcacaggtgcggccantttgtcttgagcggggtggcacttgca
 -  R  L  G  H  G  H  R  C  G  X  F  V  L  S  G  V  A  L  A ccnaaccagcacaantacgtcacggcagcccagctggtgtcgctgagctatcaatccggt
 X  N  Q  H  X  Y  V  T  A  A  Q  L  V  S  L  S  Y  Q  S  G cgggcgcgganacgntgtgggtccgcgcggatgacggcaccgtctgggatcatggtcaag
 R  A  R  X  X  C  G  S  A  R  M  T  A  P  S  G  I  M  V  K tgctttcacngtgactgcgccggtggacacgggtccggtggtaccccgaccaactcaag
 C  F  H  X  D  C  A  G  G  H  G  S  G  G  D  P  D  Q  L  K cacgctgtccgttcaaggccagacgttctcggtgtcttcgctcttcacctattctgatcc
 H  A  V  R  S  R  P  D  V  L  G  V  F  A  L  H  L  F  -  S tcggtgagaggntggagagt (SEQ ID NO:25)
 S  V  R  X  W  R  (SEQ ID NO:26)

3'5' GCA2a Frame 2 nttcnaaanantttacgnccaaagcgcgcaaattaaccntcaataaaaggaacaaaaagtgn
  F  X  X  X  T  X  K  A  R  K  L  T  X  N  K  R  N  K  K  X agctncaccgcggttgccgccngcttaaagnccaccgacgtggacatatcaatgaaagg
 S  X  T  A  V  A  A  X  L  K  X  X  R  R  G  H  I  N  E  R aatcggcgcaaatgcgggcacggtgtggggagtggtcgaatgctttcccngtaaatgnt
 N  R  R  K  C  G  H  G  V  G  E  W  S  N  A  F  X  V  N  X cccctngacacggtacccgttgagacggtgtnnaacatcgttgcgccccacggcnagagn
 P  X  D  T  V  P  V  E  T  V  X  N  I  V  A  P  H  G  X  X tatgcggnttngtcgctgtgcacntacagtgatccgttcgacagtgctgcgacccaatat
 Y  A  X  X  S  L  C  X  Y  S  D  P  F  D  S  A  A  T  Q  Y gacgtttgggacacgggcacaggtgcggccantttgtcttgagcggggtggcacttgcac
 D  V  W  D  T  G  T  G  A  A  X  L  S  -  A  G  W  H  L  H cnaaccagcacaantacgtcacggcagcccagctggtgtcgctgagctatcaatccggtc
 X  T  S  T  X  T  S  R  Q  P  S  W  C  R  -  A  I  N  P  V gggcgcgganacgntgtgggtccgcgcggatgacggcaccgtctgggatcatggtcaagt
 G  R  G  X  X  V  G  P  R  G  -  R  H  R  L  G  S  W  S  S gctttcacngtgactgcgccggtggacacgggtccggtggtgaccccgaccaactcaagc
 A  F  X  V  T  A  P  V  D  T  G  P  V  V  T  P  T  N  S  S acgctgtccgttcaaggccagacgttctcggtgtcttcgctcttcacctattctgatcct
 T  L  S  V  Q  G  Q  T  F  S  V  S  S  L  F  T  Y  S  D  P
```

-continued

```
cggtgagaggntggagagt
 R  -  E  X  G  E  (SEQ ID NO:27)
```

3'5' GCA2a Frame 3

```
nttcnaaanantacgnccaaagcgcgcaaattaaccntcaataaaaggaacaaaaagtgna
  X  K  X  L  X  P  K  R  A  N  -  X  S  I  K  G  T  K  S  X gctncaccgcggttgccgccngcttaaagnccnaccgacgtggacatatcaatgaaagga
 A  X  P  R  L  P  X  A  -  X  X  T  D  V  D  I  S  M  K  G atcggcgcaaatgcgggcacggtgtggggagtggtcgaatgctttcccngtaaatgntc
 I  G  A  N  A  G  T  V  W  G  S  G  R  M  L  S  X  -  M  X ccctngacacggtacccgttgagacggtgtnnaacatcgttgcgccccacggcnagagnt
 P  X  T  R  Y  P  L  R  R  C  X  T  S  L  R  F  T  X  R  X atgcggnttngtcgctgtgcacntacagtgatccgttcgacagtgctgcgacccaatatg
 M  R  X  X  R  C  A  X  T  V  I  R  S  T  V  L  R  P  N  M acgtttgggacacgggcacaggtgcggccantttgtcttgagcggggtggcacttgcacc
 T  F  G  T  R  A  Q  V  R  P  X  C  L  E  R  G  G  T  C  T naaccagcacaantacgtcacggcagcccagctggtgtcgctgagctatcaatccggtcg
 X  P  A  Q  X  R  K  G  S  P  A  G  V  A  E  L  S  I  R  S ggcgcgganacgntgtgggtccgcgcggatgacggcaccgtctgggatcatggtcaagtg
 G  A  X  T  X  W  V  R  A  D  D  G  T  V  W  D  H  G  Q  V ctttcacngtgactgcgccggtggacacgggtccggtggtgaccccgaccaactcaagca
 L  S  X  -  L  R  R  W  T  R  V  R  W  -  P  R  P  T  Q  A cgctgtccgttcaaggccagacgttctcggtgtcttcgctcttcacctattctgatcctc
 R  C  P  F  K  A  R  R  S  R  C  L  R  S  S  P  I  L  I  L ggtgagaggntggagagt
 G  E  R  X  E  S  (SEQ ID NO:28)
```

GCA3b

| | |
|---|---|
| GATCCGACCAGCAATCAGGCGGAGCTGCAGCACCTGAAAAACGACCTTCT | -50 |
| CTCGGCACTGCTGGGTATTTCACGCAACCGCTCTGCGCTTGGCGGGAAAC | -100 |
| ACCGACGCGCTTGAAGGCTTACCGGACGACACGCCGCCAGCCTTGATTCG | -150 |
| AATGCATCTGGAGTACTTGCGCAGTCAGGATTCCGAGCAGCGCGCCAAGC | -200 |
| TGTCCGAACTGGATCAGCAACGGGTGCAGAAGGTCGCGGAGACCAGGACG | -250 |
| ATCGACGCCAGCATCGCGAAGATTGAAGCTTTGCTGCGGTGCTGCAGGAN | -300 |
| CGGGTCGGGGTTCGCAAGTACCTGGCGGACAGGGAGTACGGCTCAAAGCT | -350 |
| GCAATATTCGCAGGAACTCCAGGAACTGGTCGGGATGCAGCAGGACATCC | -400 |
| TGGTGCAACGGAGCAAAGCTCGAGGAAACCAATGCGGNTTGTCGCCGCAC | -450 |
| TTCGACGAAAACCCGCGGNAAGCTTCGTCTNNGAATAACCGGCACCCGNC | -500 |
| TGTTCCNACGATCTTGGCCCAAGGGGACGCAAAAAAGGGCCGGCAAGNCC | -550 |
| TCAAAGGACCAAGGGMGTTTTAAAANCCGAGCACCCGGGACCCAACCTTT | -600 |
| AAAAANCNTTGGCGGCCCCCATTGGACGGNGTGGNGGCAACAAATTGGGC | -650 |

CGNGCCCCATTT -662 SEQ ID NO:10

5'3' GCA3b Frame 1

```
gatccgaccagcaatcaggcggagctgcagcacctgaaaaacgaccttctctcggcactg
 D  P  T  S  N  Q  A  E  L  Q  H  L  K  N  D  L  L  S  A  L ctgggtatttcacgcaaccgctctgcgcttggcgggaaacaccgacgcgcttgaaggctt
 L  G  I  S  R  N  R  S  A  L  G  G  K  H  R  R  A  -  R  L accggacgacacgccgccagccttgattcgaatgcatctggagtacttgcgcagtcagga
 T  G  R  H  A  A  S  L  D  S  N  A  S  G  V  L  A  Q  S  G
```

-continued

```
ttccgagcagcgcgccaagctgtccgaactggatcagcaacgggtgcagaaggtcgcgga
 F  R  A  A  R  Q  A  V  R  T  G  S  A  T  G  A  E  G  R  G gaccaggacgatcgacgccagcatcgcgaagattgaagctttgctgcggtgctgcaggan
 D  Q  D  D  R  R  Q  H  R  E  D  -  S  F  A  A  V  L  Q  X cgggtcggggttcgcaagtacctggcggacagggagtacggctcaaagctgcaatattcg
 R  V  G  V  R  K  Y  L  A  D  R  E  Y  G  S  K  L  Q  Y  S caggaactccaggaactggtcgggatgcagcaggacatcctggtgcaacggagcaaagct
 Q  E  L  Q  E  L  V  G  M  Q  Q  D  I  L  V  Q  R  S  K  A cgaggaaaccaatgcggnttgtcgccgcacttcgacgaaaacccgcggnaagcttcgtct
 R  G  N  Q  C  X  L  S  P  H  F  D  E  N  P  R  X  A  S  S nngaataaccggcacccgnctgttccnacgatcttggcccaaggggacgcaaaaaagggc
 X  N  N  R  H  P  X  V  X  T  I  L  A  Q  G  D  A  K  K  G cggcaagncctcaaaggaccaagggngttttaaaanccgagcacccgggacccaacccttt
 R  Q  X  L  K  G  P  R  X  F  -  X  P  S  T  R  D  P  T  F aaaaancnttggcggcccccattcgacggngtggnggcaacaaattgggccgngccccat
 K  X  X  W  R  P  P  F  D  X  V  X  A  T  N  W  A  X  P  H  (SEQ ID NO:30)

tt (SEQ ID NO:29)

5'3' GCA3b Frame 2 gatccgaccagcaatcaggcggagctgcagcacctgaaaaacgaccttctctcggcactgc
  I  R  P  A  I  R  R  S  C  S  T  -  K  T  T  F  S  R  H  C tgggtatttcacgcaaccgctctgcgcttggcgggaaacaccgacgcgcttgaaggctta
 W  V  F  H  A  T  A  L  R  L  A  G  N  T  D  A  L  E  G  L ccggacgacacgccgccagccttgattcgaatgcatctggagtacttgcgcagtcaggat
 P  D  D  T  P  P  A  L  I  R  M  H  L  E  Y  L  R  S  Q  D tccgagcagcgcgccaagctgtccgaactggatcagcaacgggtgcagaaggtcgcggag
 S  E  Q  R  A  K  L  S  E  L  D  Q  Q  R  V  Q  K  V  A  E accaggacgatcgacgccagcatcgcgaagattgaagctttgctgcggtgctgcagganc
 T  R  T  I  D  A  S  I  A  K  I  E  A  L  L  R  C  C  R  X gggtcggggttcgcaagtacctggcggacagggagtacggctcaaagctgcaatattcgc
 G  S  G  F  A  S  T  W  R  T  G  S  T  A  Q  S  C  N  I  R aggaactccaggaactggtcgggatgcagcaggacatcctggtgcaacggagcaaagctc
 R  N  S  R  N  W  S  G  C  S  R  T  S  W  C  N  G  A  K  L gaggaaaccaatgcggnttgtcgccgcacttcgacgaaaacccgcggnaagcttcgtctn
 E  E  T  N  A  X  C  R  R  T  S  T  K  T  R  X  K  L  R  X ngaataaccggcacccgnctgttccnacgatcttggcccaaggggacgcaaaaaagggcc
 X  I  T  G  T  X  L  F  X  R  S  W  P  K  G  T  Q  K  R  A ggcaagncctcaaaggaccaagggngttttaaaanccgagcacccgggacccaaccttta
 G  K  X  S  K  D  Q  G  X  F  K  X  R  A  P  G  T  Q  P  L aaaancnttggcggcccccattcgacggngtggnggcaacaaattgggccgngccccatt
 K  X  X  G  G  P  H  S  T  X  W  X  Q  Q  I  G  P  X  P  I  (SEQ ID NO:32)

t (SEQ ID NO:31)

5'3' GCA3b Frame 3 gatccgaccagcaatcaggcggagctgcagcacctgaaaaacgaccttctctcggcactgct
  S  D  Q  Q  S  G  G  A  A  A  P  E  K  R  P  S  L  G  T  A gggtatttcacgcaaccgctctgcgcttggcgggaaacaccgacgcgcttgaaggcttac
 G  Y  F  T  Q  P  L  C  A  W  R  E  T  P  T  R  L  K  A  Y cggacgacacgccgccagccttgattcgaatgcatctggagtacttgcgcagtcaggatt
 R  T  T  R  Q  P  -  F  E  C  I  W  S  T  C  A  V  R  I ccgagcagcgcgccaagctgtccgaactggatcagcaacgggtgcagaaggtcgcggaga
 P  S  S  A  P  S  C  P  N  W  I  S  N  G  C  R  R  S  R  R ccaggacgatcgacgccagcatcgcgaagattgaagctttgctgcggtgctgcaggancg
 P  G  R  S  T  P  A  S  R  R  L  K  L  C  C  G  A  A  G  X
```

-continued

```
ggtcggggttcgcaagtacctggcggacagggagtacggctcaaagctgcaatattcgca
 G  R  G  S  Q  V  P  G  Q  Q  G  V  R  L  K  A  A  I  F  A ggaactccaggaactggtcgggatgcagcaggacatcctggtgcaacggagcaaagctcg
 G  T  P  G  T  G  R  D  A  A  G  H  P  G  A  T  E  Q  S  S aggaaaccaatgcggnttgtcgccgcacttcgacgaaaacccgcggnaagcttcgtctnn
 R  K  P  M  R  X  V  A  A  L  R  R  K  P  A  X  S  F  V  X gaataaccggcacccgnctgttccnacgatcttggcccaaggggacgcaaaaaagggccg
 E  -  P  A  P  X  C  S  X  D  L  G  P  R  G  R  K  K  G  P gcaagncctcaaaggaccaagggngttttaaaanccgagcacccgggacccaacctttaa
 A  X  P  Q  R  T  K  X  V  L  K  X  E  H  P  G  P  N  L  - aaaacnttggcggcccccattcgacgggntggnggcaacaaattgggccgngccccattt (SEQ ID NO:33)
 K  X  L  A  A  P  I  R  R  X  X  G  N  K  L  G  X  A  P  F (SEQ ID NO:34)
```

3'5' GCA3b Frame 1

```
aaatggggcncggcccaatttgttgccnccacnccgtcgaatgggggccgccaangnttt
 K  W  G  X  A  Q  F  V  A  X  X  P  S  N  G  G  R  Q  X  P ttaaaggttgggtcccgggtgctcggnttttaaaacnccttggtcctttgaggncttgc
 L  K  V  G  S  R  V  L  X  F  -  N  X  L  G  P  L  R  X  C cggcccttttttgcgtcccttgggccaagatcgtnggaacagncgggtgccggttattc
 R  P  F  F  A  S  P  W  A  K  I  X  G  T  X  G  C  R  L  F nnagacgaagcttnccgcgggttttcgtcgaagtgcggcgacaaxccgcattggtttcct
 X  D  E  A  X  R  G  F  S  S  K  C  G  D  X  P  H  W  F  P cgagctttgctccgttgcaccaggatgtcctgctgcatcccgaccagttcctggagttcc
 R  A  L  L  R  C  T  R  M  S  C  C  I  P  T  S  S  W  S  S tgcgaatattgcagctttgagccgtactccctgtccgccaggtacttgcgaaccccgacc
 C  E  Y  C  S  F  E  P  Y  S  L  S  A  R  Y  L  R  T  P  T cgntcctgcagcaccgcagcaaagcttcaatcttcgcgatgctggcgtcgatcgtcctgg
 X  S  C  S  T  A  A  K  L  Q  S  S  R  C  W  R  R  S  S  W tctccgcgaccttctgcacccgttgctgatccagttcggacagcttggcgcgctgctcgg
 S  P  R  P  S  A  P  V  A  D  P  V  R  T  A  W  R  A  A  R aatcctgactgcgcaagtactccagatgcattcgaatcaaggctggcggcgtgtcgtccg
 N  P  D  C  A  S  T  P  D  A  F  E  S  R  L  A  A  C  R  P gtaagccttcaagcgcgtcggtgtttccgccaagcgcagagcggttgcgtgaaatacc
 V  S  L  Q  A  R  R  C  F  P  P  S  A  E  R  L  R  E  I  P agcagtgccgagagaaggtcgttttcaggtgctgcagctccgcctgattgctggtcgga
 S  S  A  E  R  R  S  P  F  R  C  C  S  S  A  -  L  L  V  G (SEQ ID NO:36)

tc (SEQ ID NO:35)
```

3'5' GCA3b Frame 2

```
aaatggggcncggcccaatttgttgccnccacnccgtcgaatgggggccgccaangnttt
  N  G  X  R  P  N  L  L  X  P  X  R  R  M  G  A  A  X  X  F taaaggttgggtcccgggtgctcggnttttaaaacnccttggtcctttgaggncttgcc
  -  R  L  G  P  G  C  S  X  F  K  X  P  L  V  L  -  X  L  A ggcccttttttgcgtcccttgggceaagatcgtnggaacagncgggtgccggttattcn
  G  P  F  L  R  P  L  G  P  R  S  X  E  Q  X  G  A  G  Y  X nagacgaagcttnccgcgggttttcgtcgaagtgcggcgacaanccgcattggtttcctc
  X  T  K  L  X  A  G  F  R  R  S  A  A  T  X  R  I  G  F  L gagctttgctccgttgcaccaggatgtcctgctgcatcccgaccagttcctggagttcct
  E  L  C  S  V  A  P  G  C  P  A  A  S  R  P  V  P  G  V  P gcgaatattgcagctttgagccgtactccctgtccgccaggtacttgcgaaccccgaccc
  A  N  I  A  A  L  S  R  T  P  C  P  P  G  T  C  E  P  R  P gntcctgcagcaccgcagcaaagcttcaatcttcgcgatgctggcgtcgatcgtcctggt
  X  P  A  A  P  Q  Q  S  F  N  L  R  D  A  G  V  D  R  P  G ctccgcgaccttctgcacccgttgctgatccagttcggacagcttggcgcgctgctcgga
  L  R  D  L  L  H  P  L  L  I  Q  F  G  Q  L  G  A  L  L  G
```

-continued

```
atcctgactgcgcaagtactccagatgcattcgaatcaaggctggcggcgtgtcgtccgg
 I  L  T  A  Q  V  L  Q  N  N  S  N  Q  G  W  R  R  V  V  R taagccttcaagcgcgtcggtgtttcccgccaagcgcagagcggttgcgtgaaataccca
 -  A  F  K  R  V  G  V  S  R  Q  A  Q  S  G  C  V  K  Y  P gcagtgccgagagaaggtcgttttcaggtgctgcagctccgcctgattgctggtcggat
 A  V  P  R  E  G  R  F  S  G  A  A  A  P  P  D  C  W  S  D  (SEQ ID NO:37)

c

3'5' GCA3b Frame 3 aaatggggcncggcccaatttgttgccnccacnccgtcgaatgggggccgccaangnttttt
  M  G  X  G  P  I  C  C  X  H  X  V  E  W  G  P  P  X  X  F aaaggttgggtcccgggtgctcggnttttaaaacncccttggtcctttgaggncttccg
 K  G  W  V  P  G  A  R  X  L  K  X  P  W  S  F  E  X  L  P gcccttttttgcgtccccttgggccaagatcgtnggaacagncgggtgccggttattcnn
 A  L  F  C  V  P  L  G  Q  D  R  X  N  X  R  V  P  V  I  X agacgaagcttnccgcgggttttcgtcgaagtgcggcgacaanccgcattggtttcctcg
 R  R  S  X  P  R  V  F  V  E  V  R  R  Q  X  A  L  V  S  S agctttgctccgttgcaccaggatgtcctgctgcatcccgaccagttcctggagttcctg
 S  F  A  P  L  H  Q  D  V  L  L  H  P  D  Q  F  L  E  F  L cgaatattgcagctttgagccgtactccctgtccgccaggtacttgcgaaccccgacccg
 R  I  L  Q  L  -  A  V  L  P  V  R  Q  V  L  A  N  P  D  P ntcctgcagcaccgcagcaaagcttcaatcttcgcgatgctggcgtcgatcgtcctggtc
 X  L  Q  H  R  S  K  A  S  I  F  A  M  L  A  S  I  V  L  V tccgcgaccttctgcacccgttgctgatccagttcggacagcttggcgcgctgctcggaa
 S  A  T  F  C  T  R  C  -  S  S  S  D  S  L  A  R  C  S  E tcctgactgcgcaagtactccagatgcattcgaatcaaggctggcggcgtgtcgtccggt
 S  -  L  R  K  Y  S  R  C  I  R  I  K  A  G  G  V  S  S  G aagccttcaagcgcgtcggtgtttccgccaagcgcagagcggttgcgtgaaatacccag
 K  P  S  S  A  S  V  F  P  A  K  R  R  A  V  A  -  N  T  Q cagtgccgagagaaggtcgttttcaggtgctgcagctccgcctgattgctggtcggatc
 Q  C  R  E  K  V  V  F  Q  V  L  Q  L  R  L  I  A  G  R  I  (SEQ ID NO:38)

GCA4

ACTCTCNNGCCTCTCACCGAAGATAGCCGGCAAGGACTGGCGNGAACANN               -50

GCGCGCTGGACTATCNCTAAAGGGTCTCCNACNACGTCCANCCGGACNAG              -100

CTGACCTCGTTTCCNCNAAGCGTGAAACTGAAGGCCGGTGAAACCNTCNT              -150

GTTCGCCTNGATCACCTACTAGTCGCGCGCCNNGCGCGACAGGATCAACG              -200

CCAAGGTGATGGCCGATCCCCGCCTGGCGTCGTCGATGGATC -242 SEQ ID NO:11

5'3' GCA4 Frame 1 cgcgctggactatcnctaaagggtctccnacnacgtccanccggacnagctgacctcgtt
 R  A  G  L  X  L  K  G  L  X  X  R  P  X  G  X  A  D  L  V tccncnaagcgtgaaactgaaggccggtgaaaccntcntgttcgcctngatcacctacta
 S  X  K  R  E  T  E  G  R  -  N  X  X  V  R  X  D  H  L  L gtcgcgcgccnngcgcgacaggatcaacgccaaggtgatggccgatccccgcctggcgtc
 V  A  R  X  A  R  Q  D  Q  R  Q  G  D  G  R  S  P  P  G  V gtcgatggatc (SEQ ID NO:39)
 V  D  G      (SEQ ID NO:40)

5'3' GCA4 Frame 2 cgcgctggactatcnctaaagggtctccnacnacgtccanccggacnagctgacctcgttt
  A  L  D  Y  X  -  R  V  S  X  X  V  X  P  D  X  L  T  S  F ccncnaagcgtgaaactgaaggccggtgaaaccntcntgttcgcctngatcacctactag
 X  X  S  V  K  L  K  A  G  E  T  X  X  F  A  X  I  T  Y  -
```

```
tcgcgcgccnngcgcgacaggatcaacgccaaggtgatggccgatccccgcctggcgtcg
  S  R  A  X  R  D  R  I  N  A  K  V  M  A  D  P  R  L  A  S tcgatggatc (SEQ ID NO:41)
 S  M  D   (SEQ ID NO:42)
```

5'3' GCA4 Frame 3

```
cgcgctggactatcnctaaagggtctccnacnacgtccanccggacnagctgacctcgtttc
   R  W  T  I  X  K  G  S  X  X  T  S  X  R  X  S  -  P  R  F cncnaagcgtgaaactgaaggccggtgaaaccntcntgttcgcctngatcacctactagt
 X  X  A  -  N  -  R  P  V  K  X  X  C  S  P  X  S  P  T  S cgcgcgccnngcgcgacaggatcaacgccaaggtgatggccgatccccgcctggcgtcgt
 R  A  X  X  A  T  G  S  T  P  R  -  W  P  I  P  A  W  R  R cgatggatc (SEQ ID NO:43)
 R  W  I  (SEQ ID NO:44)
```

3'5' GCA4 Frame 1

```
gatccatcgacgacgccaggcggggatcggccatcaccttggcgttgatcctgtcgcgcn
 D  P  S  T  T  P  G  G  D  R  P  S  P  W  R  -  S  C  R  X nggcgcgcgactagtaggtgatcnaggcgaacanganggtttcaccggccttcagtttca
 X  R  A  T  S  R  -  X  R  R  T  X  X  F  H  R  P  S  V  S cgcttngnggaaacgaggtcagctngtccggntggacgtngtnggagaccctttagngat
 R  X  X  E  T  R  S  A  X  P  X  G  R  X  X  R  P  F  X  D agtccagcgcg (SEQ ID NO:45)
 S  P  A    (SEQ ID NO:46)
```

3'5' GCA4 Frame 2

```
gatccatcgacgacgccaggcggggatcggccatcaccttggcgttgatcctgtcgcgcnn
  I  H  R  R  R  Q  A  G  I  G  H  H  L  G  V  D  P  V  A  X ggcgcgcgactagtaggtgatcnaggcgaacanganggtttcaccggccttcagtttcac
 G  A  R  L  V  G  D  X  G  E  X  X  G  F  T  G  L  Q  F  H gcttngnggaaacgaggtcagctngtccggntggacgtngtnggagaccctttagngata
 A  X  X  K  R  G  Q  X  V  R  X  D  X  X  G  D  P  L  X  I gtccagcgcg
 V  Q  R   (SEQ ID NO:47)
```

3'5' GCA4 Frame 3

```
gatccatcgacgacgccaggcggggatcggccatcaccttggcgttgatcctgtcgcgcnng
    S  I  D  D  A  R  R  G  S  A  I  T  L  A  L  I  L  S  R  X gcgcgcgactagtaggtgatcnaggcgaacanganggtttcaccggccttcagtttcacg
 A  R  D  -  -  V  I  X  A  N  X  X  V  S  P  A  P  S  F  T cttngnggaaacgaggtcagctngtccggntggacgtngtnggagaccctttagngatag
 L  X  G  N  E  V  S  X  S  X  W  T  X  X  E  T  L  -  X  - tccagcgcg
 S  S  A  (SEQ ID NO:48)
```

GCA5

| | |
|---|---|
| GATCCGCTCGATGCCCAGGCCCAGTACAGCGAACTGTTCGCCCATGGCCG | -50 |
| CGCCACGTCACTGTTGCTATTCGAACATGTTCACGGTGAATCCCGTGACC | -100 |
| GCGGCCAGGCGATGGTGGACCTGCTGGCGCAGTACGAGCAGCACGGTTTG | -150 |
| CAGTTAAACAGCCGCGAATTACCGGACCACCTGCCGCTGTATCTGGAGTA | -200 |
| CCTGTCGCAGCTGCCGCAAGGCGAAGCCGTGGAAGGTTTGAAAGATATCG | -250 |
| CGCCGATTCTGGCATTGCTGAGCGCGCGTCTGCAACAGCGTGAAAGCCGT | -300 |
| TATGCCGTGATGTTTGATCTGCTGCTGAAATTCGCCGATACCGCTATCGA | -350 |
| CAGCGACAAAGTGGCGGAAAAAATTGCCGACGAAGCGCGCGATGATACGC | -400 |

```
CGCAGGCGCTGGATGCTGTTTGGGAAGAAGAGCAGGTTAAATTCTTTGCT              -450

GACAAAGGCTGCGGCGATTCAGCAATCACTGCTCATCAGCGTCGCTTTGC              -500

CGGTGdCGTCGCGCCGCAATATCTGAATATCCTCGGTGAGAGGCTGGAGA              -550
```

GT -552 SEQ ID NO:12

5'3' GCA5 Frame 1

```
gatccgctcgatgcccaggcccagtacagcgaactgttcgcccatggccgcgccacgtca
 D  P  L  D  A  Q  A  Q  Y  S  E  L  F  A  H  G  R  A  T  S ctgttgctattcgaacatgttcacggtgaatcccgtgaccgcggccaggcgatggtggac
 L  L  L  F  E  H  V  H  G  E  S  R  D  R  G  Q  A  M  V  D ctgctggcgcagtacgagcagcacggtttgcagttaaacagccgcgaattaccggaccac
 L  L  A  Q  Y  E  Q  M  G  L  Q  L  N  S  R  E  L  P  D  H ctgccgctgtatctggagtacctgtcgcagctgccgcaaggcgaagccgtggaaggtttg
 L  P  L  Y  L  E  Y  L  S  Q  L  P  Q  G  E  A  V  E  G  L aaagatatcgcgccgattctggcattgctgagcgcgcgtctgcaacagcgtgaaagccgt
 K  D  I  A  P  I  L  A  L  L  S  A  R  L  Q  Q  R  E  S  R tatgccgtgatgtttgatctgctgctgaaattggccgataccgctatcgacagcgacaaa
 Y  A  V  M  F  D  L  L  L  K  L  A  D  T  A  I  D  S  D  K gtggcggaaaaaattgccgacgaagcgcgcgatgatacgccgcaggcgctggatgctgtt
 V  A  E  K  I  A  D  E  A  R  D  D  T  P  Q  A  L  D  A  V tgggaagaagagcaggttaaattctttgctgacaaaggctgcggcgattcagcaatcact
 W  E  E  E  Q  V  K  F  F  A  D  K  G  C  G  D  S  A  I  T gctcatcagcgtcgctttgccggtgccgtcgcgccgcaatatctgaatatcctcggtgag
 A  H  Q  R  R  F  A  G  A  V  A  P  Q  Y  L  N  I  L  G  E aggctggagagt (SEQ ID NO:49)
 R  L  E  S  (SEQ ID NO:50)
```

5'3' GCA5 Frame 2

```
gatccgctcgatgcccaggcccagtacagcgaactgttcgcccatggccgcgccacgtcac
  I  R  S  M  P  R  P  S  T  A  N  C  S  P  M  A  A  P  R  H tgttgctattcgaacatgttcacggtgaatcccgtgaccgcggccaggcgatggtggacc
 C  C  Y  S  N  M  F  T  V  N  P  V  T  A  A  R  R  W  W  T tgctggcgcagtacgagcagcacggtttgcagttaaacagccgcgaattaccggaccacc
 C  W  R  S  T  S  S  T  V  C  S  -  T  A  A  N  Y  R  T  T tgccgctgtatctggagtacctgtcgcagctgccgcaaggcgaagccgtggaaggtttga
 C  R  C  I  W  S  T  C  R  S  C  R  K  A  K  P  W  K  V  - aagatatcgcgccgattctggcattgctgagcgcgcgtctgcaacagcgtgaaagccgtt
 K  I  S  R  R  F  W  H  C  -  A  R  V  C  N  S  V  K  A  V atgccgtgatgtttgatctgctgctgaaattggccgataccgctatcgacagcgacaaag
 M  P  -  C  L  I  C  C  -  N  W  P  I  P  L  S  T  A  T  K tggcggaaaaaattgccgacgaagcgcgcgatgatacgccgcaggcgctggatgctgttt
 W  R  K  K  L  P  T  K  R  A  M  I  R  R  R  R  W  M  L  F gggaagaagagcaggttaaattctttgctgacaaaggctgcggcgattcagcaatcactg
 G  K  K  S  R  L  N  S  L  L  T  K  A  A  A  I  Q  Q  S  L ctcatcagcgtcgctttgccggtgccgtcgcgccgcaatatctgaatatcctcggtgaga
 L  I  S  V  A  L  P  V  P  S  R  R  N  I  -  I  S  S  V  R ggctggagagt (SEQ ID NO:51)
 G  W  R  (SEQ ID NO:52)
```

5'3' GCA5 Frame 3

```
gatccgctcgatgcccaggcccagtacagcgaactgttcgcccatggccgcgccacgtcact
   S  A  R  C  P  G  P  V  Q  R  T  V  R  P  W  P  R  H  V  T gttgctattcgaacatgttcacggtgaatcccgtgaccgcggccaggcgatggtggacct
  V  A  I  R  T  C  S  R  -  I  P  -  P  R  P  G  D  G  G  P
```

-continued

```
gctggcgcagtacgagcagcacggtttgcagttaaacagccgcgaattaccggaccacct
 A  G  A  V  R  A  A  R  F  A  V  K  Q  P  R  I  T  G  P  P gccgctgtatctggagtacctgtcgcagctgccgcaaggcgaagccgtggaaggtttgaa
 A  A  V  S  G  V  P  V  A  A  A  A  R  R  S  R  G  R  F  E agatatcgcgccgattctggcattgctgagcgcgcgtctgcaacagcgtgaaagccgtta
 R  Y  R  A  D  S  G  I  A  E  R  A  S  A  T  -  K  P  L tgccgtgatgtttgatctgctgctgaaattggccgataccgctatcgacagcgacaaagt
 C  R  D  V  -  S  A  A  E  I  G  R  Y  R  Y  R  Q  R  Q  S ggcggaaaaaattgccgacgaagcgcgcgatgatacgccgcaggcgctggatgctgtttg
 G  G  K  N  C  R  R  S  A  R  -  Y  A  A  G  A  G  C  C  L ggaagaagagcaggttaaattctttgctgacaaaggctgcggcgattcagcaatcactgc
 G  R  R  A  G  -  I  L  C  -  Q  R  L  R  R  F  S  N  H  C tcatcagcgtcgctttgccggtgccgtcgcgccgcaatatctgaatatcctcggtgagag
 S  S  A  S  L  C  R  C  R  R  A  A  I  S  E  Y  P  R  -  E gctggagagt (SEQ ID NO:53)
 A  G  E  (SEQ ID NO:54)

3'5' GCA5 Frame 1 actctccagcctctcaccgaggatattcagatattgcggcgcgacggcaccggcaaagcg
 T  L  Q  P  L  T  E  D  I  Q  I  L  R  R  D  G  T  G  K  A acgctgatgagcagtgattgctgaatcgccgcagcctttgtcagcaaagaatttaacctg
 T  L  M  S  S  D  C  -  I  A  A  A  F  V  S  K  E  F  N  L ctcttcttcccaaacagcatccagcgcctgcggcgtatcatcgcgcgcttcgtcggcaat
 L  F  F  P  N  S  I  Q  R  L  R  R  I  I  A  R  F  V  G  N tttttccgccactttgtcgctgtcgatagcggtatcggccaatttcagcagcagatcaaa
 F  F  R  H  F  V  A  V  D  S  G  I  G  Q  F  Q  Q  Q  I  K catcacggcataacggctttcacgctgttgcagacacacactcagcaatgccagaatcga
 H  H  G  I  T  A  F  T  L  L  Q  T  R  A  Q  Q  C  Q  N  R cgcgatatctttcaaaccttccacggcttcgccttgcggcagctgcgacaggtactccag
 R  D  I  F  Q  T  F  H  G  F  A  L  R  Q  L  R  Q  V  L  Q atacagcggcaggtggtccggtaattcgcggctgtttaactgcaaaccgtgctgctcgta
 I  Q  R  Q  V  V  R  -  F  A  A  V  -  L  Q  T  V  L  L  V ctgcgccagcaggtccaccatcgcctggccgcggtcacgggattcaccgtgaacatgttc
 L  R  Q  Q  V  H  H  R  L  A  A  V  T  G  F  T  V  N  M  F gaatagcaacagtgacgtggcgcggccatgggcgaacagttcgctgtactgggcctgggc
 E  -  Q  Q  -  R  G  A  A  M  G  E  Q  F  A  V  L  G  L  G atcgagcggatc (SEQ ID NO:55)
 I  E  R  I  (SEQ ID NO:56)

3'5' GCA5 Frame 2 actctccagcctctcaccgaggatattcagatattgcggcgcgacggcaccggcaaagcga
  L  S  S  L  S  P  R  I  F  R  Y  C  G  A  T  A  P  A  K  R cgctgatgagcagtgattgctgaatcgccgcagcctttgtcagcaaagaatttaacctgc
  R  -  -  A  V  I  A  E  S  P  Q  P  L  S  A  K  N  L  T  C tcttcttcccaaacagcatccagcgcctgcggcgtatcatcgcgcgcttcgtcggcaatt
  S  S  S  Q  T  A  S  S  A  C  G  V  S  S  R  A  S  S  A  I ttttccgccactttgtcgctgtcgatagcggtatcggccaatttcagcagcagatcaaac
  F  S  A  T  L  S  L  S  I  A  V  S  A  N  F  S  S  R  S  N atcacggcataacggctttcacgctgttgcagacgcgcgctcagcaatgccagaatcggc
  I  T  A  -  R  L  S  R  C  C  R  R  A  L  S  N  A  R  I  G gcgatatctttcaaaccttccacggcttcgccttgcggcagctgcgacaggtactccaga
  A  I  S  F  K  P  S  T  A  S  P  C  G  S  C  D  R  Y  S  R tacagcggcaggtggtccggtaattcgcggctgtttaactgcaaaccgtgctgctcgtac
  Y  S  G  R  W  S  G  N  S  R  L  F  N  C  K  P  C  C  S  Y
```

```
tgcgccagcaggtccaccatcgcctggccgcggtcacgggattcaccgtgaacatgttcg
 C  A  S  R  S  T  I  A  W  P  R  S  R  D  S  -  T  C  S aatagcaacagtgacgtggcgcggccatgggcgaacagttcgctgtactgggcctgggca
 N  S  N  S  D  V  A  R  P  W  A  N  S  S  L  Y  W  A  W  A tcgagcggatc
 S  S  G  (SEQ ID NO:57)
```

3'5' GCA5 Frame 3

```
actctccagcctctcaccgaggatattcagatattgcggcgcgacggcaccggcaaagcgac
   S  P  A  S  H  R  G  Y  S  D  I  A  A  R  R  H  R  Q  S  D gctgatgagcagtgattgctgaatcgccgcagcctttgtcagcaaagaatttaacctgct
 A  D  E  Q  -  L  L  N  R  R  S  L  C  Q  Q  R  I  -  P  A cttcttcccaaacagcatccagcgcctgcggcgtatcatcgcgcgcttcgtcggcaattt
 L  L  P  K  Q  H  P  A  P  A  A  Y  H  R  A  L  R  R  Q  F tttccgccactttgtcgctgtcgatagcggtatcggccaatttcagcagcagatcaaaca
 F  P  P  L  C  R  C  R  -  R  Y  R  P  I  S  A  A  D  Q  T tcacggcataacggctttcacgctgttgcagacgcgcgctcagcaatgccagaatcggcg
 S  R  H  N  G  F  H  A  V  A  D  A  R  S  A  M  P  E  S  A cgatatctttcaaaccttccacggcttcgccttgcggcagctgcgacaggtactccagat
 R  Y  L  S  N  L  P  R  L  R  L  A  A  A  T  G  T  P  D acagcggcaggtggtccggtaattcgcggctgtttaactgcaaaccgtgctgctcgtact
 T  A  A  G  G  P  V  I  R  G  C  L  T  A  N  R  A  A  R  T gcgccagcaggtccaccatcgcctggccgcggtcacgggattcaccgtgaacatgttcga
 A  P  A  G  P  P  S  P  G  R  G  H  G  I  H  R  E  H  V  R atagcaacagtgacgtggcgcggccatgggcgaacagttcgctgtactgggcctgggcat
 I  A  T  V  T  W  R  G  H  G  R  T  V  R  C  T  G  P  G  H cgagcggatc
 R  A  D  (SEQ ID NO:58)
```

GCA7

```
GATCCTNACACANTAGCCCGTGGACGCATTTGCGTCGACCCTCATANGGA              -50

AGCGATACGAGGCGGGTNAAAGTGAACATCCGCCGAGCACGGCAGCGACG             -100

CCTCCGCTCACCGTCNGCGCAGTACTTCCTCGGGTCGCCGCGCCTAGCAC             -150

TCTGCGCCGTGACATGAANCCGTGAACCCACGGGAGACTTTGCGCCGCNA             -200

AGGGATGAGTCCACTATTAGATGACGCATGGCTACGAGCCNATCCTCGGT             -250

GANAAGCTGGAGAGT -265 SEQ ID NO:13
```

5'3' GCA7 Frame 1

```
gatcctnacacantagcccgtggacgcatttgcgtcgaccctcatanggaagcgatacga
 D  P  X  T  X  A  R  G  R  I  C  V  D  P  H  X  E  A  I  R ggcgggtnaaagtgaacatccgccgagcacggcagcgacgcctccgctcaccgtcngcgc
 G  G  X  K  -  T  S  A  E  H  G  S  D  A  S  A  H  R  X  R agtacttcctcgggtcgccgcgcctagcactctgcgccgtgacatcaanccgtgaaccca
 S  T  S  S  G  R  R  A  -  H  S  A  P  -  H  Q  X  V  N  P cgggagactttgcgccgcnaagggatgagtccactattagatgacgcatggctacgagcc
 R  E  T  L  R  R  X  G  M  S  P  L  L  D  D  A  W  L  R  A natcctcggtganaagctggagagt (SEQ ID NO:59)
 X  P  R  -  X  A  G  E  (SEQ ID NO:60)
```

5'3' GCA7 Frame 2

```
gatcctnacacantagcccgtggacgcatttgcgtcgaccctcatanggaagcgatacgag
  I  X  T  X  -  P  V  D  A  F  A  S  T  L  I  X  K  R  Y  E gcgggtnaaagtgaacatccgccgagcacggcagcgacgcctccgctcaccgtcngcgca
 A  G  X  S  E  H  P  P  S  T  A  A  T  P  P  L  T  V  X  A
```

-continued

```
gtacttcctcgggtcgccgcgcctagcactctgcgccgtgacatcaanccgtgaacccac
 V   L   P   R   V   A   A   P   S   T   L   R   R   D   I   X   P   -   T   H gggagactttgcgccgcnaagggatgagtccactattagatgacgcatggctacgagccn
 G   R   L   C   A   X   K   G   -   V   H   Y   -   M   T   H   G   Y   E   X atcctcggtganaagctggagagt (SEQ ID NO:61)
 I   L   G   X   K   L   E   S  (SEQ ID NO:62)
```

5'3' GCA7 Frame 3

```
gatcctnacacantagcccgtggacgcatttgcgtcgaccctcatanggaagcgatacgagg
   S   X   H   X   S   P   W   T   H   L   R   R   P   S   X   G   S   D   T   R cgggtnaaagtgaacatccgccgagcacggcagcgacgcctccgctcaccgtcmgcgcag
 R   X   K   V   N   I   R   R   A   R   Q   R   R   L   R   S   P   X   A   Q tacttcctcgggtcgccgcgcctagcactctgagccgtgacatcaanccgtgaacccacg
 Y   F   L   G   S   P   R   L   A   L   C   A   V   T   S   X   R   E   P   T ggagactttgcgccgcnaagggatgagtccactattagatgacgcatggctacgagcca
 G   D   F   A   P   X   R   D   E   S   T   I   R   -   R   M   A   T   S   X tcctcggtganaagctggagagt (SEQ ID NO:63)
 S   S   V   X   S   W   R  (SEQ ID NO:64)
```

3'5' GCA7 Frame 1

```
actctccagcttntcaccgaggatnggctcgtagccatgcgtcatctaatagtggactca
 T   L   Q   L   X   T   E   D   X   L   V   A   M   R   H   L   I   V   D   S tcccttngcggcgcaaagtctcccgtgggttcacggnttgatgtcacggcgcagagtgct
 S   L   X   G   A   K   S   P   V   G   S   R   X   D   V   T   A   Q   S   A aggcgcggcgacccgaggaagtactgcgcngacggtgagcggaggcgtcgctgccgtgct
 R   R   G   D   P   R   K   Y   C   X   D   G   E   R   R   R   R   C   R   A cggcggatgttcactttnacccgcctcgtatcgcttccntatgagggtcgacgcaaatgc
 R   R   M   F   T   X   T   R   L   V   S   L   X   Y   E   G   R   R   K   C gtccacgggctantgtgtnaggatc (SEQ ID NO:65)
 V   H   G   L   X   C   X   D  (SEQ ID NO:66)
```

3'5' GCA7 Frame 2

```
actctccagcttntcaccgaggatnggctcgtagccatgagtcatctaatagtggactcatc
   L   S   S   X   S   P   R   X   G   S   -   P   C   V   I   -   -   W   T   H ccttngcggcgcaaagtctcccgtgggttcacggnttgatgtcacggcgcagagtgctag
 P   X   A   A   Q   S   L   P   W   V   H   X   L   M   S   R   R   R   V   L ggcgcggcgacccgaggaagtactgcgcngacggtgagcggaggcgtcgctgccgtgctc
 G   A   A   T   R   G   S   T   A   X   T   V   S   G   G   V   A   A   V   L ggcggatgttcactttnacccgcctcgtatcgcttccntatgagggtcgacgcaaatgcg
 G   G   C   S   L   X   P   A   S   Y   R   F   X   M   R   V   D   A   N   A tccacgggctantgtgtnaggatc
 S   T   G   X   C   X   R   I  (SEQ ID NO:67)
```

3'5' GCA7 Frame 3

```
actctccagcttntcaccgaggatnggctcgtagccatgcgtcatctaatagtggactcatc
   S   P   A   X   H   R   G   X   A   R   S   H   A   S   S   N   S   G   L   I ccttngcggcgcaaagtctcccgtgggttcacggnttgatgtcacggcgcagagtgctag
 P   X   R   R   K   V   S   R   G   F   T   X   -   C   H   G   A   E   C   - gcgcggcgacccgaggaagtactgcgcngacggtgagcggaggcgtcgctgccgtgctcg
 A   R   R   P   E   E   V   L   R   X   R   -   A   E   A   S   L   P   C   S gcggatgttcactttnacccgcctcgtatcgcttccntatgagggtcgacgcaaatgcgt
 A   D   V   H   F   X   P   P   R   I   A   S   X   -   G   S   T   Q   M   R ccacgggctantgtgtnaggatc
 P   R   A   X   V   X   G  (SEQ ID NO:68)
```

GCA10

```
GATCCGGCCNCGCACGANCTTACCGGTNAAAACTTCCNCNCCNATAATAT                    -50
```

```
TTGCCGCGCGAGCCGCCCTGANGCTCTCGGCGTAACTCCGGATGCACGGG        -100

GGACCGTGACGGTTGTANTGCCCTGGCTTTTCTCAGCNGAAATCTGCACA        -150

GCCATCTTCCGATCGATCTGGCGCAGGTGGGGCGGCNCAAAACGGTGGGC        -200

ATCTCCAAACCGCAGGAACGTGTTTTGCAGGATGTCGAACATCATCCACG        -250

CTTCGGTNCCCAACGGCTACTTCGCCCGGTACCGGGCCATGTCATCCTCG        -300

GTGANAAGCTGGANANT -317 SEQ ID NO:14

5'3' GCA10 Frame 1 gatccggccncgcacgancttaccggtnaaaacttccncaccnataatatttgccgcgcg
 D  P  A  X  H  X  L  T  G  X  N  F  X  X  X  N  I  C  R  A agccgccctgangctctcggcgtaactccggatgcacggggaccgtgacggttgtantg
 S  R  P  X  A  L  G  V  T  P  D  A  R  G  T  V  T  V  V  X ccctggcttttctcagcngaaatctgcacagccatcttccgatcgatctggcgcaggtgg
 P  W  L  F  S  X  E  I  C  T  A  I  F  R  S  I  W  R  R  W ggcggcncaaaacggtgggcatctccaaaccgcaggaacgtgttttgcaggatgtcgaac
 G  G  X  K  R  W  A  S  P  N  R  R  N  V  F  C  R  M  S  N atcatccacgcttcggtncccaacggctacttcgcccggtaccgggccatgtcatcctcg
 I  I  H  A  D  X  P  N  G  Y  F  A  R  Y  R  A  M  S  S  S gtganaagctgganant (SEQ ID NO:69)
 V  X  B  W  X  X  (SEQ ID NO:70)

5'3' GCA10 Frame 2 gatccggccncgcacgancttaccggtnaaaacttccncnccnataatatttgccgcgcga
  I  R  X  R  T  X  L  P  X  K  T  S  X  X  I  I  F  A  A  R gccgccctgangctctcggcgtaactccggatgcacggggaccgtgacggttgtantgc
 A  A  L  X  L  S  A  -  L  R  M  H  G  G  P  -  R  L  X  C cctggcttttctcagcngaaatctgcacagccatcttccgatcgatctggcgcaggtggg
 P  G  F  S  Q  X  K  S  A  Q  P  S  S  D  R  S  G  A  G  G gcggcncaaaacggtgggcatctccaaaccgcaggaacgtgttttgcaggatgtcgaaca
 A  X  Q  N  G  G  H  L  Q  T  A  G  T  C  F  A  G  C  R  T tcatccacgcttcggtncccaacggctacttcgcccggtaccgggccatgtcatcctcgg
 S  S  T  L  R  X  P  T  A  T  S  P  G  T  G  P  C  H  P  R tganaagctgganant (SEQ ID NO:71)
 -  X  A  G  X  (SEQ ID NO:72)

5'3' GCA10 Frame 3 gatccggccncgcacgancttaccggtnaaaacttccncnccnataatatttgccgcgcgag
   S  G  X  A  R  X  Y  R  X  K  L  X  X  X  -  Y  L  P  R  E ccgccctgangctctcggcgtaactccggatgcacggggaccgtgacggttgtantgcc
 P  P  -  X  S  R  R  N  S  G  C  T  G  D  R  D  G  C  X  A ctggcttttctcagcngaaatctgcacagccatcttccgatcgatctggcgcaggtgggg
 L  A  F  L  S  X  N  L  H  S  H  L  P  I  D  L  A  Q  V  G cggcncaaaacggtgggcatctccaaaccgcaggaacgtgttttgcaggatgtcgaacat
 R  X  K  T  V  G  I  S  K  P  Q  E  R  V  L  Q  D  V  E  H catccacgcttcggtncccaacggctacttcgcccggtaccgggccatgtcatcctcggt
 H  P  R  F  G  X  Q  R  L  L  R  P  V  P  G  H  V  I  L  G ganaagctgganant (SEQ ID NO:73)
 X  K  L  X  X  (SEQ ID NO:74)

3'5' GCA10 Frame 1 antntccagcttntcaccgaggatgacatggcccggtaccgggcgaagtagccgttgggn
 X  X  Q  L  X  T  E  D  D  M  A  R  Y  R  A  K  -  P  L  X accgaagcgtggatgatgttcgacatcctgcaaaacacgttcctgcggtttggagatgcc
 T  E  A  W  M  M  F  D  I  L  Q  N  T  F  L  R  F  G  D  A
```

-continued

```
caccgttttgngccgccccacctgcgccagatcgatcggaagatggctgtgcagatttcn
 H  R  F  X  P  P  H  L  R  Q  I  D  R  K  M  A  V  Q  I  X gctgagaaaagccagggcantacaaccgtcacggtccccgtgcatccggagttacgccg
 A  E  K  S  Q  G  X  T  T  V  T  V  P  R  A  S  G  V  T  P agagcntcagggcggctcgcgcggcaaatattatnggngnggaagttttnaccggtaagn
 R  X  S  G  R  L  A  R  Q  I  L  X  X  X  K  F  X  P  V  X tcgtgcgnggccggatc (SEQ ID NO:75)
 S  C  X  A  G  (SEQ ID NO:76)
```

3'5' GCA10 Frame 2

```
antntccagcttntcaccgaggatgacatggcccggtaccgggcgaagtagccgttgggna
  X  S  S  X  S  P  R  M  T  W  P  G  T  G  R  S  S  R  W  X ccgaagcgtggatgatgttcgacatcctgcaaaacacgttcctgcggtttggagatgccc
 P  K  R  G  -  C  S  T  S  C  K  T  R  S  C  G  L  E  M  P accgttttgngccgccccacctgcgccagatcgatcggaagatggctgtgcagatttcng
 T  V  L  X  R  P  T  C  A  R  S  I  G  R  W  L  C  R  F  X ctgagaaaagccagggcantacaaccgtcacggtccccgtgcatccggagttacgcccga
 L  R  K  A  R  A  X  Q  P  S  R  S  P  V  H  P  E  L  R  R gagcntcagggcggctcgcgcggcaaatattatnggngnggaagttttnaccggtaagnt
 E  X  Q  G  G  S  R  G  K  Y  Y  X  X  G  S  F  X  R  -  X cgtgcgnggccggatc
 R  A  X  P  D  (SEQ ID NO:77)
```

3'5 GCA10 Frame 3

```
antntccagcttntcaccgaggatgacatggcccggtaccgggcgaagtagccgttgggnac
   X  P  A  X  H  R  G  -  H  G  P  V  P  G  E  V  A  V  G  X cgaagcgtggatgatgttcgacatcctgcaaaacacgttcctgcggtttggagatgcca
 R  S  V  D  D  V  R  H  P  A  K  H  V  P  A  V  W  R  C  P ccgttttgngccgccccacctgcgccagatcgatcggaagatggctgtgcagatttcngc
 P  F  X  A  A  P  P  A  P  D  R  S  E  D  G  C  A  D  F  X tgagaaaagccagggcantacaaccgtcacggtccccgtgcatccggagttacgccgag
 -  E  K  P  G  X  Y  N  R  H  G  P  P  C  I  R  S  Y  A  E agcntcagggcggctcgcgcggcaaatattatnggngnggaagttttnaccggtaagntc
 S  X  R  A  A  R  A  A  N  I  X  X  X  R  V  X  T  G  K  X gtgcgnggccggatc
 V  X  G  R  I  (SEQ ID NO:78)
```

GCA12

| | |
|---|---|
| ACTCTCCAGCCTCGCACCGAGGATCAGGGCGTCGTCGACTCCGTCGACCT | -50 |
| GACCGCCTCCCCNCCGCTGCTCTCGATCGGCGGCCAGACCTACACCANCG | -100 |
| ACGTAGATCAAGCGCGTGGTGCGCGGCGCNACNAGCANCANCTAANTCAA | -150 |
| GGCCTCGCTGCATCCCGCCAATCCAGCGCTCAGCTTCGCGGGAATTGCGC | -200 |
| GANCGCTTTTGCGCGTCNCGAGTNACCGCATACACACCTGCCGTCCCTGC | -250 |
| GAAAGCAAGGACCCATACTCCGCNGCGGGTGTTGTTGACGGGACTCGTCA | -300 |
| TGGCGGCAACGCACAACGTNNAACTTCTGTGGTTATGGATC | -341 SEQ ID NO:15 |

5'3' GCA12 Frame 1

```
actctccagcctcgcaccgaggatcagggcgtcgtcgactccgtcgacctgaccgcctcc
 T  L  Q  P  R  T  E  D  Q  G  V  V  D  S  V  D  L  T  A  S ccnccgctgctctcgatcggcggccagacctacaccancgacgtagatcaagcgcgtggt
 X  P  L  L  S  I  G  G  Q  T  Y  T  X  D  V  D  Q  A  R  G gcgcggcgcnacnagcancanctaantcaaggcctcgctgcatcccgccaatccagcgct
 A  R  R  X  X  X  X  L  X  Q  G  L  A  A  S  R  Q  S  S  A
```

-continued

```
cagcttcgcgggaattgcgcgancgcttttgcgcgtcncgagtnaccgcatacacacctg
 Q  L  R  G  N  C  A  X  A  F  A  R  X  E  X  P  H  T  H  L ccgtccctgcgaaagcaaggacccatactccgcngcgggtgttgttgacgggactcgtca
 P  S  L  R  K  Q  G  P  I  L  R  X  G  C  C  -  R  D  S  S tggcggcaacgcacaactgnnaacttctgtggttatggatc (SEQ ID NO:79)
 W  R  Q  R  T  T  X  N  F  C  G  Y  G  (SEQ ID NO:80)
```

5'3' GCA12 Frame 2

```
actctccagcctcgcaccgaggatcagggcgtcgtcgactccgtcgacctgaccgcctccc
  L  S  S  L  A  P  R  I  R  A  S  S  T  P  S  T  -  P  P  P cnccgctgctctcgatcggcggccagacctacaccancgacgtagatcaagcgcgtggtg
  X  R  C  S  R  S  A  A  R  P  T  P  X  T  -  I  K  R  V  V cgcggcgcnacnagcancanctaantcaaggcctcgctgcatcccgccaatccagcgctc
  R  G  X  X  S  X  X  -  X  K  A  S  L  H  P  A  N  P  A  L agcttcgcgggaattgcgcgancgcttttgcgcgtcncgagtnaccgcatacacacctgc
  S  F  A  G  I  A  R  X  L  L  R  V  X  S  X  R  I  H  T  C cgtccctgcgaaagcaaggacccatactccgcngcgggtgttgttgacgggactcgtcat
  R  P  C  E  S  K  D  P  Y  S  X  A  G  V  V  D  G  T  R  H ggcggcaacgcacaacgtnnaacttctgtggttatggatc (SEQ ID NO:81)
  G  G  N  A  Q  R  X  T  S  V  V  M  D  (SEQ ID NO:82)
```

5'3' GCA12 Frame 3

```
actctccagcctcgcaccgaggatcagggcgtcgtcgactccgtcgacctgaccgcctcccc
   S  P  A  S  H  R  G  S  G  R  R  R  L  R  R  P  D  R  L  P nccgctgctctcgatcggcggccagacctacaccancgacgtagatcaagcgcgtggtgc
 X  A  A  L  D  R  R  P  D  L  H  X  R  R  R  S  S  A  W  C gcggcgcnacnagcancanctaatcaaggcctcgctgcatcccgccaatccagcgctca
 A  A  X  X  A  X  X  X  S  R  P  R  C  I  P  P  I  Q  R  S gcttcgcgggaattgcgcgancgcttttgcgcgtcncgagtnaccgcatacacacctgcc
 A  S  R  E  L  R  X  R  F  C  A  X  R  X  T  A  Y  T  P  A gtccctgcgaaagcaaggacccatactccgcngcgggtgttgttgacgggactcgtcatg
 V  P  A  K  A  R  T  H  T  P  X  R  V  L  L  T  G  L  V  M gcggcaacgcacaacgtnnaacttctgtggttatggatc (SEQ ID NO:83)
 A  A  T  H  N  X  X  L  L  W  L  W  I  (SEQ ID NO:84)
```

3'5' GCA12 Frame 1

```
gatccataaccacagaagttnnacgttgtgcgttgccgccatgacgagtcccgtcaacaa
 D  P  -  P  Q  K  X  X  V  V  R  C  R  H  D  E  S  R  Q  Q cacccgcngcggagtatgggtccttgctttcgcagggacggcaggtgtgtatgcggtnac
 H  P  X  R  S  M  G  P  C  F  R  R  D  G  R  C  V  C  G  X tcgngacgcgcaaaagcgntcgcgcaattcccgcgaagctgagcgctggattggcgggat
 S  X  R  A  K  A  X  A  Q  F  P  R  S  -  A  L  D  W  R  D gcagcgaggccttganttagntgntgctngtngcgccgcgcaccacgcgcttgatctacg
 A  A  R  P  -  X  X  X  C  X  X  R  R  A  P  R  A  -  S  T tcgntggtgtaggtctggccgccgatcgagagcagcggnggggaggcggtcaggtcgacg
 S  X  V  -  V  W  P  P  I  E  S  S  X  G  E  A  V  R  S  T gagtcgacgacgccctgatcctcggtgcgaggctggagagt (SEQ ID NO:85)
 E  S  T  T  P  -  S  S  V  R  G  W  R  (SEQ ID NO:86)
```

3'5' GCA12 Frame 2

```
gatccataaccacagaagttnnacgttgtgcgttgccgccatgacgagtcccgtcaacaac
  I  H  N  H  R  S  X  T  L  C  V  A  A  M  T  S  P  V  N  N acccgcngcggagtatgggtccttgctttcgcagggacggcaggtgtgtatgcggtnact
  T  R  X  G  V  W  V  L  A  F  A  G  T  A  G  V  Y  A  X  T cgngacgcgcaaaagcgntcgcgcaattcccgcgaagctgagcgctggattggcgggatg
  X  D  A  Q  K  X  S  R  N  S  R  E  A  E  R  W  I  G  G  M
```

```
                                               -continued
cagcgaggccttganttagntgntgctngtngcgccgcgcaccacgcgcttgatctacgt
 Q   R   G   L   X   L   X   X   A   X   X   A   A   H   H   A   L   D   L   R cgntggtgtaggtctggccgccgatcgagagcagcggngggaggcggtcaggtcgacgg
 X   W   C   R   S   G   R   R   S   R   A   A   X   G   R   R   S   G   R   R agtcgacgacgccctgatcctcggtgcgaggctggagagt
 S   R   R   R   P   D   P   R   C   E   A   G   E (SEQ ID NO:87)

3'5' GCA12 Frame 3 gatccataaccacagaagttnnacgttgtgcgttgccgccatgacgagtcccgtcaacaaca
    S   I   T   T   E   V   X   R   C   A   L   P   P   -   R   V   P   S   T   T cccgcngcggagtatgggtccttgctttcgcaggacggcaggtgtgtatgcggtnactc
 P   X   A   E   Y   G   S   L   L   S   Q   G   R   Q   V   C   M   R   X   L gngacgcgcaaaagcgntcgcgcaattcccgcgaagctgagcgctggattggcgggatgc
 X   T   R   K   S   X   R   A   I   P   A   K   L   S   A   G   L   A   G   C agcgaggccttganttagntgntgctngtngcgccgcgcaccacgcgcttgatctacgtc
 S   E   A   L   X   -   X   X   X   X   A   P   R   T   T   R   L   I   Y   V gntggtgtaggtctggccgccgatcgagagcagcggngggaggcggtcaggtcgacgga
 X   G   V   G   L   A   A   D   R   E   Q   R   X   G   G   G   Q   V   D   G gtcgacgacgccctgatcctcggtgcgaggctggagagt
 V   D   D   A   L   I   L   G   A   R   L   E   S (SEQ ID NO:88)

GCA19

GATCCGCGCATCCTCTCTGTGGCTCTCGCGGGGTCAGAGGTGGATAAGGC             -50

CGGCCGCAAGCTCGGACTTCCCGTCNCAATCNAAGGCTTCTGCGATCNCC             -100

ANTACAACTACNACGGCAATCTNACATCACGCAAGATCGCANGCTCNGTC             -150

ATCAAGGACGCNGCGGTCNCCNCCCGGCAGGTGCTCNATATNGTGTTGAA             -200

NAACACCATCGCTCCTGCAACGGCAAGAAGATCACATGCAAGGTCCACTC             -250

GCTGTG -256  SEQ ID NO:16

5'3' GCA19 Frame 1 gatccgcgcatcctctctgtggctctcgcggggtcagaggtggataaggccggccgcaag
 D   P   R   I   L   S   V   A   L   A   G   S   E   V   D   K   A   G   R   K ctcggacttcccgtcncaatcnaaggcttctgcgatcnccantacaactacnacggcaat
 L   G   L   P   V   X   I   X   G   F   C   D   X   X   Y   N   Y   X   G   N ctnacatcacgcaagatcgcangctcngtcatcaaggacgcngcggtcnccnccggcag
 X   T   S   R   K   I   A   X   X   V   I   K   D   X   A   V   X   X   R   Q gtgctcnatatngtgttgaanaacaccatcgctcctgcaacggcaagaagatcacatgca
 V   L   X   X   V   L   X   N   T   I   A   P   A   T   R   R   S   H   A aggtccactcgctgtg (SEQ ID NO:89)
 R   S   T   R   C (SEQ ID NO:90)

5'3' GCA19 Frame 2 gatccgcgcatcctctctgtggctctcgcggggtcagaggtggataaggccggccgcaagc
    I   R   A   S   S   L   W   L   S   R   G   Q   R   W   I   R   P   A   A   S tcggacttcccgtcncaatcnaaggcttctgcgatcnccantacaactacnacggcaatc
 S   D   F   P   X   Q   X   K   A   S   A   I   X   X   T   T   X   T   A   I tnacatcacgcaagatcgcangctcngtcatcaaggacgcngcggtcnccnccggcagg
 X   H   H   A   R   S   X   A   X   S   S   R   T   X   R   X   X   P   G   R tgctcnatatngtgttgaanaacaccatcgctcctgcaacggcaagaagatcacatgcaa
 C   X   I   X   C   -   X   T   P   S   L   L   Q   R   Q   E   D   H   M   Q ggtccactcgctgtg (SEQ ID NO:91)
 G   P   L   A   V (SEQ ID NO:92)

5'3' GCA19 Frame 3 gatccgcgcatcctctctgtggctctcgcggggtcagag9tggataaggccggccgcaagct
```

```
         S   A   H   P   L   C   G   S   R   G   V   R   G   G   -   G   R   P   Q   A cggacttcccgtcncaatcnaaggcttctgcgatcnccantacaactacnacggcaatct
 R   T   S   R   X   N   X   R   L   L   R   X   P   X   Q   L   X   R   Q   S nacatcacgcaagatcgcangctcngtcatcaaggacgcngcggtcnccncccggcaggt
 X   I   T   Q   D   R   X   L   X   H   Q   G   R   X   C   X   X   P   A   G gctcnatatngtgttgaanaacaccatcgctcctgcaacggcaagaagatcacatgcaag
 A   X   Y   X   V   E   X   H   H   R   S   C   N   G   K   K   I   T   C   K gtccactcgctgtg (SEQ ID NO:93)
 V   H   S   L  (SEQ ID NO:15)

3'5' GCA1 Frame 1 cacagcgagtggaccttgcatgtgatcttcttgccgttgcaggagcgatggtgttnttca
 H   S   E   W   T   L   H   V   I   F   L   P   L   Q   E   R   W   C   X   S acacnatatngagcacctgccgggnggngaccgcngcgtccttgatgacngagcntgcga
 T   X   Y   X   A   P   A   G   X   X   P   X   R   P   -   -   X   S   X   R tcttgcgtgatgtnagattgccgtngtagttgtantggngatcgcagaagccttngattg
 S   C   V   M   X   D   C   R   X   S   C   X   X   D   R   R   S   L   X   L ngacgggaagtccgagcttgcggccggccttatccacctctgaccccgcgagagccacag
 X   R   E   V   R   A   C   G   R   P   Y   P   P   L   T   P   R   E   P   Q agaggatgcgcggatc (SEQ ID NO:95)
 R   G   C   A   D  (SEQ ID NO:96)

3'5' GCA19 Frame 2 cacagcgagtggaccttgcatgtgatcttcttgccgttgcaggagcgatggtgttnttcaa
  T   A   S   G   P   C   M   -   S   S   C   R   C   R   S   D   G   V   X   Q cacnatatngagcacctgccgggnggngaccgcngcgtccttgatgacngagcntgcgat
 H   X   X   E   H   L   P   X   X   D   R   X   V   L   D   D   X   X   C   D cttgcgtgatgtnagattgccgtngtagttgtantggngatcgcagaagccttngattgn
 L   A   -   C   X   I   A   X   V   V   V   X   X   I   A   E   A   X   D   X gacgggaagtccgagcttgcggccggccttatccacctctgaccccgcgagagccacaga
 D   G   K   S   E   L   A   A   G   L   I   H   L   -   P   R   E   S   H   R gaggatgcgcggatc
 E   D   A   R   I  (SEQ ID NO:97)

3'5' GCA19 Frame 3 cacagcgagtggaccttgcatgtgatcttcttgccgttgcaggagcgatggtgttnttcaac
   Q   R   V   D   L   A   C   D   L   L   A   V   A   G   A   M   V   X   F   N acnatatngagcacctgccgggnggngaccgcngcgtccttgatgacngagcntgcgatc
 X   I   X   S   T   C   R   X   X   T   X   A   S   L   M   X   E   X   A   I ttgcgtgatgtnagattgccgtngtagttgtantggngatcgcagaagccttngattgng
 L   R   D   X   R   L   P   X   -   L   X   W   X   S   Q   K   P   X   I   X acgggaagtccgagcttgcggccggccttatccacctctgaccccgcgagagccacagag
 T   G   S   P   S   L   R   P   A   L   S   T   S   D   P   A   R   A   T   E aggatgcgcggatc
 R   M   R   G  (SEQ ID NO:98)
```

Polypeptides and Peptides Associated With GCA

The invention provides polypeptides (e.g., SEQ ID NO:2, SEQ ID NO:4, SEQ ID NO:6, SEQ ID NO:8) associated with GCA, and subsequences of thereof, e.g., peptides. This invention provides immunogenic peptidescapable of generating an immune response, particularly antibodies, specifically directed to diagnose or treat GCA. These polypeptides and peptides can also be used to identify the presence of human antibodies that specifically bind to them for the diagnosis of GCA. Polypeptides and peptides of the invention can also be used to generate antibodies that can be used to diagnose or treat GCA.

Polypeptides and peptides of the invention can be isolated from natural sources (e.g., vasculitis lesions), be synthetic, or be recombinantly generated polypeptides. Peptides and proteins can be recombinantly expressed in vitro or in vivo. The peptides and polypeptides of the invention can be made and isolated using any method known in the art, and the invention provides a few exemplary means for generating such proteins.

Polypeptide and peptides of the invention can also be synthesized, whole or in part, using chemical methods well known in the art. See e.g., Caruthers (1980) Nucleic Acids Res. Symp. Ser. 215–223; Horn (1980) Nucleic Acids Res. Symp. Ser. 225–232; Banga, A. K., Therapeutic Peptides and Proteins, Formulation, Processing and Delivery Systems (1995) Technomic Publishing Co., Lancaster, Pa. For example, peptide synthesis can be performed using various solid-phase techniques (see e.g., Roberge (1995) Science 269:202; Merrifield (1997) Methods Enzymol. 289:3–13) and automated synthesis may be achieved, e.g., using the ABI 431A Peptide Synthesizer (Perkin Elmer) in accordance with the instructions provided by the manufacturer.

The skilled artisan will recognize that individual synthetic residues and polypeptides incorporating mimetics can be synthesized using a variety of procedures and methodologies, which are well described in the scientific and patent literature, e.g., Organic Syntheses Collective Volumes, Gilman, et al. (Eds) John Wiley & Sons, Inc., NY. Polypeptides incorporating mimetics can also be made using solid phase synthetic procedures, as described, e.g., by Di Marchi, et al., U.S. Pat. No. 5,422,426. Peptides and peptide mimetics of the invention can also be synthesized using combinatorial methodologies. Various techniques for generation of peptide and peptidomimetic libraries are well known, and include, e.g., multipin, tea bag, and split-couple-mix techniques; see, e.g., al-Obeidi (1998) Mol. Biotechnol. 9:205–223; Hruby (1997) Curr. Opin. Chem. Biol. 1:114–119; Ostergaard (1997) Mol. Divers. 3:17–27; Ostresh (1996) Methods Enzymol. 267:220–234. Modified peptides of the invention can be further produced by chemical modification methods, see, e.g., Belousov (1997) Nucleic Acids Res. 25:3440–3444; Frenkel (1995) Free Radic. Biol. Med. 19:373–380; Blommers (1994) Biochemistry 33:78867896.

Peptides and polypeptides of the invention can also be synthesized and expressed as fusion proteins with one or more additional domains linked thereto for, e.g. producing a more immunogenic peptide, to more readily isolate a recombinantly synthesized peptide, to identify and isolate antibodies and antibody-expressing B cells, and the like. Detection and purification facilitating domains include, e.g., metal chelating peptides such as polyhistidine tracts and histidine-tryptophan modules that allow purification on immobilized metals, protein A domains that allow purification on immobilized immunoglobulin, and the domain utilized in the FLAGS extension/affinity purification system (Immunex Corp, Seattle Wash.). The inclusion of a cleavable tinker sequences such as Factor Xa or enterokinase (Invitrogen, San Diego Calif.) between the purification domain and GCA-associated peptide or polypeptide can be usefull to facilitate purification. For example, an expression vector can include an epitope-encoding nucleic acid sequence linked to six histidine residues followed by a thioredoxin and an enterokinase cleavage site (see e.g., Williams (1995) Biochemistry 34:1787–1797; Dobeli (1998) Protein Expr. Purif. 12:404–14). The histidine residues facilitate detection and purification while the enterokinase cleavage site provides a means for purifying the epitope from the remainder of the fusion protein. Technology pertaining to vectors encoding fusion proteins and application of fusion proteins are well described in the scientific and patent literature, see e.g., Kroll (1993) DNA Cell. Biol., 12:441–53.

Antibody Generation

The invention provides antibodies that specifically bind to the polypeptides of the invention (e.g., the exemplary SEQ ID NO:2, SEQ ID NO:4, SEQ ID NO:6, or SEQ ID NO:8). These antibodies can be used to identify the presence of polypeptides that associated with GCA to aid in its diagnosis and prognosis.

The peptides and polypeptides of the invention can also be used to generate an immune response to generate antibodies for the diagnosis or treatment of GCA (they can also be used generate a cellular response for treatment). Thus, they can be administered to both humans and animals. The polypeptides or peptide can be conjugated to another molecule or can be administered with an adjuvant. The coding sequence can be part of an expression cassette or vector capable of expressing the immunogen in vivo. (see, e.g., Katsumi (1994) Hum. Gene Ther. 5:1335–9). Methods of producing polyclonal and monoclonal antibodies are known to those of skill in the art and described in the scientific and patent literature, see, e.g., Coligan, CURRENT PROTOCOLS IN IMMUNOLOGY, Wiley/Greene, NY (1991); Stites (eds.) BASIC AND CLINICAL IMMUNOLOGY (7th ed.) Lange Medical Publications, Los Altos, Calif. ("Stites"); Goding, MONOCLONAL ANTIBODIES: PRINCIPLES AND PRACTICE (2d ed.) Academic Press, New York, NY (1986); Kohler (1975) Nature 256:495; Harlow (1988) ANTIBODIES, A LABORATORY MANUAL, Cold Spring Harbor Publications, New York.

Antibodies also can be generated in vitro, e.g., using recombinant antibody binding site expressing phage display libraries, in addition to the traditional in vivo methods using animals. See, e.g., Huse (1989) Science 246:1275; Ward (1989) Nature 341:544; Hoogenboom (1997) Trends Biotechnol. 15:62–70; Katz (1997) Annu. Rev. Biophys. Biomol. Struct. 26:27–45.

Human antibodies can be generated in mice engineered to produce only human antibodies, as described by, e.g., U.S. Pat. Nos. 5,877,397; 5,874,299; 5,789,650; and 5,939,598. B-cells from these mice can be immortalized using standard techniques (e.g., by fusing with an immortalizing cell line such as a myeloma or by manipulating such B-cells by other techniques to perpetuate a cell line) to produce a monoclonal human antibody-producing cell. See, e.g., U.S. Pat. Nos. 5,916,771; 5,985,615.

Nucleic acid sequences (e.g., from cDNA libraries, isolated from human antibody producing mice, etc.) encoding desired antibodies can be cloned and further manipulated. For example, if the antibody is of non-human origin, it can be "immunized" for administration to patients. Methods for making chimeric, e.g., "humanized," antibodies are well known in the art, see e.g., U.S. Pat. Nos. 5,811,522; 5,789, 554; 5,861,155. Alternatively, recombinant antibodies can also be expressed by transient or stable expression vectors in mammalian, including human, cells and cell lines, as in Norderhaug (1997) J. Immunol. Methods 204:77–87; Boder (1997) Nat. Biotechnol. 15:553–557; see also U.S. Pat. No. 5,976,833. CHO cells lines that express "humanized" glycosylation patterns can be particularly useful, see, e.g., U.S. Pat. No. 5,272,070.

In one embodiment, the peptides of the invention are used as a pharmaceutical, immunogenic composition to generate an anti-GCA causative agent response in a human. Alternatively, DNA encoding a polypeptide comprising an immunogenic epitope can be administered as a pharmaceutical. The immunogenic compositions of the invention can generate a humoral (antibody) or cellular immune response.

Specific monoclonal and polyclonal antibodies and antisera will usually bind with a $K_D$ of at least about 1 $\mu$M, preferably at least about 0.1 $\mu$M or better, and most preferably, 0.01 $\mu$M or better.

Diagnosing Giant Cell Arteritis

The invention provides compositions and methods for diagnosing GCA involving the detection of GCA-associated polypeptides and nucleic acids in tissue samples (e.g., vasculitis lesion biopsies) and fluid samples (e.g., serum) from patients. GCA can also be diagnosed by detecting the presence of GCA-associated antibodies in serum or tissue samples from patients. These diagnostic methods are especially useful for the early diagnosis of GCA in the elderly. These procedures can also be used to follow the success of a treatment regimen and make prognoses.

Immunoassays

The invention provides reagents and methods using the polypeptides and peptides of the invention in a variety of antibody based assays. As discussed above, these assays are used to detect human antibodies in serum and tissues from patients to diagnose GCA. As the peptides and polypeptides of the invention can also be used to generate new antibodies for the diagnosis and treatment of GCA, these assays can be used to assess the generation, titer, isotype, etc., the antibodies of the invention.

Immunological binding methodologies are well known in the art; see also U.S. Pat. Nos. 4,366,241; 4,376,110; 4,517,288; 4,837,168; 5,817,470; METHODS IN CELL BIOLOGY Vol. 37, Antibodies in Cell Biology, Asai, ed. Academic Press, Inc. New York (1993); Sambrook, Stites; Silzel (1998) Clin. Chem. 44:2036–43; Rongen (1997) J. Immunol. Methods 204:105–133.; Hashida (1995) Biotechnol. Annu. Rev. 1:403–51; Bao (1997) J. Chromatogr. B. Biomed. Sci. Appl. 699:463–80; Self (1996) Curr. Opin. Biotechnol. 7:60–5.

In various embodiments of the invention, the polypeptides (or peptides) and antibodies of the invention are immobilized to the "capture" GCA-associated antibodies or polypeptides, respectively. Additional reagents are added to this reaction to detect any specific binding. These so-called "sandwich assays" are commercially usefull for detecting or isolating protein or antibodies.

Capture assays utilize a "capture" antibody or protein/ peptide (or nucleic acid in a hybridization variation) that is immobilized to a solid support. After adding a tissue or serum sample, a labeled "signal" molecule is added (typically in solution) that can bind to the captured reagent. The immobilized "capture" antibody or protein and the sample molecule and the "signal" molecule form a "sandwich" complex. To be effective, the signal nucleic acid or protein should not bind substantially with the capture antibody or protein. For example, a peptide or polypeptide of the invention is fixed to a solid support and contacted with a tissue or serum sample. GCA-associated antibodies, if present, will bind to the fixed reagent. Anti-human antibodies are then added to detect "captured" GCA-associated human antibodies. The sensitivity of the assay can be enhanced through use of a signal amplification system that multiplies the signal being detected. For example, an enhancing signal can be generated by attaching fluorescent, radioactive or enzymatic molecules to the anti-human antibody binding reagents (e.g., use of a goat F(ab')2 anti-human IgG-alkaline phosphatase). Use of enzymes and subsequent developing chemicals to enhance signals are commonly called "enzyme-linked immunosorbent assays, or, ELISAs. Other labels can include signal nucleic acid ligands that are bound to labeled antibodies, fluorophores, chemiluminescent agents, additional antibodies (e.g., Abs specific for a complex of a chelating agent and a metallic ion, e.g., a radionuclide) or other ligand-binding molecules (e.g., biotin) that can serve as specific binding pair members for a labeled ligand. Examples of radionuclides include, e.g., as $^3H$, $^{125}I$, $^{35}S$, $^{14}C$, or $^{32}P$ in labeled compositions. Examples of fluorochromes include, e.g., DAPI, fluorescein, Hoechst 33258, phycoerytlirin (PE), allophycocyanin (APC), R-phyeocyanin, B-phycoerythrin, R-phycoerythrin, rhodamine (e.g., tetra-methykhodamine isothiocyanate— TRITC), Texas red or lissamine. Suitable fluoresceins include, e.g., fluorescein isothiocyanate (FITC), (2-aminoethyl)-thioureido-fluorescein (FTED), fluorescein- thiosemicarbazide (FTSC), (2-aminoethyl)-ureido-fluorescein (FAMCO-E), erythrocin (tetra-iodo-fluorescein), and fluoresceinamine (FAM). A signal from the detectable reagent can be analyzed, for example, using a spectrophotometer to detect color from the chromogenic substrate; a radiation counter to detect radiation (as in an RIA), e.g., a gamma counter for detection of iodine-125; or a fluorometer to detect fluorescence in the presence of light of a certain wavelength. For detection of enzyme-linked reagents, a quantitative analysis can be made using a spectrophotometer, e.g., in the form of a microplate reader (e.g., Molecular Devices, Menlo Park, Calif.) in accordance with the manufacturer's instructions. Assays of the invention can be automated or performed robotically and signals from multiple samples can be detected simultaneously.

Immunoassays can be either competitive or noncompetitive. Noncompetitive immunoassays are assays in which the amount of captured analyte (GCA-associated human antibody) is directly measured. In one "sandwich" assay, for example, the capture agent (a polypeptide or peptide of the invention) can be bound directly to a solid substrate where they are immobilized. These immobilized reagents then capture antibody present in the test sample. The antibody thus immobilized is then bound by a labeling agent, such as a second anti-human antibody reagent bearing a label. Alternatively, the human antibody binding reagent can lack a label, but it may, in turn, be bound by a labeled third reagent (e.g. another antibody), e.g., specific to antibodies of the species from which the second antibody is derived. The second (or third) can be modified with a detectable moiety, such as biotin, to which another labeled molecule can specifically bind, such as, e.g., enzyme-labeled streptavidin. In a variation of the above, the immobilized reagent can be an antibody of the invention used to capture a GCA-associated polypeptide. The second (soluble) reagent can be, e.g., another GCA-associated polypeptide binding antibody of the invention. Competitive binding assays can also be used. For example, a known amount of labeled human antibody is added to the serum or tissue sample. The sample is then contacted with the capture agent (GCA-associated polypeptides or peptides of the invention). The amount of labeled human antibody bound to the immobilized reagent is inversely proportional to the concentration of GCA-polypeptide reactive antibody present in the sample. A hapten inhibition assay is another competitive assay.

These assays can be readily adapted to a variety of different variations, including automated analytical apparatus, of which many are well known in the art, see, e.g., U.S. Pat. Nos. 5,981,199; 5,958,202; 5,698,450; 5,648,274; 5,451,504; 5,424,220; 5,395,754; 5,175,086. See also U.S. Pat. Nos. 5,932,429; 5,780,319, 5,629,167; describing detecting and quantitation of specific human antibodies from tissue or serum samples.

The present invention also provides methods for Western blot (immunoblot) analysis to detect and/or quantify the presence of a protein in a sample. The technique generally comprises separating sample proteins by gel electrophoresis on the basis of molecular weight, transferring the separated proteins to a suitable solid support, (such as a nitrocellulose filter, a nylon filter, or derivatized nylon filter), and incubating the sample with the antibodies that specifically bind, e.g., GCA-associated polypeptides. These antibodies may be directly labeled or alternatively may be subsequently detected using labeled antibodies (e.g., labeled sheep anti-mouse antibodies.

The compositions and methods of the invention are also compatible with other assay formats, including liposome immunoassays (LIA) (Rongen (1997) *J. Immunol. Methods* 204:105–133), in which liposomes designed to bind specific molecules (e.g., antibodies or polypeptides) and release encapsulated reagents or markers are employed. The released a chemicals can be detected using standard techniques (see, e.g. Monroe (1986) *Amer. Clin. Prod. Rev.* 5:34).

Detecting GCA-Associated Nucleic Acid

GCA can also be diagnosed by detecting the presence of GCA-associated nucleic acid (e.g., the exemplary sequences of the invention, SEQ ID NO:1, SEQ ID NO:3, SEQ ID NO:5; SEQ ID NO:7; and SEQ ID NO:9 through 14.

One method for evaluating the presence or absence of GCA-associated DNA in a sample involves a Souther transfer. Briefly, the nucleic acid sample, such as digested DNA (e.g., genomic, cDNA) or mRNA, is run on agarose slab or polyacrylamide gels in buffer and transferred to membranes. Hybridization is carried out using nucleic acid probes. Nucleic acid probes can be, e.g., 10 to 20 to 30 or more bases or longer in length (see Sambrook for methods of selecting nucleic acid probe sequences for use in nucleic acid hybridization). Both quantitative and qualitative determination of the presence or absence of DNA or RNA encoding protein can be performed. Similarly, a Norther transfer can be used for the detection of GCA-associated mRNA. For example, mRNA is isolated from a given cell sample using an acid guanidinium-phenol-chloroform extraction method. The mRNA is then electrophoresed to separate the mRNA species and the mRNA is transferred from the gel to a nitrocellulose membrane. As with the Southern transfers, probes, such as labeled probes or PCR amplification products can be used to identify the presence or absence of GCA-associated nucleic acid.

Typically, oligonucleotide probes are labeled signal nucleic acids that are used to detect hybridization. Complementary probe nucleic acids or signal nucleic acids can be labeled by any means used to detect the presence of hybridized polynucleotides (typically, the same as labels on antibodies, as discussed above). Methods of detection can use labels for autoradiography or autofluorography, such as, e.g., $^3$H, $^{125}$I, $^{35}$S, $^{14}$C, or $^{32}$P-labeled probes or the like. Other labels include signal nucleic acid ligands that are bound to labeled antibodies, fluorophores, chemiluminescent agents, enzymes, and antibodies that can serve as specific binding pair members for a labeled ligand, as described above for antibody sandwich (e.g., ELISA) assays. Amplification (e.g., PCR) techniques (described above) can also be used to directly detect GCA-associated nucleic acids in situ or to amplify signals in capture assays.

Nucleic acid hybridization assays can also be performed in an array-based format; and the invention provides arrays comprising the nucleic acids of the invention. Arrays are a multiplicity of different "probe" or "target" nucleic acids (or other compounds) are hybridized against a target nucleic acid. In this manner a large number of different hybridization reactions can be run essentially "in parallel". This provides rapid, essentially simultaneous, evaluation of a wide number of reactants. Variations on arrays include, e.g., spectral imaging methods aimed at detecting and analyzing fluorescent in situ hybridizations employing numerous chromosome paints and/or loci specific probes, each labeled with a different fluorophore or a combination of fluorophores, see, e.g., U.S. Pat. No. 5,936,731. Methods of performing hybridization reactions in array based formats are well known to those of skill in the art, e.g., Jackson (1996) *Nature Biotechnology* 14:1685; Chee, *Science* 274:610 (1995); U.S. Pat. Nos: 6,004,755; 6,004,752; 5,631,134.

An alternative means for determining the level of expression of a gene encoding a protein is in situ hybridization. In situ hybridization assays are well known and are generally described in Angerer (1987) *Methods Enzymol* 152:649. In an in situ hybridization assay, cells are fixed to a solid support, typically a glass slide or analyzed by a fluorescence activated cell sorter (FACS). If DNA is to be probed, the cells are typically denatured with heat or alkali. The cells are then contacted with a hybridization solution at a moderate temperature to permit annealing of labeled probes specific to the nucleic acid sequence encoding the protein. The probes are typically labeled, ie., with radioisotopes or fluorescent reporters. See also U.S. Pat. No. 5,583,016; FISH fluorescence in situ hybridization, as described by Macechko (1997) *J Histochem Cytochem* 45:359–363; Raap (1995) *Hum Mol Genet* 4(4), 529–534.

Treating Giant Cell Arteritis

The invention provides compositions and methods for the prevention, treatment or amelioration of GCA. The therapeutic compositions of the invention can be administered as nucleic acids that can hybridize to GCA ausative nucleic acids in vivo (e.g., a nucleic acid from a GCA-causative microorganism) or an antibody of the invention reactive with a GCA-causative polypeptide.

Inhibitory Oligonucleotides

One particularly useful set of inhibitors provided by the present invention includes oligonucleotides which are able to either bind mRNA encoding GCA-causative nucleic acids or to their corresponding genes, in either case preventing or inhibiting the production of functional proteins involved in the pathogenesis of GCA. The inhibitory association can be though sequence specific hybridization to another nucleic acid or by general binding, as in an aptamer. In another embodiment, RNA can be targeted for cleavage by RNAaseP from eukaryotic cells (e.g., human RNAaseP) using a suitably designed antisense oligo-ribonucleotides as "external guide sequences" to form a hybrid with the target RNA, thereby creating a substrate for cleavage by RNAaseP in vitro; see e.g., U.S. Pat. No. ,5,624,824. One useful class of inhibitors includes oligonucleotides which cause inactivation or cleavage of mRNA. For example, the oligonucleotide is chemically modified or has enzyme activity which causes such cleavage of the mRNA, such as a ribozyme. Screening for effective oligonucleotides with the desired activity can be done by routine methods. Another useful class of inhibitors includes oligonucleotides which bind polypeptides. Double- or single-stranded DNA or single-stranded RNA molecules that bind to specific polypeptides targets are called "aptamers." The specific oligonucleotide-polypeptide association may be mediated by electrostatic interactions. For example, aptamers specifically bind to anion-binding exosites on thrombin, which physiologically binds to the polyanionic heparin (Bock (1992) *Nature* 355:564566). Screening for GCA polypeptide-binding aptamers also can be done by routine methods.

GCA-causative activity also can be inhibited by targeting the mRNA in vivo with antisense oligonucleotides. In some situations, naturally occurring nucleic acids used as antisense oligonucleotides may need to be relatively long (18 to 40 nucleotides) and present at high concentrations. A wide variety of synthetic, non-naturally occurring nucleotide and nucleic acid analogues are known which can address this potential problem. For example, protein-nucleic acids (PNAs) containing non-ionic backbones, such as N-(2-aminoethyl)glycine units can be used. Antisense oligonucleotides having phosphorothioate linkages can also be used, as described in WO 9710321 1; WO 96/39154; Mata (1997)

Toxicol Appl Pharmacol 144:189–197; Antisense Therapeutics, ed. Agrawal (Humana Press, Totowa, N.J., 1996). Antisense oligonucleotides having synthetic DNA backbone analogues provided by the invention can also include phosphoro-dithioate, methylphosphonate, phosphoranidate, alkyl phosphotriester, sulfamate, 3'-thioacetal, methylene(methylimino), 3'-N-carbamate, and morpholino carbamate nucleic acids. As with sequence effective for ribozyme activity, screening for effective antisense sequences can be done by routine screening, see, e.g., U.S. Pat. Nos. 5,580,967; 6,013,447.

Combinatorial chemistry methodology also can be used to create vast numbers of oligonucleotides that can be rapidly screened for specific oligonucleotides that have appropriate binding affinities and specificities toward any target, such as the GCA-causative proteins of the invention; see, e.g., U.S. Pat. Nos. 5,880,972; 5,792,431; 5,529,756; 5,503,805.

Inhibitory Ribozymes

Ribozymes are enzymatic RNA molecules capable of catalyzing the specific cleavage of RNA. The mechanism of ribozyme action involves sequence-specific hybridization of the ribozyme molecule to complementary target RNA, followed by endonucleolytic cleavage. Within the scope of the invention are engineered hammerhead motif ribozyme molecules that can specifically and efficiently catalyze endonucleolytic cleavage of the sequences encoding GCA-causative polypeptides.

Specific ribozyme cleavage sites within any potential RNA target are initially identified by scanning the target molecule for ribozyme cleavage sites which include the following sequences, GUA, GUU and GUC. Once identified, short RNA sequences of between 15 and 20 ribonucleotides corresponding to the region of the target gene containing the cleavage site may be evaluated for secondary structural features which may render the oligonucleotide inoperable. The suitability of candidate targets may also be evaluated by testing accessibility to hybridization with complementary oligonucleotides using ribonuclease protection assays.

Ribozymes act by binding to a target RNA through the target RNA binding portion of a ribozyme which is held in close proximity to an enzymatic portion of the RNA that cleaves the target RNA. Thus, the ribozyme recognizes and binds a target RNA through complementary base-pairing, and once bound to the correct site, acts enzymatically to cleave and inactivate the target RNA. Cleavage of a target RNA in such a manner will destroy its ability to direct synthesis of an encoded protein if the cleavage occurs in the coding sequence. After a ribozyne has bound and cleaved its RNA target, it is typically released from that RNA and so can bind and cleave new targets repeatedly.

The enzymatic ribozyme RNA molecule is able to cleave RNA and thereby inactivate a target RNA molecule. The complementarity functions to allow sufficient hybridization of the enzymatic ribozyme RNA molecule to the target RNA for cleavage to occur. Complementarity as low as 50–75% may also be employed. The present invention provides ribozymes targeting any portion of the coding region for a GCA-causative gene that cleave mRNA in a manner that will inhibit the translation of the mRNA.

The enzymatic ribozyme RNA molecule can be formed, e.g., in a hammerhead motif, but may also be formed in the motif of a hairpin, hepatitis delta virus, group I intron or RNaseP-like RNA (in association with an RNA guide sequence). Examples of such hammerhead motifs are described by Rossi (1992) *Aids Research and Human Retroviruses* 8:183; hairpin motifs by Hampel (1989) *Biochemistry* 28:4929, and Hampel (1990) *Nuc. Acids Res.* 18:299; the hepatitis delta virus motif by Perrotta (1992) *Biochemistry* 31:16; the RNaseP motif by Guerrier-Takada (1983) *Cell* 35:849; and the group I intron by Cech U.S. Pat. No. 4,987,071.

Preparation and Use of Inhibitory Nucleic Acids

Antisense molecules and ribozymes of the invention may be prepared by any method known in the art for the synthesis of RNA molecules. These include techniques for chemically synthesizing oligonucleotides such as solid phase phosphoramidite chemical synthesis. Alternatively, RNA molecules may be generated by in vitro and in vivo transcription of DNA sequences encoding the GCA-associated polypeptides of the invention. Such DNA sequences may be incorporated into a wide variety of vectors with suitable RNA polymerase promoters such as T7 or SP6. Alternatively, antisense cDNA constructs that synthesize antisense RNA constitutively or inducibly can be introduced into cell lines, cells or tissues.

RNA molecules can be modified to increase intracellular stability and half-life. Possible modifications include, but are not limited to, the addition of flanking sequences at the 5' and/or 3' ends of the molecule or the use of phosphorothioate or 2' O-methyl rather than phosphodiesterase linkages within the backbone of the molecule. This concept is inherent in the production of PNAs and can be extended in all of these molecules by the inclusion of nontraditional bases such as inosine, queosine and wybutosine as well as acetyl-, methyl-, thio- and similarly modified forms of adenine, cytidine, guanine, thynine, and uridine which are not as easily recognized by endogenous endonucleases.

Triplex DNA can also be used to inhibit DNA transcription and replication, generate site-specific mutations, cleave DNA, and induce homologous recombination. See, e.g., Havre (1993) *J. Virology* 67;7324–7331; Scanlon (1995) *FASEB J.* 9:1288–1296; Giovannangeli (1996) *Biochemistry* 35:10539–10548; Chan (1997) *J. Mol. Medicine (Berlin)* 75: 267–282. Triple helix DNAs can be used to target the same sequences identified for antisense regulation.

Methods for introducing vectors into cells or tissues include those methods that are suitable for in vivo, in vitro and ex vivo therapy, as described below.

Antibodies for Treating GCA

In addition to providing antibodies reactive with GCA-associated polypeptides useful for diagnosing GCA, the invention also provides antibodies reactive with GCA-cusative polypeptides for the amelioration, prevention or treatment of GCA. Administration of antibodies can be as polypeptides or as nucleic acids encoding antibodies; such methods and protocols are well known in the art.

Formulation and Administration Pharmaceuticals

The invention provides antibodies (directed to GCA-causative proteins, e.g., SEQ ID NO:2, SEQ ID NO:4, SEQ ID NO:6, SEQ ID NO:8), vectors or oligonucleotides (e.g., inhibitory nucleic acids, e.g., antisense) with pharmaceutically acceptable carrier (excipient) to form a pharmacological composition. The nucleic acids and vectors can be formulated as pharmaceuticals for the transfer of nucleic acids into cells in vitro or in vivo. The pharmaceutical composition of the invention can further comprise other active agents, including other recombinant viruses, plasmids, naked DNA or pharmaceuticals (e.g., anti-inflammatory agents).

These pharmaceuticals can be administered by any means in any appropriate formulation. Routine means to determine drug regimens and formulations to practice the methods of the invention are well described in the patent and scientific literature, and some illustrative examples are set forth below. For example, details on techniques for formulation, dosages, administration and the like are well described in the scientific and patent literature, see, e.g., the latest edition of Remington's Pharmaceutical Sciences, Maack Publishing Co, Easton Pa.

Pharmaceutically acceptable carriers can contain a physiologically acceptable compound that acts, e.g., to stabilize the composition or to increase or decrease the absorption of the agent and/or pharmaceutical composition. Physiologically acceptable compounds can include, for example, carbohydrates, such as glucose, sucrose, or dextrans, antioxidants, such as ascorbic acid or glutathione, chelating agents, low molecular weight proteins, compositions that reduce the clearance or hydrolysis of any co-administered agents, or excipients or other stabilizers and/or buffers. Detergents can also be used to stabilize the composition or to increase or decrease the absorption of the pharmaceutical composition (see infra for exemplary detergents).

Other physiologically acceptable compounds include wetting agents, emulsifying agents, dispersing agents or preservatives that are particularly useful for preventing the growth or action of microorganisms. Various preservatives are well known, e.g., ascorbic acid. One skilled in the art would appreciate that the choice of a pharmaceutically acceptable carrier, including a physiologically acceptable compound depends, e.g., on the route of administration of the adenoviral preparation and on the particular physio-chemical characteristics of any co-administered agent.

The compositions for administration will commonly comprise a buffered solution comprising nucleic acid (e.g., vector) or antibody in a pharmaceutically acceptable carrier, e.g., an aqueous carrier. A variety of carriers can be used, e.g., buffered saline and the like. These solutions are sterile and generally free of undesirable matter. These compositions may be sterilized by conventional, well-known sterilization techniques. The compositions may contain pharmaceutically acceptable auxiliary substances as required to approximate physiological conditions such as pH adjusting and buffering agents, toxicity adjusting agents and the like, for example, sodium acetate, sodium chloride, potassium chloride, calcium chloride, sodium lactate and the like. The concentration of active agent in these formulations can vary widely, and will be selected primarily based on fluid volumes, viscosities, body weight and the like in accordance with the particular mode of administration selected and the patient's needs.

Determining Dosing Regimens

The pharmaceutical formulations of the invention can be administered in a variety of unit dosage forms, depending upon the particular condition or disease, the general medical condition of each patient, the method of administration, and the like. In one embodiment, the concentration of vectors (e.g., therapeutic virus or plasmids) in the pharmaceutically acceptable excipient is between about $10^3$ to about $10^{18}$ or between about $10^5$ to about $10^{15}$ or between about $10^6$ to about $10^{13}$ particles/vectors per mL in an aqueous solution. Details on dosages are well described in the scientific and patent literature, see, e.g., the latest edition of Remington's Pharmaceutical Sciences; Sterman (1998) Hum. Gene Ther. 9:1083–1092; Smith (1997) Hum. Gene Ther. 8:943–954.

The exact amount and concentration of antibody or vector or oligonucleotide and the amount of formulation in a given dose, or the "therapeutically effective dose" is determined by the clinician, as discussed above. The dosage schedule, i.e., the "dosing regimen," will depend upon a variety of factors, e.g., the stage and severity of the GCA, and the general state of the patient's health, physical status, age and the like. The state of the art allows the clinician to determine the dosage regimen for each individual patient and, if appropriate, concurrent disease or condition treated. For example, adenovirus has been safely used for many years for human vaccines; see, e.g., Horwitz (1990) supra; Straus (1984) supra; Haj-Ahmad (1986) J. Virol., 57:267); Ballay (1985) EMBO, 4, 3861(1985); PCT patent application WO 94117832). Human adenoviruses have been used in humans as in vivo gene delivery vehicles (Graham & Prevec in New Approaches to Immunological Problems, Ellis (ed), Butterworth-Heinemann, Boston, Mass., pp. 363–390 (1992); Ragot (1993) Nature 361:647–650 (1993); Kozarsky (1993) Curr. Opin. Genet. Dev. 3:499–503); U.S. Pat. No. 5,981,225. These illustrative examples can also be used as guidance to determine the dosage regiment, i.e., dose schedule and dosage levels administered when practicing the methods of the invention.

Single or multiple administrations of antibody, vector or oligonucleotide formulation can be administered, depending on the dosage and frequency as required and tolerated by the patient. Thus, one typical dosage for regional (e.g., IP or intrathecal) administration is between about 0.5 to about 50 mL of a formulation with about $10^{13}$ vectors/particles per mL. In an alternative embodiment, dosages are from about 5 mL to about 20 mL are used of a formulation with about $10^9$ vectors/particles per mL. Lower dosages can be used, such as is between about 1 mL to about 5 mL of a formulation with about $10^6$ vectors/particles particles per mL. Based on objective and subjective criteria, as discussed herein, any dosage can be used as required and tolerated by the patient.

The exact concentration of antibodies, vector or oligonucleotide, the amount of formulation, and the frequency of administration can also be adjusted depending on the levels of in vivo (e.g., in situ) gene expression and vector retention after an initial administration.

Routes of Delivery

The pharmaceutical compositions of the invention (e.g., therapeutic antibodies, vectors or antisense oligonucleotides) can be delivered by any means known in the art systemically (e.g., intravenously), regionally, or locally (e.g., intra- or peri-tumoral or intracystic injection, e.g., to treat bladder cancer) by, e.g., intraarterial, intratumoral, intravenous (IV), parenteral, intra-pleural cavity, topical, oral, or local administration, as subcutaneous, intra-tracheal (e.g., by aerosol) or transmucosal (e.g., buccal, bladder, vaginal, uterine, rectal, nasal mucosa), intra-tumoral (e.g., transdermal application or local injection). For example, intra-arterial injections can be used to have a "regional effect," e.g., to focus on a specific organ (e.g., brain, liver, spleen, lungs), for example, intra-hepatic artery injection or intra-carotid artery injection. If it is desired to deliver the preparation to the brain, it can be injected into a carotid artery or an artery of the carotid system of arteries (e.g., occipital artery, auricular artery, temporal artery, cerebral artery, maxillary artery, etc.).

Therapeutic antibodies, vectors or other nucleic acids of the present invention, alone or in combination with other suitable components can be made into aerosol formulations to be administered via inhalation. These aerosol formulations can be placed into pressurized acceptable propellants, such as dichlorodifluoromethane, propane, nitrogen, and the like. They also may be formulated as pharmaceuticals for non-pressured preparations such as in a nebulizer or an atomizer. Typically such administration is in an aqueous pharmacologically acceptable buffer as described above.

Delivery to the lung can be also accomplished, e.g., by use of a bronchoscope.

Additionally, the therapeutic compositions employed in the present invention may be made into suppositories by mixing with a variety of bases such as emulsifying bases or water-soluble bases, Formulations suitable for vaginal administration may be presented as pessaries, tampons, creams, gels, pastes, foams, or spray formulas.

The pharmaceutical formulations of the invention can be presented in unit-dose or multi-dose sealed containers, such as ampules and vials, and can be stored in a freeze-dried (lyophilized) condition requiring only the addition of the sterile liquid excipient, for example, water, for injections, immediately prior to use. Extemporaneous injection solutions and suspensions can be prepared from sterile powders, granules, and tablets.

Therapeutic compositions can also be administered in a lipid formulation, more particularly either complexed with liposomes to for lipid/nucleic acid complexes (e.g., as described by Debs and Zhu (1993) WO 93/24640; Mannino (1988) supra; Rose, U.S. Pat No. 5,279,833; Brigham (1991) WO 91/06309; and Felgner (1987) supra) or encapsulated in liposomes, as in immunoliposomes directed to specific cells. It will be appreciated that such lipid formulations can also be administered topically, systemically, or delivered via aerosol.

Kits

The invention provides kits that contain the vectors or pharmaceutical compositions of the invention. The kits can contain, e.g., vectors able to produce antisense sequences to inhibit causative agents of GCA. The kit can contain instructional material teaching methodologies, e.g., means to diagnose GCA or biopsy arteritis lesions. Kits containing pharmaceutical preparations (e.g., vectors, nucleic acids) can include directions as to indications, dosages, routes and methods of administration, and the like.

It is understood that the examples and embodiments described herein are for illustrative purposes only and that various modifications or changes in light thereof will be suggested to persons skilled in the art and are to be included within the spirit and purview of this application and scope of the appended claims.

EXAMPLES

The following examples are offered to illustrate, but not to limit the claimed invention.

Example 1

Isolation and Characterization of Sequences Associated With GCA

The following example describes the isolation and identification of the novel sequences of the invention by subtractive hybridization of nucleic acid of normal tissue from nucleic acid of GCA lesions.

Because of advances in techniques of representational difference analysis (RDA), this method was chosen to detect unique sequences ih samples of normal versus GCA-associated DNA. This method can identify sequences from pathogenic organisms, latent or active, in tissue lesion samples in addition to genomic losses or rearrangements. After isolation, nucleic acid from an involved site is compared to DNA obtained from uninvolved tissue. RDA represents a powerful tool in which differences between complex genomes can be identified. Recent modifications in the technique permit the analysis of minute samples from small cell numbers.

A genomic (rather than RNA expression) strategy was selected in order to decrease the accrual of inflammation-associated host genes, such as cytokines or T cell associated polypeptides, as T cell receptors (TCRs). Genomic RDA systematically excludes the majority of "host" (i.e., patients') genes and permits identification of sequences from any GCA-associated microorganism with a DNA phase to its life-cycle.

Like other subtractive strategies, RDA critically depends on optimal positive ("GCA-involved" or "lesional" or "tester") and negative ("norm" or "non-lesional" or "driver") starting material. Since temporal artery lesions in GCA are discontinuous, the ideal pair of tester and driver areas can be present in biopsies from single individuals. A microscopic-scale laser microdissection isolation method was used to obtain homogeneous lesional and non-lesional samples. This is a flexible and direct method for isolating microscopic-scale samples for molecular analysis. Lasercapture microdissection was used to isolate DNA from archival pathology specimens of GCA-positive arteries from both histopathologically involved and uninvolved areas. Genomic RDA was performed on archival, GCA-positive temporal arteries that were snap-frozen. These specimens provided a source of high quality genomic DNA. Specimens that were selected for RDA unequivocally demonstrated pathologic evidence of GCA.

Thirty sequentially cut tissue sections (10 $\mu$m each) were placed on non-charged microscope slides, fixed, dehydrated, and stained with hematoxylin and eosin. GCA inflammatory lesions were identified and dissected using a Laser Capture Microdissecting Microscope™ (Arcturus Engineering, Inc., Mountain View, Calif.). Approximately 500 cells including giant cells and inflammatory infiltrate were dissected from each GCA specimen. DNA isolated from these cells represented the "tester" population. Approximately 500 cells were microdissected from a subsequent section with no histopathologic evidence of GCA lesions. The DNA isolated from these cells represented the "driver" sample in the RDA.

DNA was extracted from tester and driver samples and prepared for RDA according to Michiels (1998) supra. Briefly, isolated cells were incubated overnight at 37° C. in proteinase K and restriction digested with BamHI. The driver and tester DNA were ligated to amplimers RBAM14 and RBAM24 and PCR amplified as described by Lisitsyn (1993) supra and Michiels (1998) supra. RDA was performed using the lesional DNA as the tester and non-lesional DNA as the driver in consecutive rounds of hybridization/amplification to obtain sequences represented solely in the lesional DNA population.

The fourth round of RDA yielded two prominent bands. This entire region of the gel encompassing these prominent bands was excised and the DNA was extracted and cloned into a TA vector (Invitrogen, San Diego, Calif.). Bacteria were transformed with the vector and 100 individual clones containing insert were isolated. The 100 clones were examined for insert by PCR amplification. Eighty percent of the clones contained insert. Analysis of these clones revealed multiple inserts of unique size.

Priority candidate genes within the two RDA libraries were identified using several steps. First, duplicate clones were excluded by DNA fragment size and by 4-cutter restriction pattern. Second, unique cloned inserts were analyzed by automated sequencing. Third, the sequences were used to search the National Institutes of Health non-redundant database with the NCBI BLAST program (BLOSUM 62 matrix, TBLASTX (version 1.4.11, November 1997) as described by Alschul (1996) Methods Enzymol. 266:460–480. Alignments were performed using the CLUSTAL W Multiple Sequence Alignment Program (version 1.7, June, 1997).

One criterion for selecting which genes would first be translated into recombinant polypeptides and used to analyze for the presence of human antibodies in serum from GCA patients was relative homology to sequences of known microbial origin. A total of eleven unique DNA sequences were obtained in the first two RDAs using two different GCA+ arterial specimens. Sequence identity analysis showed that four of the unique sequences, GCA1, GCA5, GCA14, and GCA17, may be distantly related to known microbial sequences. Thus, these were the first sequences selected for further characterization.

Example 2

Serum Antibodies From GCA Patients Specifically Bind to Polypeptides of the Invention The following example demonstrates that antibodies in the serum of GCA patients specifically bind to exemplary polypeptides of the invention.

Validation of GCA-associated gene segments relies, in part, on functional evaluations of either the presence of disease-specific immune responses against the associated candidate protein sequence or disease-specific expression of the gene sequence or product. In order to proceed with analysis of the novel sequences of the invention, open reading frames from these sequences were analyzed and expression constructs produced.

These unique sequences GCA1, GCA5, GCA14, and GCA17, as identified in Example 1, were analyzed for open reading frames (ORF). A total of five ORFs from four sequences were identified. These were used to construct fusion proteins to identify the presence of anti-GCA1, GCA5, GCA14, and GCA17 antibodies in human GCA patients. The sequence of the fusion proteins is set forth, above.

GST fusion proteins were produced using these five identified ORFs from the clones identified by genomic RDA. Each ORF was amplified using sequence specific primers designed to produce an in-frame product when cloned into the multiple cloning site of an expression vector, pGEX-KG, as described by Guan (1991) Anal. Biochem. 192:262–267. The BL21 strain of *E. coli* (Stratagene, San Diego, Calif.) was transformed with the desired pGEX-GCA construct. Individual colonies were selected, grown, and its sequence confirmed as the correct insertion of one in-frame fragment copy. Individual colonies were selected, grown, and expression of fusion protein was induced with IPTG using standard techniques. GST (glutathione S-transferase)-GCA fusion proteins were produced and purified using the GST Gene fusion System (Pharmacia Biotech) and manufacturer's instructions. Briefly, the bacterial cells were lysed by sonication and the soluble GST fusion proteins allowed to bind to a glutathione Sepharose 4B column. Purified GST-fusion proteins were eluted from the column and protein concentration determined by the Bradford method. Several of the GST-GCA fusion proteins were insoluble and localized to the inclusion bodies. These proteins were retrieved by isolation of the inclusion body followed by Solubilization of the recombinant proteins in the inclusion bodies. Purity was estimated at greater than 90% by SDS-PAGE and protein (Coomassie) stain. Reactivity of the expected product was determined by Western blot analysis using a commercially available anti-GST antibody (Molecular Probes). The GST-GCA fusion proteins were then evaluated for GST reactivity to human serum.

The protocol for large-scale GST-fusion protein purification was:

Day 1:
1. Pick colony from plate (LB-agar plate with 0.05 mg amp/ml) plated from glycerol stocks. Grow in 5ml LB-amp o/n shaking at 37° C.

Day 2:
2. Preparation of Beads (in morning): 950 mg of G4510 Sigma Glutathione Agarose Beads in 20 ml PBS. Rock for 2 hrs at room temperature (r.t.). Store at 4° C. Warm to room temperature to prepare the column.
3. Preparation of (1 ml) Columns): Prepare quiagen column with slurry to produce a 1 ml packed column. Equilibrate column in Bugbuster+125 µl 1M DTT+2 complete tablets (Boehringer)+50 µl 250 mM PMSF (50 mM final concentration).
4. In morning—transfer 5 ml culture into 600 ml LB-amp and continue shaking at 37° C. Grow until OD reading (at 600 nm) is 0.6–0.8.
5. Induce w/1 µl of 100 mM IPTG per ml of culture. at r.t. shaking vigorously for ~1½ hrs.
6. Centrifuge at 5,000×g for 10 min. Decant and remove as much liquid as possible, leaving pellet.
7. Resuspend pellets in Bugbuster (Novagen, 705844) (¹/₂₅ th volume of the original culture volume). Prepare 25 ml Bugbuster+125 µl of 1M DTT (5 mM DTT final), 2 complete tabs (Boehringer)+50 µl of 250 mM PMSF (0.5 mM final PMSF conc.); store on ice. Add 12 ml of Bugbuster mix to each pellet and vortex.
8. Incubate centrifuge tubes at r.t shaking at slow setting for 10 min.
9. Transfer each 12 ml soup to a 30 ml small autoclaved centriuge tube. Spin at 16,000×g for 20 min. at 4° C.
10. Apply supernatant to prepared columns. Wash Buffers: Wash 1: 50 mM Tris-Cl, pH 7.5; 300 mM NaCl; 10 mM EDTA; complete tablet 0.5 mM PMSF. Wash 2: Above buffer, without NaCl. Elution Buffer: 50 mM Tris-Cl, pH 8, 25 mM reduced glutathione.
11. Uncap columns and collect flow thru.
12. Wash each column in 2×6 mi wash 1
13. Wash each column in 2×6 ml wash 2
14. Cap columns and add 2 ml of elution buffer. (Can store in 4° C. at this stage.)
15. Elute in 500 µl 1 mL, and finally 2 ml of elution buffer. Check OD of each.
16. Quantify protein concentration by Bradford method
16. Store eluted protein fractions in −20° C. or −80° C.

GST Fusion Protein ELISA Testing

ELISA analyses were performed for primary detection of human serum antibodies with specificity for the GST-GCA fusion proteins. The GST fusion proteins (purified as noted above) and a GST protein were purified as a control. Microtiter plates were coated with a GST-GCA fusion protein or GST control; 1 µg/well in 50 µL borate coating buffer (5.15 g of boric acid, 3.65 g NaCl, per 500 ml, pH 8.5; washed, 3× with 0.05% Tween20-PBS, and blocked with 0.05% Tween20-PBS.

Human sera was tested in triplicate at multiple dilutions in 0.05% Tween20-PBS. Reactivity was detected with an alkaline-phosphatase-labeled goat anti-human IgG and developed with Sigma 104 phosphatase substrate. Absorbances were measured at 405 nm with a Biorad ELISA reader and Macintosh analytic software. OD values of nonspecific binding of sera to GST alone were subtracted from the raw values of binding to the GST-GCA fusion proteins in order to determine specific absorbances.

FIG. 1 illustrates data from a representative ELISA using the fusion protein GCA1b-GST to test human serum for the presence of anti-GCA1b reactive antibodies. Various dilutions of human serum from a GCA+ patient and GCA− individual were used, as shown in FIG. 1. Specific binding of human antibodies to GCA1b was detected in the patient's serum (note enhanced serum binding to the GCA+ serum, as compared to GCA−, or "normal" serum).

Figure 2:
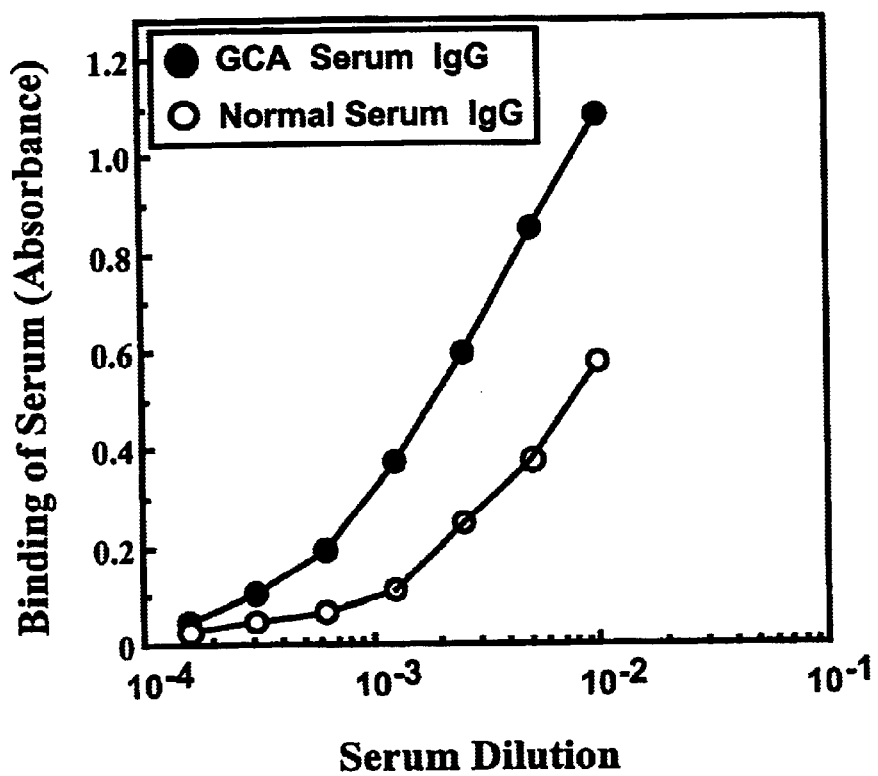
FIG. 2 illustrates a representative experiment using the fusion protein GCA17-GST in serum ELISA using various dilution of human serum from a GCA+ and GCA− individual and detecting for bound human IgG.

FIG. 2 illustrates data from a representative ELISA using the fusion protein GCA17-GST to test human serum for the presence of anti-GCA17 reactive antibodies. Various dilutions of human serum from a GCA+ patient and a GCA− individual were used, as shown in FIG. 2. Specific binding of human antibodies to GCA17 was detected in the patient's serum (note enhanced serum binding to the GCA+ serum, as compared to GCA−, or "normal" serum).

Figure 3:
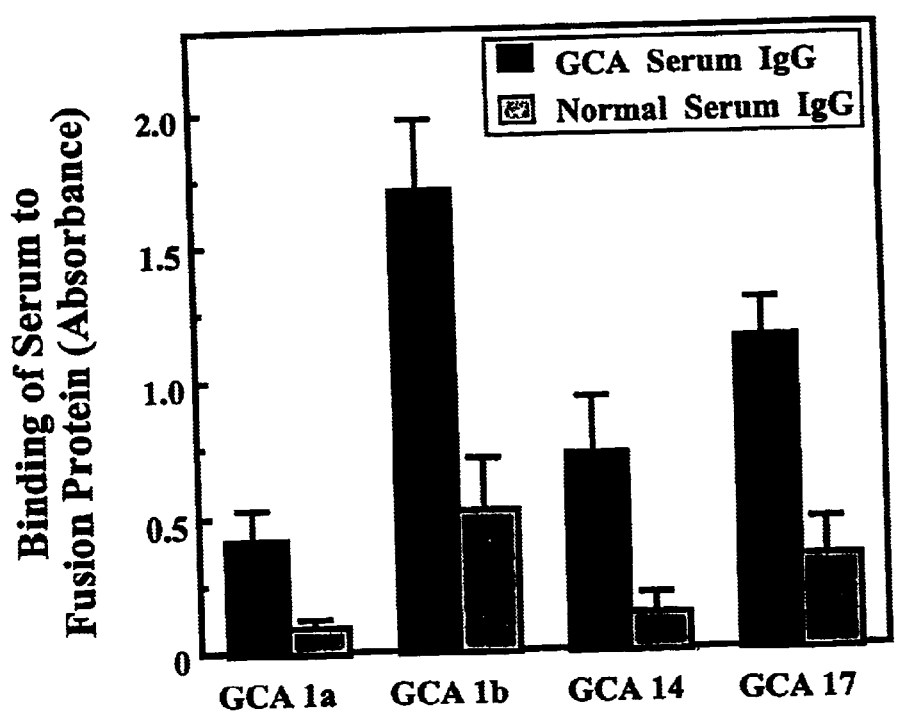
FIG. 3 illustrates a representative experiment using four exemplary GCA-GST fusion proteins, GCA1a-GST, GCA1b-GST, GCA14-GST, and GCA17-GST. These fusion proteins were used to detect serum IgG in sera from 10 GCA+ and 10 GCA− individuals.

FIG. 3 illustrates a representative experiment using four exemplary GCA-GST fusion proteins, GCA1a-GST, GCA1b-GST, GCA14-GST, and GCA17GST. These fusion proteins were used to detect serum IgG in sera from 10 GCA+ patients and 10 GCA− individuals. All sera were individually tested at multiple dilutions. The graph demonstrates the mean OD observed after 30 minutes of detection and the standard deviation for binding of each of the fusion proteins to the sera at 1/100 dilution.

These data demonstrate that the peptides and polypeptides of the invention can be used to identity antibodies present in the serum of GCA+ patients. Accordingly, these compositions and associated methods of the invention can be used to diagnose, and, importantly, to screen for, the presence or predisposition to GCA.

These data also demonstrate that the peptides and polypeptides of the invention can be used to generate additional antibodies (the antibodies of the invention) to further identify the predisposition to or presence of GCA. These antibodies can also be used to treat GCA, as described above.

Because these data demonstrate that the peptides and polypeptides of the invention are associated with GCA, they also demonstrate that the nucleic acids of the invention also can be used to diagnose GCA. As these nucleic acids also encode polypeptides possibly essential to the GCA-causative agent, these data also demonstrate that the nucleic acids of the invention also can be used to treat GCA, as described above.

What is claimed is:

1. An isolated or recombinant nucleic acid consisting of SEQ ID NO:3, or its complement.

2. An isolated or recombinant nucleic acid encoding the polypeptide consisting of SEQ ID NO:4, or its complement.

3. An expression vector comprising an isolated or recombinant nucleic acid of claim 1 operably linked to a promoter in the sense orientation.

4. An expression vector comprising an isolated or recombinant nucleic acid of claim 2 operably linked to a promoter in the sense orientation.

5. A transformed cell comprising the isolated or recombinant nucleic acid of claim 1.

6. A transformed cell comprising the isolated or recombinant nucleic acid of claim 2.

7. A transformed cell comprising the expression vector of claim 3.

8. A transformed cell comprising the expression vector of claim 4.

9. A heterologous nucleic acid comprising the isolated or recombinant nucleic acid of claim 1.

10. A heterologous nucleic acid comprising the isolated or recombinant nucleic acid of claim 2.

11. A nucleic acid probe consisting of 20 to 30 or more contiguous nucleotides of the isolated or recombinant nucleic acid of claim 1.

12. A nucleic acid probe consisting of greater than 50 contiguous nucleotides of the isolated or recombinant nucleic acid of claim 1.

13. A nucleic acid probe consisting of about 15 to about 200 contiguous nucleotides of the isolated or recombinant nucleic acid of claim 1.

14. A nucleic acid probe consisting of about 25 to about 100 contiguous nucleotides of the isolated or recombinant nucleic acid of claim 1.

15. A nucleic acid probe consisting of about 35 to about 75 contiguous nucleotides of the isolated or recombinant nucleic acid of claim 1.

16. A kit for detecting the presence of nucleic acid sequences associated with giant cell arteritis comprising at least one of the following:
(a) an isolated or recombinant nucleic acid consisting of SEQ ID NO:3, or its complement;
(b) an isolated or recombinant nucleic acid encoding the polypeptide consisting of SEQ ID NO:4, or its complement;
(c) a nucleic acid consisting of 20 to 30 or more contiguous nucleotides of the isolated or recombinant nucleic acid of (a);
(d) a nucleic acid consisting of greater than 50 contiguous nucleotides of the isolated or recombinant nucleic acid of (a);
(e) a nucleic acid consisting of about 15 to about 200 contiguous nucleotides of the isolated or recombinant nucleic acid of (a);
(f) a nucleic acid consisting of about 25 to about 100 contiguous nucleotides of the isolated or recombinant nucleic acid of (a); or
(g) a nucleic acid consisting of about 35 to about 75 contiguous nucleotides of the isolated or recombinant nucleic acid of (a);
and instructional material.

17. A method for diagnosing giant cell arteritis comprising
providing a nucleic acid sample from an arteritis lesion biopsy,
transferring the nucleic acid sample to a membrane, contacting the membrane with at least one nucleic acid probe selected from the group consisting of
(a) an isolated or recombinant nucleic acid consisting of SEQ ID NO:3, or its complement;
(b) an isolated or recombinant nucleic acid encoding the polypeptide consisting of SEQ ID NO:4, or its complement;
(c) a nucleic acid consisting of 20 to 30 or more contiguous nucleotides of the isolated or recombinant nucleic acid of (a);
(d) a nucleic acid consisting of greater than 50 contiguous nucleotides of the isolated or recombinant nucleic acid of (a);
(e) a nucleic acid consisting of about 15 to about 200 contiguous nucleotides of the isolated or recombinant nucleic acid of (a);
(f) a nucleic acid consisting of about 25 to about 100 contiguous nucleotides of the isolated or recombinant nucleic acid of (a); or
(g) a nucleic acid consisting of about 35 to about 75 contiguous nucleotides of the isolated or recombinant nucleic acid of (a);
and detecting whether the nucleic acid probe hybridizes to the nucleic acid sample on the membrane; wherein specific hybridization is diagnostic for giant cell arteritis.

18. A method for diagnosing giant cell arteritis or predisposition for giant cell arteritis in a subject comprising
obtaining a nucleic acid sample from the subject,
contacting the nucleic acid sample with at least one nucleic acid probe selected from the group consisting of
(a) an isolated or recombinant nucleic acid consisting of SEQ ID NO:3, or its complement;
(b) an isolated or recombinant nucleic acid encoding the polypeptide consisting of SEQ ID NO:4, or its complement;
(c) a nucleic acid consisting of 20 to 30 or more contiguous nucleotides of the isolated or recombinant nucleic acid of (a);
(d) a nucleic acid consisting of greater than 50 contiguous nucleotides of the isolated or recombinant nucleic acid of (a);
(e) a nucleic acid consisting of about 15 to about 200 contiguous nucleotides of the isolated or recombinant nucleic acid of (a);
(f) a nucleic acid consisting of about 25 to about 100 contiguous nucleotides of the isolated or recombinant nucleic acid of (a); or
(g) a nucleic acid consisting of about 35 to about 75 contiguous nucleotides of the isolated or recombinant nucleic acid of (a);
and detecting whether the nucleic acid probe hybridizes to the nucleic acid sample; wherein specific hybridization is diagnostic for giant cell arteritis or predisposition to giant cell arteritis.

* * * * *

SEQUENCE LISTING

```
<160> NUMBER OF SEQ ID NOS: 98

<210> SEQ ID NO 1
<211> LENGTH: 682
<212> TYPE: DNA
<213> ORGANISM: Homosapiens
<220> FEATURE:
<223> OTHER INFORMATION: artificially generated nucleic acid

<400> SEQUENCE: 1 gatcccgct  ttcgcgggga  tgacagcggt  actcaattca  cgcgcagcga  tgccagcgaa        60
ctaaacggag  gatctcacga  acatccgctc  caacccgac   accacgctcc  ccgccgtcac      120
gacaggctcg  ctgccctcct  cgcgcaagtt  ctttgcaatc  cctgaggccg  cgcccgacat      180
ccgcgttccc  ttgcgcgaga  tcatcctgtc  cgagggcgcc  ggcgagccga  acctgccggt      240
ctatgacacc  tcgggcccct  acaccgatcc  ggccgtgacg  atcgacgtca  acagcggcct      300
gccgcgcaat  cgcctcgcct  gggtcaagga  acgcggcggc  gtcgaggaat  atcaggccgc      360
accatcaagc  cggaggacaa  cggcaatgtc  ggcgcatccc  acgccgccaa  ggcgttcacc      420
ggcaccacaa  gccgctgcgc  ggctcgacgg  cacaagatca  cccactcgag  ttcgccgcgc      480
cggcattata  ccaaggagat  gatctacgtc  gccgagcgtg  agaatcttgg  cgcaagcagc      540
agctgagcgc  gccgaggccg  gctgccgacg  gaagagtttt  ggcgccgcgg  tgccggctta      600
ttacgccgga  atttgtcgca  agagatcgcg  cggcggccat  tatttccttt  aaaattaaca      660
ttgccgagct  tgaaccgatg  aa                                                  682

<210> SEQ ID NO 2
<211> LENGTH: 92
<212> TYPE: PRT
<213> ORGANISM: Homosapiens

<400> SEQUENCE: 2

Leu Pro Ala Val Thr Thr Gly Ser Leu Pro Ser Ser Arg Lys Phe Phe
1               5                   10                  15
```

```
Ala Ile Pro Glu Ala Ala Pro Asp Ile Arg Val Pro Leu Arg Glu Ile
            20                  25                  30

Ile Leu Ser Glu Gly Ala Gly Glu Pro Asn Leu Pro Val Tyr Asp Thr
        35                  40                  45

Ser Gly Pro Tyr Thr Asp Pro Ala Val Thr Ile Asp Val Asn Ser Gly
    50                  55                  60

Leu Pro Arg Asn Arg Leu Ala Trp Val Lys Glu Arg Gly Gly Val Glu
65                  70                  75                  80

Glu Tyr Gln Ala Ala Pro Ser Ser Arg Arg Thr Thr
                85                  90
```

<210> SEQ ID NO 3
<211> LENGTH: 501
<212> TYPE: DNA
<213> ORGANISM: Homosapiens
<220> FEATURE:
<223> OTHER INFORMATION: Synthetically generated nucleic acid

<400> SEQUENCE: 3

```
actctccagc ctctcaccga ggatgaagtc ggctcgtgaa gtggttgcgg tcggggggcaa     60
aacccgggac gagctggcct tcctgccggc cgccctcgaa attgtcgaga cgccgccatc    120
tcccaccgcg agactcacgg ccgccttgct tgctgccttg ttctactgcg ccgtggcgtg    180
ggcgggtctc ggcaggatcg acatcgttgc ttctgcatcc agaaagatcg tgccgggcga    240
ccgtgtaaag ctggttcagc cgctcgaggt cggcgtggtg cgggccactc atgtccgcga    300
tggccaaacc gtcaaggccg gcgagattct gatcgagctg gatccattcg cgggtggtgt    360
ggatgttgcg ccccgtcaga ggtccatcac ggtgtcggcg ccccacggat cgccacacca    420
tcttgtcgac ctttcttcac cgacgagtca ccgccgagtt gccgatattg cgtgatctta    480
tcagaatgcg gcgatgatca t                                               501
```

<210> SEQ ID NO 4
<211> LENGTH: 124
<212> TYPE: PRT
<213> ORGANISM: Homosapiens

<400> SEQUENCE: 4

```
Leu Ser Ser Leu Ser Pro Arg Met Lys Ser Ala Arg Glu Val Val Ala
1               5                   10                  15

Val Gly Gly Lys Thr Arg Asp Glu Leu Ala Phe Leu Pro Ala Ala Leu
            20                  25                  30

Glu Ile Val Glu Thr Pro Pro Ser Pro Thr Ala Arg Leu Thr Ala Ala
        35                  40                  45

Leu Leu Ala Ala Leu Phe Tyr Cys Ala Val Ala Trp Ala Gly Leu Gly
    50                  55                  60

Arg Ile Asp Ile Val Ala Ser Ala Ser Arg Lys Ile Val Pro Gly Asp
65                  70                  75                  80

Arg Val Lys Leu Val Gln Pro Leu Glu Val Gly Val Val Arg Ala Thr
                85                  90                  95

His Val Arg Asp Gly Gln Thr Val Lys Ala Gly Glu Ile Leu Ile Glu
            100                 105                 110

Leu Asp Pro Phe Ala Gly Gly Val Asp Val Ala Thr
        115                 120
```

<210> SEQ ID NO 5
<211> LENGTH: 747

-continued

```
<212> TYPE: DNA
<213> ORGANISM: Homosapiens
<220> FEATURE:
<223> OTHER INFORMATION: Artificially generated nucleic acid

<400> SEQUENCE: 5
accgacgtcg actatccatg aacggatccc tgcaacgaca tcgtgcgtac ggcctatgaa      60
gcgctcgccg ccgtgctcgg tggcacgcag tcgctccaca ccaactcgtt cgacgaggcg     120
atcgcgctgc cgattgactt ctccgcccgg atcgcccgca acaccagctg atccagcagc     180
acgagacaga cgtcacggac gcggtcgaca ctctggcggg gtcctactac gtggagcgcc     240
tgacggatga cctcgccaag cgggcctggg agctgatgga agaggtcgag aagatgggtg     300
gcatggcgca ggcgatcgcg accggttggc cgaagcgcct gatcgagcaa tctgcgacgc     360
aaaagcaggc cgcgatcgat cgcggcgatc aggtgatcgt gggcgtgaac cgctaccggc     420
ccgaacagga gcaaccgatc gacattattg agatcgacaa ctcgacggtt cgggcctccc     480
agatccggtg tctcgccgaa atcgaaaagg cgcgtgattc aaggaaggtt gagtccgcgc     540
tcggggagct ggcgtgtatt gcccgcacgg gtgagggaaa tctgctggct gcagcgaccg     600
agcccgctcg cgcgcgggct accgtcgggg agatgtccga cgccatgcgg caagcattcg     660
gcgaccacga ggcggtgccg gaggtagtgt cggacgttta cggccgtgcc tatggcacgg     720
atccgttcat ggatagtcga cgtcggt                                         747

<210> SEQ ID NO 6
<211> LENGTH: 48
<212> TYPE: PRT
<213> ORGANISM: Homosapiens

<400> SEQUENCE: 6

Asp Pro Cys Asn Asp Ile Val Arg Thr Ala Tyr Glu Ala Leu Ala Ala
1               5                   10                  15

Val Leu Gly Gly Thr Gln Ser Leu His Thr Asn Ser Phe Asp Glu Ala
            20                  25                  30

Ile Ala Leu Pro Ile Asp Phe Ser Ala Arg Ile Ala Arg Asn Thr Ser
        35                  40                  45

<210> SEQ ID NO 7
<211> LENGTH: 301
<212> TYPE: DNA
<213> ORGANISM: Homosapiens
<220> FEATURE:
<223> OTHER INFORMATION: Synthetically generated nucleic acid

<400> SEQUENCE: 7
actctccagc ctctcaccga ggatcatcga cgacattaag cagctggccg acaacggcgt      60
gcgcgaattc acgctgatcg gacagaatgt caacgcctac cacggcggag ggcccgacgg     120
ccgcgtctgg ccgctcggca aattgctgca gcgactcgcg gacattccag gcgtcatgcg     180
gctgcgttat tcgatcagcc atccgcgcga cgtcgacgac agcctgatcg ccgcgcatcg     240
cgatttgccc ggactgatgc cgttcgtgca cctgccggtg caatcggggg cggaccggat     300
c                                                                     301

<210> SEQ ID NO 8
<211> LENGTH: 91
<212> TYPE: PRT
<213> ORGANISM: Homosapiens

<400> SEQUENCE: 8
```

-continued

```
Ile Ile Asp Asp Ile Lys Gln Leu Ala Asp Asn Gly Val Arg Glu Phe
1               5                   10                  15
Thr Leu Ile Gly Gln Asn Val Asn Ala Tyr His Gly Gly Pro Asp
            20                  25                  30
Gly Arg Val Trp Pro Leu Gly Lys Leu Leu Gln Arg Leu Ala Asp Ile
            35                  40                  45
Pro Gly Val Met Arg Leu Arg Tyr Ser Ile Ser His Pro Arg Asp Val
    50                  55                  60
Asp Asp Ser Leu Ile Ala Ala His Arg Asp Leu Pro Gly Leu Met Pro
65                  70                  75                  80
Phe Val His Leu Pro Val Gln Ser Gly Ala Asp
                85                  90
```

<210> SEQ ID NO 9
<211> LENGTH: 620
<212> TYPE: DNA
<213> ORGANISM: Homosapiens
<220> FEATURE:
<221> NAME/KEY: misc_feature
<222> LOCATION: (0)...(0)
<223> OTHER INFORMATION: N=A,T,C or G

<400> SEQUENCE: 9

| | | | | | |
|---|---|---|---|---|---|
| actctccanc | ctctcaccga | ggatcagaat | aggtgaagag | cgaagacacc | gagaacgtct | 60 |
| ggccttgaac | ggacagcgtg | cttgagttgg | tcggggtcac | caccggaccc | gtgtccaccg | 120 |
| gcgcagtcac | ngtgaaagca | cttgaccatg | atcccagacg | gtgccgtcat | ccgcgcggac | 180 |
| ccacancgtn | tccgcgcccg | accggattga | tagctcagcg | acaccagctg | ggctgccgtg | 240 |
| acgtanttgt | gctggttngg | tgcaagtgcc | accccgctca | agacaaantg | gccgcacctg | 300 |
| tgcccgtgtc | ccaaacgtca | tattgggtcg | cagcactgtc | gaacggatca | ctgtangtgc | 360 |
| acagcgacna | anccgcatan | ctctngccgt | ggggcgcaac | gatgttnnac | accgtctcaa | 420 |
| cgggtaccgt | gtcnagggga | ncatttacng | ggaaagcatt | cgaccactcc | cccacaccgt | 480 |
| gcccgcattt | gcgccgattc | ctttcattga | tatgtccacg | tcggtnggnc | tttaagcngg | 540 |
| cggcaaccgc | ggtgnagctn | cacttttttgt | tccttttatt | ganggttaat | ttgcgcgctt | 600 |
| tggncgtaan | tntttngaan | | | | | 620 |

<210> SEQ ID NO 10
<211> LENGTH: 662
<212> TYPE: DNA
<213> ORGANISM: Homosapiens
<220> FEATURE:
<221> NAME/KEY: misc_feature
<222> LOCATION: (0)...(0)
<223> OTHER INFORMATION: N=A,T,C or G

<400> SEQUENCE: 10

| | | | | | |
|---|---|---|---|---|---|
| gatccgacca | gcaatcaggc | ggagctgcag | cacctgaaaa | acgaccttct | ctcggcactg | 60 |
| ctgggtattt | cacgcaaccg | ctctgcgctt | ggcgggaaac | accgacgcgc | ttgaaggctt | 120 |
| accggacgac | acgccgccag | ccttgattcg | aatgcatctg | gagtacttgc | gcagtcagga | 180 |
| ttccgagcag | cgcgccaagc | tgtccgaact | ggatcagcaa | cgggtgcaga | aggtcgcgga | 240 |
| gaccaggacg | atcgacgcca | gcatcgcgaa | gattgaagct | ttgctgcggt | gctgcaggan | 300 |
| cgggtcgggg | ttcgcaagta | cctggcggac | agggagtacg | gctcaaagct | gcaatattcg | 360 |
| caggaactcc | aggaactggt | cgggatgcag | caggacatcc | tggtgcaacg | gagcaaagct | 420 |

-continued

```
cgaggaaacc aatgcggntt gtcgccgcac ttcgacgaaa acccgcggna agcttcgtct      480
nngaataacc ggcacccgnc tgttccnacg atcttggccc aagggggacgc aaaaaagggc    540 cggcaagncc tcaaaggacc aagggngttt taaaanccga gcacccggga cccaaccttt    600
aaaaancntt ggcggcccccc attcgacggn gtggnggcaa caaattgggc cgngcccat    660 tt                                                                     662
```

<210> SEQ ID NO 11
<211> LENGTH: 242
<212> TYPE: DNA
<213> ORGANISM: Homosapiens
<220> FEATURE:
<221> NAME/KEY: misc_feature
<222> LOCATION: (0)...(0)
<223> OTHER INFORMATION: N=A,T,C or G

<400> SEQUENCE: 11

```
actctcnngc ctctcaccga agatagccgg caaggactgg cgngaacann gcgcgctgga      60
ctatcnctaa agggtctccn acnacgtcca nccggacnag ctgacctcgt ttccncnaag    120
cgtgaaactg aaggccggtg aaaccntcnt gttcgcctng atcacctact agtcgcgcgc    180
cnngcgcgac aggatcaacg ccaaggtgat ggccgatccc cgcctggcgt cgtcgatgga    240
tc                                                                     242
```

<210> SEQ ID NO 12
<211> LENGTH: 552
<212> TYPE: DNA
<213> ORGANISM: Homosapiens

<400> SEQUENCE: 12

```
gatccgctcg atgcccaggc ccagtacagc gaactgttcg cccatggccg cgccacgtca      60
ctgttgctat tcgaacatgt tcacggtgaa tcccgtgacc gcggccaggc gatggtggac    120
ctgctggcgc agtacgagca gcacggtttg cagttaaaca gccgcgaatt accggaccac    180
ctgccgctgt atctggagta cctgtcgcag ctgccgcaag gcgaagccgt ggaaggtttg    240
aaagatatcg cgccgattct ggcattgctg agcgcgcgtc tgcaacagcg tgaaagccgt    300
tatgccgtga tgtttgatct gctgctgaaa ttggccgata ccgctatcga cagcgacaaa    360
gtggcggaaa aaattgccga cgaagcgcgc gatgatacgc cgcaggcgct ggatgctgtt    420
tgggaagaag agcaggttaa attctttgct gacaaaggct gcggcgattc agcaatcact    480
gctcatcagc gtcgctttgc cggtgccgtc gcgccgcaat atctgaatat cctcggtgag    540
aggctggaga gt                                                         552
```

<210> SEQ ID NO 13
<211> LENGTH: 265
<212> TYPE: DNA
<213> ORGANISM: Homosapiens
<220> FEATURE:
<221> NAME/KEY: misc_feature
<222> LOCATION: (0)...(0)
<223> OTHER INFORMATION: N=A,T,C or G

<400> SEQUENCE: 13

```
gatcctnaca cantagcccg tggacgcatt tgcgtcgacc ctcatangga agcgatacga      60
ggcgggtnaa agtgaacatc cgccgagcac ggcagcgacg cctccgctca ccgtcngcgc    120
agtacttcct cgggtcgccg cgcctagcac tctgcgccgt gacatcaanc cgtgaaccca    180
cgggagactt tgcgccgcna agggatgagt ccactattag atgacgcatg gctacgagcc    240
```

```
natcctcggt ganaagctgg agagt                                           265

<210> SEQ ID NO 14
<211> LENGTH: 317
<212> TYPE: DNA
<213> ORGANISM: Homosapiens
<220> FEATURE:
<221> NAME/KEY: misc_feature
<222> LOCATION: (0)...(0)
<223> OTHER INFORMATION: N=A,T,C or G

<400> SEQUENCE: 14
gatccggccn cgcacganct taccggtnaa aacttccncn ccnataatat ttgccgcgcg      60
agccgccctg angctctcgg cgtaactccg gatgcacggg ggaccgtgac ggttgtantg     120
ccctggcttt tctcagcnga aatctgcaca gccatcttcc gatcgatctg cgcaggtgg     180 ggcggcncaa aacggtgggc atctccaaac cgcaggaacg tgttttgcag gatgtcgaac    240
atcatccacg cttcggtncc caacggctac ttcgcccggt accgggccat gtcatcctcg    300
gtganaagct gganant                                                   317

<210> SEQ ID NO 15
<211> LENGTH: 341
<212> TYPE: DNA
<213> ORGANISM: Homosapiens
<220> FEATURE:
<221> NAME/KEY: misc_feature
<222> LOCATION: (0)...(0)
<223> OTHER INFORMATION: N=A,T,C or G

<400> SEQUENCE: 15
actctccagc ctcgcaccga ggatcagggc gtcgtcgact ccgtcgacct gaccgcctcc     60
ccnccgctgc tctcgatcgg cggccagacc tacaccancg acgtagatca agcgcgtggt    120
gcgcggcgcn acnagcanca nctaantcaa ggcctcgctg catcccgcca atccagcgct    180
cagcttcgcg ggaattgcgc gancgctttt gcgcgtcncg agtnaccgca tacacacctg    240
ccgtccctgc gaaagcaagg acccatactc cgcngcgggt gttgttgacg ggactcgtca    300
tggcggcaac gcacaacgtn naacttctgt ggttatggat c                        341

<210> SEQ ID NO 16
<211> LENGTH: 256
<212> TYPE: DNA
<213> ORGANISM: Homosapiens
<220> FEATURE:
<221> NAME/KEY: misc_feature
<222> LOCATION: (0)...(0)
<223> OTHER INFORMATION: N=A,T,C or G

<400> SEQUENCE: 16
gatccgcgca tcctctctgt ggctctcgcg gggtcagagg tggataaggc cggccgcaag     60
ctcggacttc ccgtcncaat cnaaggcttc tgcgatcncc antacaacta cnacggcaat    120
ctnacatcac gcaagatcgc angctcngtc atcaaggacg cngcggtcnc cncccggcag    180
gtgctcnata tngtgttgaa naacaccatc gctcctgcaa cggcaagaag atcacatgca    240
aggtccactc gctgtg                                                    256

<210> SEQ ID NO 17
<211> LENGTH: 701
<212> TYPE: DNA
<213> ORGANISM: Homosapiens
<220> FEATURE:
```

-continued

<223> OTHER INFORMATION: N = A, T, C or G

<400> SEQUENCE: 17

```
gatccccgct tcgcgggga tgacagcggt actcaattca cgcgcagcga tgccagcgaa      60
ctaaacggag gatctcacga acatccgctc caaccccgac accacgctcc ccgccgtcac    120
gacaggctcg ctgccctcct cgcgcaagtt ctttgcaatc cctgaggccg cgcccgacat    180
ccgcgttccc ttgcgcgaga tcatcctgtc cgagggcgcc ggcgagccga acctgccggt    240
ctatgacacc tcgggcccct acaccgatcc ggccgtgacg atcgacgtca acagcggcct    300
gccgcgcaat cgcctcgcct gggtcaagga acgcggcggc gtcgaggaat atcanggccg    360
caccatcaag ccggaggaca acggcaatgt cggcgcatcc cacgccgcca aggcgttcac    420
cgngcaccac aagccgctgc gcggnctcga cggcacaaga tcacccactc gagttcgccg    480
cgccggcatt ataccaagga gatgatctac gtcgccgagc gtgagaatct tggncgcaag    540
cagcagctng agcgcgccga nggccggctn gccgacggna agagttttgg cgccgcggtg    600
ccggncttna ttacgccgga atttgtncgc aangagatcg ncgcggncgn gccattattt    660
cctttnaaaa ttaancattg ccgagcttga accgatgaan n                       701
```

<210> SEQ ID NO 18
<211> LENGTH: 511
<212> TYPE: DNA
<213> ORGANISM: Homosapiens
<220> FEATURE:
<223> OTHER INFORMATION: N=A,T,C or G

<400> SEQUENCE: 18

```
actctccagc ctctcaccga ggatgaagtc ggctcgtgaa gtggttgcgg tcgggggcaa      60
aacccgggac gagctggcct tcctgccggc cgccctcgaa attgtcgaga cgccgccatc    120
tcccaccgcg agactcacgg ccgccttgct tgctgccttg ttctactgcg ccgtggcgtg    180
ggcgggtctc ggcaggatcg acatcgttgc ttctgcatcc agaaagatcg tgccgggcga    240
ccgtgtaaag ctggttcagc cgctcgaggt cggcgtggtg cgggccactc atgtccgcga    300
tggccaaacc gtcaaggccg gcgagattct gatcgagctg gatccattcg cgggtggtgt    360
ggatgttgcg ccccgtcnag aggtccatca cggtgtcggc gccccancgg atcgccacac    420
catcttgtcg acctnttctt caccgacgan gtcaccgccg agttgccgat attgcgntga    480
tcttantcan gaanntgcgg ncgatgatca t                                  511
```

<210> SEQ ID NO 19
<211> LENGTH: 620
<212> TYPE: DNA
<213> ORGANISM: Homosapiens
<220> FEATURE:
<221> NAME/KEY: CDS
<222> LOCATION: (1)...(618)
<223> OTHER INFORMATION: N= A, T, C or G
    Xaa= any amino acid
<223> OTHER INFORMATION: Synthetically generated nucleic acid

<400> SEQUENCE: 19

```
act ctc can cct ctc acc gag gat cag aat agg tga aga gcg aag aca      48
Thr Leu Xaa Pro Leu Thr Glu Asp Gln Asn Arg  *  Arg Ala Lys Thr
 1               5                  10                  15 ccg aga acg tct ggc ctt gaa cgg aca gcg tgc ttg agt tgg tcg ggg      96
Pro Arg Thr Ser Gly Leu Glu Arg Thr Ala Cys Leu Ser Trp Ser Gly
            20                  25                  30 tca cca ccg gac ccg tgt cca ccg gcg cag tca cng tga aag cac ttg     144
```

```
Ser Pro Pro Asp Pro Cys Pro Pro Ala Gln Ser Xaa *   Lys His Leu
            35              40                  45 acc atg atc cca gac ggt gcc gtc atc cgc gcg gac cca can cgt ntc         192
Thr Met Ile Pro Asp Gly Ala Val Ile Arg Ala Asp Pro Xaa Arg Xaa
            50              55                  60 cgc gcc cga ccg gat tga tag ctc agc gac acc agc tgg gct gcc gtg         240
Arg Ala Arg Pro Asp *   *   Leu Ser Asp Thr Ser Trp Ala Ala Val
            65              70                  75 acg tan ttg tgc tgg ttn ggt gca agt gcc acc ccg ctc aag aca aan         288
Thr Xaa Leu Cys Trp Xaa Gly Ala Ser Ala Thr Pro Leu Lys Thr Xaa
            80              85                  90 tgg ccg cac ctg tgc ccg tgt ccc aaa cgt cat att ggg tcg cag cac         336
Trp Pro His Leu Cys Pro Cys Pro Lys Arg His Ile Gly Ser Gln His
            95              100                 105 tgt cga acg gat cac tgt ang tgc aca gcg acn aan ccg cat anc tct         384
Cys Arg Thr Asp His Cys Xaa Cys Thr Ala Thr Xaa Pro His Xaa Ser
            110             115                 120 ngc cgt ggg gcg caa cga tgt tnn aca ccg tct caa cgg gta ccg tgt         432
Xaa Arg Gly Ala Gln Arg Cys Xaa Thr Pro Ser Gln Arg Val Pro Cys
125             130                 135                 140 cna ggg gan cat tta cng gga aag cat tcg acc act ccc cca cac cgt         480
Xaa Gly Xaa His Leu Xaa Gly Lys His Ser Thr Thr Pro Pro His Arg
            145             150                 155 gcc cgc att tgc gcc gat tcc ttt cat tga tat gtc cac gtc ggt ngg         528
Ala Arg Ile Cys Ala Asp Ser Phe His *   Tyr Val His Val Gly Xaa
            160             165                 170 nct tta agc ngg cgg caa ccg cgg tgn agc tnc act ttt tgt tcc ttt         576
Xaa Leu Ser Xaa Arg Gln Pro Arg Xaa Ser Xaa Thr Phe Cys Ser Phe
            175             180                 185 tat tga ngg tta att tgc gcg ctt tgg ncg taa ntn ttt nga                 618
Tyr *   Xaa Leu Ile Cys Ala Leu Trp Xaa *   Xaa Phe Xaa
            190             195 an                                                                      620
```

<210> SEQ ID NO 20
<211> LENGTH: 199
<212> TYPE: PRT
<213> ORGANISM: Homosapiens
<220> FEATURE:
<223> OTHER INFORMATION: Xaa= any amino acid
<223> OTHER INFORMATION: Frame shift sequence

<400> SEQUENCE: 20

```
Thr Leu Xaa Pro Leu Thr Glu Asp Gln Asn Arg Arg Ala Lys Thr Pro
1               5                   10                  15

Arg Thr Ser Gly Leu Glu Arg Thr Ala Cys Leu Ser Trp Ser Gly Ser
            20                  25                  30

Pro Pro Asp Pro Cys Pro Pro Ala Gln Ser Xaa Lys His Leu Thr Met
            35                  40                  45

Ile Pro Asp Gly Ala Val Ile Arg Ala Asp Pro Xaa Arg Xaa Arg Ala
        50                  55                  60

Arg Pro Asp Leu Ser Asp Thr Ser Trp Ala Val Thr Xaa Leu Cys
65                  70                  75                  80

Trp Xaa Gly Ala Ser Ala Thr Pro Leu Lys Thr Xaa Trp Pro His Leu
            85                  90                  95

Cys Pro Cys Pro Lys Arg His Ile Gly Ser Gln His Cys Arg Thr Asp
            100                 105                 110

His Cys Xaa Cys Thr Ala Thr Xaa Pro His Xaa Ser Xaa Arg Gly Ala
        115                 120                 125
```

```
Gln Arg Cys Xaa Thr Pro Ser Gln Arg Val Pro Cys Xaa Gly Xaa His
    130                 135                 140

Leu Xaa Gly Lys His Ser Thr Thr Pro Pro His Arg Ala Arg Ile Cys
145                 150                 155                 160

Ala Asp Ser Phe His Tyr Val His Val Gly Xaa Xaa Leu Ser Xaa Arg
                165                 170                 175

Gln Pro Arg Xaa Ser Xaa Thr Phe Cys Ser Phe Tyr Xaa Leu Ile Cys
            180                 185                 190

Ala Leu Trp Xaa Xaa Phe Xaa
        195

<210> SEQ ID NO 21
<211> LENGTH: 620
<212> TYPE: DNA
<213> ORGANISM: Homosapiens
<220> FEATURE:
<221> NAME/KEY: CDS
<222> LOCATION: (2)...(619)
<223> OTHER INFORMATION: N= A, T, C or G
      Xaa= any amino acid
<223> OTHER INFORMATION: Synthetically generated nucleic acid

<400> SEQUENCE: 21 a ctc tcc anc ctc tca ccg agg atc aga ata ggt gaa gag cga aga cac      49
  Leu Ser Xaa Leu Ser Pro Arg Ile Arg Ile Gly Glu Glu Arg Arg His
  1               5                   10                  15 cga gaa cgt ctg gcc ttg aac gga cag cgt gct tga gtt ggt cgg ggt        97
Arg Glu Arg Leu Ala Leu Asn Gly Gln Arg Ala  *  Val Gly Arg Gly
              20                  25                  30 cac cac cgg acc cgt gtc cac cgg cgc agt cac ngt gaa agc act tga       145
His His Arg Thr Arg Val His Arg Arg Ser His Xaa Glu Ser Thr  *
            35                  40                  45 cca tga tcc cag acg gtg ccg tca tcc gcg cgg acc cac anc gtn tcc       193
Pro  *  Ser Gln Thr Val Pro Ser Ser Ala Arg Thr His Xaa Val Ser
              50                  55                  60 gcg ccc gac cgg att gat agc tca gcg aca cca gct ggg ctg ccg tga       241
Ala Pro Asp Arg Ile Asp Ser Ser Ala Thr Pro Ala Gly Leu Pro  *
            65                  70                  75 cgt ant tgt gct ggt tng gtg caa gtg cca ccc cgc tca aga caa ant       289
Arg Xaa Cys Ala Gly Xaa Val Gln Val Pro Pro Arg Ser Arg Gln Xaa
          80                  85                  90 ggc cgc acc tgt gcc cgt gtc cca aac gtc ata ttg ggt cgc agc act       337
Gly Arg Thr Cys Ala Arg Val Pro Asn Val Ile Leu Gly Arg Ser Thr
        95                  100                 105 gtc gaa cgg atc act gta ngt gca cag cga cna anc cgc ata nct ctn       385
Val Glu Arg Ile Thr Val Xaa Ala Gln Arg Xaa Xaa Arg Ile Xaa Leu
    110                 115                 120 gcc gtg ggg cgc aac gat gtt nna cac cgt ctc aac ggg tac cgt gtc       433
Ala Val Gly Arg Asn Asp Val Xaa His Arg Leu Asn Gly Tyr Arg Val
125                 130                 135                 140 nag ggg anc att tac ngg gaa agc att cga cca ctc ccc cac acc gtg       481
Xaa Gly Xaa Ile Tyr Xaa Glu Ser Ile Arg Pro Leu Pro His Thr Val
              145                 150                 155 ccc gca ttt gcg ccg att cct ttc att gat atg tcc acg tcg gtn ggn       529
Pro Ala Phe Ala Pro Ile Pro Phe Ile Asp Met Ser Thr Ser Val Gly
            160                 165                 170 ctt taa gcn ggc ggc aac cgc ggt gna gct nca ctt ttt gtt cct ttt       577
Leu  *  Ala Gly Gly Asn Arg Gly Xaa Ala Xaa Leu Phe Val Pro Phe
            175                 180                 185 att gan ggt taa ttt gcg cgc ttt ggn cgt aan tnt ttn gaa               619
```

```
Ile Xaa Gly  *  Phe Ala Arg Phe Gly Arg Xaa Xaa Xaa Glu
        190              195                 200
``` n                                                                    620

<210> SEQ ID NO 22
<211> LENGTH: 200
<212> TYPE: PRT
<213> ORGANISM: Homosapiens
<220> FEATURE:
<223> OTHER INFORMATION: Xaa= any amino acid
<223> OTHER INFORMATION: Frame shift sequence

<400> SEQUENCE: 22

```
Leu Ser Xaa Leu Ser Pro Arg Ile Arg Ile Gly Glu Glu Arg His
1           5                   10                  15

Arg Glu Arg Leu Ala Leu Asn Gly Gln Arg Ala Val Gly Arg Gly His
            20                  25                  30

His Arg Thr Arg Val His Arg Ser His Xaa Glu Ser Thr Pro Ser
        35                  40                  45

Gln Thr Val Pro Ser Ser Ala Arg Thr His Xaa Val Ser Ala Pro Asp
        50                  55                  60

Arg Ile Asp Ser Ser Ala Thr Pro Ala Gly Leu Pro Arg Xaa Cys Ala
65                  70                  75                  80

Gly Xaa Val Gln Val Pro Pro Arg Ser Arg Gln Xaa Gly Arg Thr Cys
                85                  90                  95

Ala Arg Val Pro Asn Val Ile Leu Gly Arg Ser Thr Val Glu Arg Ile
                100                 105                 110

Thr Val Xaa Ala Gln Arg Xaa Xaa Arg Ile Xaa Leu Ala Val Gly Arg
            115                 120                 125

Asn Asp Val Xaa His Arg Leu Asn Gly Tyr Arg Val Xaa Gly Xaa Ile
130                 135                 140

Tyr Xaa Glu Ser Ile Arg Pro Leu Pro His Thr Val Pro Ala Phe Ala
145                 150                 155                 160

Pro Ile Pro Phe Ile Asp Met Ser Thr Ser Val Gly Leu Ala Gly Gly
                165                 170                 175

Asn Arg Gly Xaa Ala Xaa Leu Phe Val Pro Phe Ile Xaa Gly Phe Ala
            180                 185                 190

Arg Phe Gly Arg Xaa Xaa Xaa Glu
            195                 200
```

<210> SEQ ID NO 23
<211> LENGTH: 620
<212> TYPE: DNA
<213> ORGANISM: Homosapiens
<220> FEATURE:
<221> NAME/KEY: CDS
<222> LOCATION: (3)...(620)
<223> OTHER INFORMATION: N= A, T, C or G
      Xaa= any amino acid
<223> OTHER INFORMATION: Synthetically generated nucleic acid

<400> SEQUENCE: 23

```
ac tct cca ncc tct cac cga gga tca gaa tag gtg aag agc gaa gac      47
   Ser Pro Xaa Ser His Arg Gly Ser Glu  *  Val Lys Ser Glu Asp
    1           5                   10 acc gag aac gtc tgg cct tga acg gac agc gtg ctt gag ttg gtc ggg     95
Thr Glu Asn Val Trp Pro  *  Thr Asp Ser Val Leu Glu Leu Val Gly
 15              20                  25 gtc acc acc gga ccc gtg tcc acc ggc gca gtc acn gtg aaa gca ctt    143
Val Thr Thr Gly Pro Val Ser Thr Gly Ala Val Thr Val Lys Ala Leu
```

```
                                                                    -continued
         30                    35                    40                   45
gac cat gat ccc aga cgg tgc cgt cat ccg cgc gga ccc aca ncg tnt        191
Asp His Asp Pro Arg Arg Cys Arg His Pro Arg Gly Pro Thr Xaa Xaa
                50                    55                    60 ccg cgc ccg acc gga ttg ata gct cag cga cac cag ctg ggc tgc cgt        239
Pro Arg Pro Thr Gly Leu Ile Ala Gln Arg His Gln Leu Gly Cys Arg
                65                    70                    75 gac gta ntt gtg ctg gtt ngg tgc aag tgc cac ccc gct caa gac aaa        287
Asp Val Xaa Val Leu Val Xaa Cys Lys Cys His Pro Ala Gln Asp Lys
                80                    85                    90 ntg gcc gca cct gtg ccc gtg tcc caa acg tca tat tgg gtc gca gca        335
Xaa Ala Ala Pro Val Pro Val Ser Gln Thr Ser Tyr Trp Val Ala Ala
            95                   100                   105 ctg tcg aac gga tca ctg tan gtg cac agc gac naa ncc gca tan ctc        383
Leu Ser Asn Gly Ser Leu Xaa Val His Ser Asp Xaa Xaa Ala Xaa Leu
110                  115                   120                   125 tng ccg tgg ggc gca acg atg ttn nac acc gtc tca acg ggt acc gtg        431
Xaa Pro Trp Gly Ala Thr Met Xaa Xaa Thr Val Ser Thr Gly Thr Val
                130                   135                   140 tcn agg gga nca ttt acn ggg aaa gca ttc gac cac tcc ccc aca ccg        479
Ser Arg Gly Xaa Phe Thr Gly Lys Ala Phe Asp His Ser Pro Thr Pro
                145                   150                   155 tgc ccg cat ttg cgc cga ttc ctt tca ttg ata tgt cca cgt cgg tng        527
Cys Pro His Leu Arg Arg Phe Leu Ser Leu Ile Cys Pro Arg Arg Xaa
                160                   165                   170 gnc ttt aag cng gcg gca acc gcg gtg nag ctn cac ttt ttg ttc ctt        575
Xaa Phe Lys Xaa Ala Ala Thr Ala Val Xaa Leu His Phe Leu Phe Leu
            175                   180                   185 tta ttg ang gtt aat ttg cgc gct ttg gnc gta ant ntt tng aan            620
Leu Leu Xaa Val Asn Leu Arg Ala Leu Xaa Val Xaa Xaa Xaa Xaa
190                  195                   200

<210> SEQ ID NO 24
<211> LENGTH: 204
<212> TYPE: PRT
<213> ORGANISM: Homosapiens
<220> FEATURE:
<223> OTHER INFORMATION: Xaa= any amino acid
<223> OTHER INFORMATION: Frame shift sequence

<400> SEQUENCE: 24

Ser Pro Xaa Ser His Arg Gly Ser Glu Val Lys Ser Glu Asp Thr Glu
1               5                   10                  15

Asn Val Trp Pro Thr Asp Ser Val Leu Glu Leu Val Gly Val Thr Thr
            20                  25                  30

Gly Pro Val Ser Thr Gly Ala Val Thr Val Lys Ala Leu Asp His Asp
        35                  40                  45

Pro Arg Arg Cys Arg His Pro Arg Gly Pro Thr Xaa Xaa Pro Arg Pro
    50                  55                  60

Thr Gly Leu Ile Ala Gln Arg His Gln Leu Gly Cys Arg Asp Val Xaa
65                  70                  75                  80

Val Leu Val Xaa Cys Lys Cys His Pro Ala Gln Asp Lys Xaa Ala Ala
                85                  90                  95

Pro Val Pro Val Ser Gln Thr Ser Tyr Trp Val Ala Ala Leu Ser Asn
            100                 105                 110

Gly Ser Leu Xaa Val His Ser Asp Xaa Xaa Ala Xaa Leu Xaa Pro Trp
        115                 120                 125

Gly Ala Thr Met Xaa Xaa Thr Val Ser Thr Gly Thr Val Ser Arg Gly
    130                 135                 140
```

-continued

```
Xaa Phe Thr Gly Lys Ala Phe Asp His Ser Pro Thr Pro Cys Pro His
145                 150                 155                 160

Leu Arg Arg Phe Leu Ser Leu Ile Cys Pro Arg Arg Xaa Xaa Phe Lys
                165                 170                 175

Xaa Ala Ala Thr Ala Val Xaa Leu His Phe Leu Phe Leu Leu Leu Xaa
                180                 185                 190

Val Asn Leu Arg Ala Leu Xaa Val Xaa Xaa Xaa Xaa
                195                 200
```

<210> SEQ ID NO 25
<211> LENGTH: 619
<212> TYPE: DNA
<213> ORGANISM: Homosapiens
<220> FEATURE:
<223> OTHER INFORMATION: N= A,T,C or G
<223> OTHER INFORMATION: Synthetically generated nucleic acid
<223> OTHER INFORMATION: Reverse strand

<400> SEQUENCE: 25

```
nttcnaaana nttacgncca aagcgcgcaa attaaccntc aataaaagga acaaaaagtg      60
nagctncacc gcggttgccg ccngcttaaa gnccaccga cgtggacata tcaatgaaag     120
gaatcggcgc aaatgcgggc acggtgtggg ggagtggtcg aatgctttcc cngtaaatgn    180
tcccctngac acggtacccg ttgagacggt gtnnaacatc gttgcgcccc acggcnagag    240
ntatgcggnt tngtcgctgt gcacntacag tgatccgttc gacagtgctg cgacccaata    300
tgacgtttgg gacacgggca caggtgcggc cantttgtct tgagcgggtg gcacttgcac    360
cnaaccagca caantacgtc acggcagccc agctggtgtc gctgagctat caatccggtc    420
gggcgcggan acgntgtggg tccgcgcgga tgacggcacc gtctgggatc atggtcaagt    480
gctttcacng tgactgcgcc ggtggacacg ggtccggtgg tgaccccgac caactcaagc    540
acgctgtccg ttcaaggcca gacgttctcg gtgtcttcgc tcttcaccta ttctgatcct    600
cggtgagagg ntggagagt                                                  619
```

<210> SEQ ID NO 26
<211> LENGTH: 200
<212> TYPE: PRT
<213> ORGANISM: Homosapiens
<220> FEATURE:
<223> OTHER INFORMATION: Xaa= any amino acid
<223> OTHER INFORMATION: Frame shift sequence
<223> OTHER INFORMATION: Reverse strand

<400> SEQUENCE: 26

```
Xaa Xaa Xaa Xaa Tyr Xaa Gln Ser Ala Gln Ile Asn Xaa Gln Lys Glu
1               5                   10                  15

Gln Lys Val Xaa Xaa His Arg Gly Cys Arg Xaa Leu Lys Xaa Xaa Pro
                20                  25                  30

Thr Trp Thr Tyr Gln Lys Glu Ser Ala Gln Met Arg Ala Arg Cys Gly
                35                  40                  45

Gly Val Val Glu Cys Phe Pro Xaa Lys Xaa Ser Pro Xaa His Gly Thr
        50                  55                  60

Arg Asp Gly Xaa Xaa His Arg Cys Ala Pro Arg Xaa Glu Xaa Cys Xaa
65                  70                  75                  80

Xaa Val Ala Val His Xaa Gln Ser Val Arg Gln Cys Cys Asp Pro Ile
                85                  90                  95

Arg Leu Gly His Gly His Arg Cys Gly Xaa Phe Val Leu Ser Gly Val
                100                 105                 110
```

```
Ala Leu Ala Xaa Asn Gln His Xaa Tyr Val Arg Ala Ala Gln Leu Val
            115                 120                 125

Ser Leu Ser Tyr Gln Ser Gly Arg Ala Arg Xaa Xaa Cys Gly Ser Ala
        130                 135                 140

Arg Met Thr Ala Pro Ser Gly Ile Met Val Lys Cys Phe His Xaa Asp
145                 150                 155                 160

Cys Ala Gly Gly His Gly Ser Gly Gly Asp Pro Asp Gln Leu Lys His
                165                 170                 175

Ala Val Arg Ser Arg Pro Asp Val Leu Gly Val Phe Ala Leu His Leu
            180                 185                 190

Phe Ser Ser Val Arg Xaa Trp Arg
        195                 200

<210> SEQ ID NO 27
<211> LENGTH: 202
<212> TYPE: PRT
<213> ORGANISM: Homosapiens
<220> FEATURE:
<223> OTHER INFORMATION: Xaa= any amino acid
<223> OTHER INFORMATION: Frame shift sequence
<223> OTHER INFORMATION: Reverse strand

<400> SEQUENCE: 27

Phe Xaa Xaa Xaa Thr Xaa Lys Ala Arg Lys Leu Thr Xaa Asn Lys Arg
1               5                   10                  15

Asn Lys Lys Xaa Ser Xaa Thr Ala Val Ala Ala Xaa Leu Lys Xaa Xaa
            20                  25                  30

Arg Arg Gly His Ile Asn Glu Arg Asn Arg Arg Lys Cys Gly His Gly
        35                  40                  45

Val Gly Glu Trp Ser Asn Ala Phe Xaa Val Asn Xaa Pro Xaa Asp Thr
    50                  55                  60

Val Pro Val Glu Thr Val Xaa Asn Ile Val Ala Pro His Gly Xaa Xaa
65                  70                  75                  80

Tyr Ala Xaa Xaa Ser Leu Cys Xaa Tyr Ser Asp Pro Phe Asp Ser Ala
                85                  90                  95

Ala Thr Gln Tyr Asp Val Trp Asp Thr Gly Thr Gly Ala Ala Xaa Leu
            100                 105                 110

Ser Ala Gly Trp His Leu His Xaa Thr Ser Thr Xaa Thr Ser Arg Gln
        115                 120                 125

Pro Ser Trp Cys Arg Ala Ile Asn Pro Val Gly Arg Gly Xaa Xaa Val
    130                 135                 140

Gly Pro Arg Gly Arg His Arg Leu Gly Ser Trp Ser Ser Ala Phe Xaa
145                 150                 155                 160

Val Thr Ala Pro Val Asp Thr Gly Pro Val Val Thr Pro Thr Asn Ser
                165                 170                 175

Ser Thr Leu Ser Val Gln Gly Gln Thr Phe Ser Val Ser Ser Leu Phe
            180                 185                 190

Thr Tyr Ser Asp Pro Arg Glu Xaa Gly Glu
        195                 200

<210> SEQ ID NO 28
<211> LENGTH: 201
<212> TYPE: PRT
<213> ORGANISM: Homosapiens
<220> FEATURE:
<223> OTHER INFORMATION: Xaa= any amino acid
<223> OTHER INFORMATION: Frame shift sequence
<223> OTHER INFORMATION: Reverse strand
```

<400> SEQUENCE: 28

```
Xaa Lys Xaa Leu Xaa Pro Lys Arg Ala Asn Xaa Ser Ile Lys Gly Thr
 1               5                  10                  15

Lys Ser Xaa Ala Xaa Pro Arg Leu Pro Xaa Ala Xaa Xaa Thr Asp Val
             20                  25                  30

Asp Ile Ser Met Lys Gly Ile Gly Ala Asn Ala Gly Thr Val Trp Gly
             35                  40                  45

Ser Gly Arg Met Leu Ser Xaa Met Xaa Pro Xaa Thr Arg Tyr Pro Leu
         50                  55                  60

Arg Arg Cys Xaa Thr Ser Leu Arg Pro Thr Xaa Arg Xaa Met Arg Xaa
 65                  70                  75                  80

Xaa Arg Cys Ala Xaa Thr Val Ile Arg Ser Thr Val Leu Arg Pro Asn
                 85                  90                  95

Met Thr Phe Gly Thr Arg Ala Gln Val Arg Pro Xaa Cys Leu Glu Arg
                100                 105                 110

Gly Gly Thr Cys Thr Xaa Pro Ala Gln Xaa Arg His Gly Ser Pro Ala
            115                 120                 125

Gly Val Ala Glu Leu Ser Ile Arg Ser Gly Ala Xaa Thr Xaa Trp Val
        130                 135                 140

Arg Ala Asp Asp Gly Thr Val Trp Asp His Gly Gln Val Leu Ser Xaa
145                 150                 155                 160

Leu Arg Arg Trp Thr Arg Val Arg Trp Pro Arg Pro Thr Gln Ala Arg
                165                 170                 175

Cys Pro Phe Lys Ala Arg Arg Ser Arg Cys Leu Arg Ser Ser Pro Ile
                180                 185                 190

Leu Ile Leu Gly Glu Arg Xaa Glu Ser
                195                 200
```

<210> SEQ ID NO 29
<211> LENGTH: 662
<212> TYPE: DNA
<213> ORGANISM: Homosapiens
<220> FEATURE:
<221> NAME/KEY: CDS
<222> LOCATION: (1)...(660)
<223> OTHER INFORMATION: N= A,T,C or G
      Xaa= any amino acid
<223> OTHER INFORMATION: Synthetically generated nucleic acid

<400> SEQUENCE: 29

```
gat ccg acc agc aat cag gcg gag ctg cag cac ctg aaa aac gac ctt      48
Asp Pro Thr Ser Asn Gln Ala Glu Leu Gln His Leu Lys Asn Asp Leu
 1               5                  10                  15 ctc tcg gca ctg ctg ggt att tca cgc aac cgc tct gcg ctt ggc ggg      96
Leu Ser Ala Leu Leu Gly Ile Ser Arg Asn Arg Ser Ala Leu Gly Gly
             20                  25                  30 aaa cac cga cgc gct tga agg ctt acc gga cga cac gcc gcc agc ctt     144
Lys His Arg Arg Ala  *  Arg Leu Thr Gly Arg His Ala Ala Ser Leu
         35                  40                  45 gat tcg aat gca tct gga gta ctt gcg cag tca gga ttc cga gca gcg     192
Asp Ser Asn Ala Ser Gly Val Leu Ala Gln Ser Gly Phe Arg Ala Ala
         50                  55                  60 cgc caa gct gtc cga act gga tca gca acg ggt gca gaa ggt cgc gga     240
Arg Gln Ala Val Arg Thr Gly Ser Ala Thr Gly Ala Glu Gly Arg Gly
 65                  70                  75 gac cag gac gat cga cgc cag cat cgc gaa gat tga agc ttt gct gcg     288
Asp Gln Asp Asp Arg Arg Gln His Arg Glu Asp  *  Ser Phe Ala Ala
 80                  85                  90
```

-continued

```
gtg ctg cag gan cgg gtc ggg gtt cgc aag tac ctg gcg gac agg gag    336
Val Leu Gln Xaa Arg Val Gly Val Arg Lys Tyr Leu Ala Asp Arg Glu
 95             100                 105                 110 tac ggc tca aag ctg caa tat tcg cag gaa ctc cag gaa ctg gtc ggg    384
Tyr Gly Ser Lys Leu Gln Tyr Ser Gln Glu Leu Gln Glu Leu Val Gly
            115                 120                 125 atg cag cag gac atc ctg gtg caa cgg agc aaa gct cga gga aac caa    432
Met Gln Gln Asp Ile Leu Val Gln Arg Ser Lys Ala Arg Gly Asn Gln
        130                 135                 140 tgc ggn ttg tcg ccg cac ttc gac gaa aac ccg cgg naa gct tcg tct    480
Cys Gly Leu Ser Pro His Phe Asp Glu Asn Pro Arg Xaa Ala Ser Ser
    145                 150                 155 nng aat aac cgg cac ccg nct gtt ccn acg atc ttg gcc caa ggg gac    528
Xaa Asn Asn Arg His Pro Xaa Val Pro Thr Ile Leu Ala Gln Gly Asp
160                 165                 170 gca aaa aag ggc cgg caa gnc ctc aaa gga cca agg gng ttt taa aan    576
Ala Lys Lys Gly Arg Gln Xaa Leu Lys Gly Pro Arg Xaa Phe  *  Xaa
175                 180                 185 ccg agc acc cgg gac cca acc ttt aaa aan cnt tgg cgg ccc cca ttc    624
Pro Ser Thr Arg Asp Pro Thr Phe Lys Xaa Xaa Trp Arg Pro Pro Phe
190                 195                 200                 205 gac ggn gtg gng gca aca aat tgg gcc gng ccc cat tt                 662
Asp Gly Val Xaa Ala Thr Asn Trp Ala Xaa Pro His
                210                 215
```

<210> SEQ ID NO 30
<211> LENGTH: 217
<212> TYPE: PRT
<213> ORGANISM: Homosapiens
<220> FEATURE:
<223> OTHER INFORMATION: Xaa= any amino acid
<223> OTHER INFORMATION: Frame shift sequence

<400> SEQUENCE: 30

```
Asp Pro Thr Ser Asn Gln Ala Glu Leu Gln His Leu Lys Asn Asp Leu
 1               5                  10                  15

Leu Ser Ala Leu Leu Gly Ile Ser Arg Asn Arg Ser Ala Leu Gly Gly
             20                  25                  30

Lys His Arg Arg Ala Arg Leu Thr Gly Arg His Ala Ala Ser Leu Asp
         35                  40                  45

Ser Asn Ala Ser Gly Val Leu Ala Gln Ser Gly Phe Arg Ala Ala Arg
     50                  55                  60

Gln Ala Val Arg Thr Gly Ser Ala Thr Gly Ala Glu Gly Arg Gly Asp
 65                  70                  75                  80

Gln Asp Asp Arg Arg Gln His Arg Glu Asp Ser Phe Ala Ala Val Leu
                 85                  90                  95

Gln Xaa Arg Val Gly Val Arg Lys Tyr Leu Ala Asp Arg Glu Tyr Gly
            100                 105                 110

Ser Lys Leu Gln Tyr Ser Gln Glu Leu Gln Glu Leu Val Gly Met Gln
        115                 120                 125

Gln Asp Ile Leu Val Gln Arg Ser Lys Ala Arg Gly Asn Gln Cys Gly
    130                 135                 140

Leu Ser Pro His Phe Asp Glu Asn Pro Arg Xaa Ala Ser Ser Xaa Asn
145                 150                 155                 160

Asn Arg His Pro Xaa Val Pro Thr Ile Leu Ala Gln Gly Asp Ala Lys
                165                 170                 175

Lys Gly Arg Gln Xaa Leu Lys Gly Pro Arg Xaa Phe Xaa Pro Ser Thr
            180                 185                 190
```

```
                        -continued

Arg Asp Pro Thr Phe Lys Xaa Xaa Trp Arg Pro Pro Phe Asp Gly Val
        195                 200                 205
Xaa Ala Thr Asn Trp Ala Xaa Pro His
        210                 215

<210> SEQ ID NO 31
<211> LENGTH: 662
<212> TYPE: DNA
<213> ORGANISM: Homosapiens
<220> FEATURE:
<221> NAME/KEY: CDS
<222> LOCATION: (2)...(661)
<223> OTHER INFORMATION: N= A,T,C or G
      Xaa= any amino acid
<223> OTHER INFORMATION: Synthetically generated nucleic acid

<400> SEQUENCE: 31 g atc cga cca gca atc agg cgg agc tgc agc acc tga aaa acg acc ttc      49
  Ile Arg Pro Ala Ile Arg Arg Ser Cys Ser Thr  *  Lys Thr Thr Phe
   1               5                  10                      15 tct cgg cac tgc tgg gta ttt cac gca acc gct ctg cgc ttg gcg gga        97
Ser Arg His Cys Trp Val Phe His Ala Thr Ala Leu Arg Leu Ala Gly
                20                  25                  30 aac acc gac gcg ctt gaa ggc tta ccg gac gac acg ccg cca gcc ttg       145
Asn Thr Asp Ala Leu Glu Gly Leu Pro Asp Asp Thr Pro Pro Ala Leu
            35                  40                  45 att cga atg cat ctg gag tac ttg cgc agt cag gat tcc gag cag cgc       193
Ile Arg Met His Leu Glu Tyr Leu Arg Ser Gln Asp Ser Glu Gln Arg
        50                  55                  60 gcc aag ctg tcc gaa ctg gat cag caa cgg gtg cag aag gtc gcg gag       241
Ala Lys Leu Ser Glu Leu Asp Gln Gln Arg Val Gln Lys Val Ala Glu
 65                  70                  75 acc agg acg atc gac gcc agc atc gcg aag att gaa gct ttg ctg cgg       289
Thr Arg Thr Ile Asp Ala Ser Ile Ala Lys Ile Glu Ala Leu Leu Arg
 80                  85                  90                  95 tgc tgc agg anc ggg tcg ggg ttc gca agt acc tgg cgg aca ggg agt       337
Cys Cys Arg Xaa Gly Ser Gly Phe Ala Ser Thr Trp Arg Thr Gly Ser
                100                 105                 110 acg gct caa agc tgc aat att cgc agg aac tcc agg aac tgg tcg gga       385
Thr Ala Gln Ser Cys Asn Ile Arg Arg Asn Ser Arg Asn Trp Ser Gly
            115                 120                 125 tgc agc agg aca tcc tgg tgc aac gga gca aag ctc gag gaa acc aat       433
Cys Ser Arg Thr Ser Trp Cys Asn Gly Ala Lys Leu Glu Glu Thr Asn
        130                 135                 140 gcg gnt tgt cgc cgc act tcg acg aaa acc cgc ggn aag ctt cgt ctn       481
Ala Xaa Cys Arg Arg Thr Ser Thr Lys Thr Arg Gly Lys Leu Arg Leu
145                 150                 155 nga ata acc ggc acc cgn ctg ttc cna cga tct tgg ccc aag ggg acg       529
Xaa Ile Thr Gly Thr Arg Leu Phe Xaa Arg Ser Trp Pro Lys Gly Thr
160                 165                 170                 175 caa aaa agg gcc ggc aag ncc tca aag gac caa ggg ngt ttt aaa anc       577
Gln Lys Arg Ala Gly Lys Xaa Ser Lys Asp Gln Gly Xaa Phe Lys Xaa
                180                 185                 190 cga gca ccc ggg acc caa cct tta aaa anc ntt ggc ggc ccc cat tcg       625
Arg Ala Pro Gly Thr Gln Pro Leu Lys Xaa Xaa Gly Gly Pro His Ser
                195                 200                 205 acg gng tgg ngg caa caa att ggg ccg ngc ccc att t                     662
Thr Xaa Trp Xaa Gln Gln Ile Gly Pro Xaa Pro Ile
        210                 215

<210> SEQ ID NO 32
```

```
<211> LENGTH: 219
<212> TYPE: PRT
<213> ORGANISM: Homosapiens
<220> FEATURE:
<223> OTHER INFORMATION: Xaa= any amino acid
<223> OTHER INFORMATION: Frame shift sequence

<400> SEQUENCE: 32

Ile Arg Pro Ala Ile Arg Arg Ser Cys Ser Thr Lys Thr Thr Phe Ser
1               5                   10                  15

Arg His Cys Trp Val Phe His Ala Thr Ala Leu Arg Leu Ala Gly Asn
            20                  25                  30

Thr Asp Ala Leu Glu Gly Leu Pro Asp Thr Pro Ala Leu Ile
        35                  40                  45

Arg Met His Leu Glu Tyr Leu Arg Ser Gln Asp Ser Glu Gln Arg Ala
    50                  55                  60

Lys Leu Ser Glu Leu Asp Gln Gln Arg Val Gln Lys Val Ala Glu Thr
65                  70                  75                  80

Arg Thr Ile Asp Ala Ser Ile Ala Lys Ile Glu Ala Leu Leu Arg Cys
                85                  90                  95

Cys Arg Xaa Gly Ser Gly Phe Ala Ser Thr Trp Arg Thr Gly Ser Thr
            100                 105                 110

Ala Gln Ser Cys Asn Ile Arg Arg Asn Ser Arg Asn Trp Ser Gly Cys
            115                 120                 125

Ser Arg Thr Ser Trp Cys Asn Gly Ala Lys Leu Glu Glu Thr Asn Ala
130                 135                 140

Xaa Cys Arg Arg Thr Ser Thr Lys Thr Arg Gly Lys Leu Arg Leu Xaa
145                 150                 155                 160

Ile Thr Gly Thr Arg Leu Phe Xaa Arg Ser Trp Pro Lys Gly Thr Gln
                165                 170                 175

Lys Arg Ala Gly Lys Xaa Ser Lys Asp Gln Gly Xaa Phe Lys Xaa Arg
            180                 185                 190

Ala Pro Gly Thr Gln Pro Leu Lys Xaa Xaa Gly Gly Pro His Ser Thr
            195                 200                 205

Xaa Trp Xaa Gln Gln Ile Gly Pro Xaa Pro Ile
210                 215

<210> SEQ ID NO 33
<211> LENGTH: 662
<212> TYPE: DNA
<213> ORGANISM: Homosapiens
<220> FEATURE:
<221> NAME/KEY: CDS
<222> LOCATION: (3)...(662)
<223> OTHER INFORMATION: N= A,T,C or G
      Xaa= any amino acid
<223> OTHER INFORMATION: Synthetically generated nucleic acid

<400> SEQUENCE: 33 ga tcc gac cag caa tca ggc gga gct gca gca cct gaa aaa cga cct          47
   Ser Asp Gln Gln Ser Gly Gly Ala Ala Ala Pro Glu Lys Arg Pro
   1               5                   10                  15 tct ctc ggc act gct ggg tat ttc acg caa ccg ctc tgc gct tgg cgg         95
Ser Leu Gly Thr Ala Gly Tyr Phe Thr Gln Pro Leu Cys Ala Trp Arg
            20                  25                  30 gaa aca ccg acg cgc ttg aag gct tac cgg acg aca cgc cgc cag cct        143
Glu Thr Pro Thr Arg Leu Lys Ala Tyr Arg Thr Thr Arg Arg Gln Pro
            35                  40                  45 tga ttc gaa tgc atc tgg agt act tgc gca gtc agg att ccg agc agc        191
 *  Phe Glu Cys Ile Trp Ser Thr Cys Ala Val Arg Ile Pro Ser Ser
```

```
                  50                      55                      60
gcg cca agc tgt ccg aac tgg atc agc aac ggg tgc aga agg tcg cgg    239
Ala Pro Ser Cys Pro Asn Trp Ile Ser Asn Gly Cys Arg Arg Ser Arg
             65                      70                      75 aga cca gga cga tcg acg cca gca tcg cga aga ttg aag ctt tgc tgc    287
Arg Pro Gly Arg Ser Thr Pro Ala Ser Arg Arg Leu Lys Leu Cys Cys
         80                      85                      90 ggt gct gca gga ncg ggt cgg ggt tcg caa gta cct ggc gga cag gga    335
Gly Ala Ala Gly Xaa Gly Arg Gly Ser Gln Val Pro Gly Gly Gln Gly
 95                     100                     105                     110 gta cgg ctc aaa gct gca ata ttc gca gga act cca gga act ggt cgg    383
Val Arg Leu Lys Ala Ala Ile Phe Ala Gly Thr Pro Gly Thr Gly Arg
                    115                     120                     125 gat gca gca gga cat cct ggt gca acg gag caa agc tcg agg aaa cca    431
Asp Ala Ala Gly His Pro Gly Ala Thr Glu Gln Ser Ser Arg Lys Pro
                130                     135                     140 atg cgg ntt gtc gcc gca ctt cga cga aaa ccc gcg gna agc ttc gtc    479
Met Arg Xaa Val Ala Ala Leu Arg Arg Lys Pro Ala Xaa Ser Phe Val
            145                     150                     155 tnn gaa taa ccg gca ccc gnc tgt tcc nac gat ctt ggc cca agg gga    527
Xaa Glu  *  Pro Ala Pro Xaa Cys Ser Xaa Asp Leu Gly Pro Arg Gly
160                     165                     170 cgc aaa aaa ggg ccg gca agn cct caa agg acc aag ggn gtt tta aaa    575
Arg Lys Lys Gly Pro Ala Xaa Pro Gln Arg Thr Lys Gly Val Leu Lys
    175                     180                     185 ncc gag cac ccg gga ccc aac ctt taa aaa ncn ttg gcg gcc ccc att    623
Xaa Glu His Pro Gly Pro Asn Leu  *  Lys Xaa Leu Ala Ala Pro Ile
190                     195                     200 cga cgg ngt ggn ggc aac aaa ttg ggc cgn gcc cca ttt                662
Arg Arg Xaa Gly Gly Asn Lys Leu Gly Arg Ala Pro Phe
205                     210                     215

<210> SEQ ID NO 34
<211> LENGTH: 217
<212> TYPE: PRT
<213> ORGANISM: Homosapiens
<220> FEATURE:
<223> OTHER INFORMATION: Xaa= any amino acid
<223> OTHER INFORMATION: Frame shift sequence

<400> SEQUENCE: 34

Ser Asp Gln Gln Ser Gly Gly Ala Ala Pro Glu Lys Arg Pro Ser
1                5                  10                  15

Leu Gly Thr Ala Gly Tyr Phe Thr Gln Pro Leu Cys Ala Trp Arg Glu
                20                  25                  30

Thr Pro Thr Arg Leu Lys Ala Tyr Arg Thr Thr Arg Arg Gln Pro Phe
            35                  40                  45

Glu Cys Ile Trp Ser Thr Cys Ala Val Arg Ile Pro Ser Ser Ala Pro
        50                  55                  60

Ser Cys Pro Asn Trp Ile Ser Asn Gly Cys Arg Arg Ser Arg Pro
65                  70                  75                  80

Gly Arg Ser Thr Pro Ala Ser Arg Arg Leu Lys Leu Cys Cys Gly Ala
                85                  90                  95

Ala Gly Xaa Gly Arg Gly Ser Gln Val Pro Gly Gly Gln Gly Val Arg
            100                 105                 110

Leu Lys Ala Ala Ile Phe Ala Gly Thr Pro Gly Thr Gly Arg Asp Ala
        115                 120                 125

Ala Gly His Pro Gly Ala Thr Glu Gln Ser Ser Arg Lys Pro Met Arg
    130                 135                 140
```

Xaa Val Ala Ala Leu Arg Arg Lys Pro Ala Xaa Ser Phe Val Xaa Glu
145                 150                 155                 160

Pro Ala Pro Xaa Cys Ser Xaa Asp Leu Gly Pro Arg Gly Arg Lys Lys
            165                 170                 175

Gly Pro Ala Xaa Pro Gln Arg Thr Lys Gly Val Leu Lys Xaa Glu His
            180                 185                 190

Pro Gly Pro Asn Leu Lys Xaa Leu Ala Ala Pro Ile Arg Arg Xaa Gly
            195                 200                 205

Gly Asn Lys Leu Gly Arg Ala Pro Phe
        210                 215

<210> SEQ ID NO 35
<211> LENGTH: 661
<212> TYPE: DNA
<213> ORGANISM: Homosapiens
<220> FEATURE:
<223> OTHER INFORMATION: N= A, T, C or G
<223> OTHER INFORMATION: Frame shift sequence
<223> OTHER INFORMATION: Reverse strand

<400> SEQUENCE: 35
aaatggggcn cggcccaatt tgttgccncc acnccgtcga atgggggccg ccaangnttt     60
ttaaaggttg ggtcccgggt gctcggnttt taaaacnccc ttggtccttt gaggncttgc    120
cggccctttt ttgcgtcccc ttgggccaag atcgtnggaa cagncgggtg ccggttattc    180
nnagacgaag cttnccgcgg gttttcgtcg aagtgcggcg acaanccgca ttggtttcct    240
cgagctttgc tccgttgcac caggatgtcc tgctgcatcc cgaccagttc ctggagttcc    300
tgcgaatatt gcagctttga gccgtactcc ctgtccgcca ggtacttgcg aacccgaccc    360
gntcctgcag caccgcagca aagcttcaat cttcgcgatg ctggcgtcga tcgtcctggt    420
ctccgcgacc ttctgcaccc gttgctgatc cagttcggac agcttggcgc gctgctcgga    480
atcctgactg cgcaagtact ccagatgcat tcgaatcaag gctggcggcg tgtcgtccgg    540
taagccttca agcgcgtcgg tgtttcccgc caagcgcaga gcggttgcgt gaaatacccca    600 gcagtgccga gagaaggtcg tttttcaggt gctgcagctc cgcctgattg ctggtcggat    660
c                                                                    661

<210> SEQ ID NO 36
<211> LENGTH: 218
<212> TYPE: PRT
<213> ORGANISM: Homosapiens
<220> FEATURE:
<223> OTHER INFORMATION: Xaa= any amino acid
<223> OTHER INFORMATION: Frame shift sequence
<223> OTHER INFORMATION: Reverse strand

<400> SEQUENCE: 36

Lys Trp Gly Xaa Ala Gln Phe Val Ala Xaa Xaa Pro Ser Asn Gly Gly
1               5                   10                  15

Arg Gln Xaa Phe Leu Lys Val Gly Ser Arg Val Leu Xaa Phe Asn Xaa
            20                  25                  30

Leu Gly Pro Leu Arg Xaa Cys Arg Pro Phe Phe Ala Ser Pro Trp Ala
            35                  40                  45

Lys Ile Xaa Gly Thr Xaa Gly Cys Arg Leu Phe Xaa Asp Glu Ala Xaa
        50                  55                  60

Arg Gly Phe Ser Ser Lys Cys Gly Asp Xaa Pro His Trp Phe Pro Arg
65                  70                  75                  80

```
Ala Leu Leu Arg Cys Thr Arg Met Ser Cys Cys Ile Pro Thr Ser Ser
                85                  90                  95

Trp Ser Ser Cys Glu Tyr Cys Ser Phe Glu Pro Tyr Ser Leu Ser Ala
            100                 105                 110

Arg Tyr Leu Arg Thr Pro Thr Xaa Ser Cys Ser Thr Ala Ala Lys Leu
        115                 120                 125

Gln Ser Ser Arg Cys Trp Arg Ser Ser Trp Ser Pro Arg Pro Ser
    130                 135                 140

Ala Pro Val Ala Asp Pro Val Arg Thr Ala Trp Arg Ala Ala Arg Asn
145                 150                 155                 160

Pro Asp Cys Ala Ser Thr Pro Asp Ala Phe Glu Ser Arg Leu Ala Ala
                165                 170                 175

Cys Arg Pro Val Ser Leu Gln Ala Arg Arg Cys Phe Pro Pro Ser Ala
            180                 185                 190

Glu Arg Leu Arg Glu Ile Pro Ser Ser Ala Glu Arg Ser Phe Phe
        195                 200                 205

Arg Cys Cys Ser Ser Ala Leu Leu Val Gly
    210                 215

<210> SEQ ID NO 37
<211> LENGTH: 217
<212> TYPE: PRT
<213> ORGANISM: Homosapiens
<220> FEATURE:
<223> OTHER INFORMATION: Xaa= any amino acid
<223> OTHER INFORMATION: Frame shift sequence
<223> OTHER INFORMATION: Reverse strand

<400> SEQUENCE: 37

Asn Gly Xaa Arg Pro Asn Leu Leu Xaa Pro Xaa Arg Arg Met Gly Ala
1               5                   10                  15

Ala Xaa Xaa Phe Arg Leu Gly Pro Gly Cys Ser Xaa Phe Lys Xaa Pro
            20                  25                  30

Leu Val Leu Xaa Leu Ala Gly Pro Phe Leu Arg Pro Leu Gly Pro Arg
        35                  40                  45

Ser Xaa Glu Gln Xaa Gly Ala Gly Tyr Xaa Xaa Thr Lys Leu Xaa Ala
50                  55                  60

Gly Phe Arg Arg Ser Ala Ala Thr Xaa Arg Ile Gly Phe Leu Glu Leu
65                  70                  75                  80

Cys Ser Val Ala Pro Gly Cys Pro Ala Ala Ser Arg Pro Val Pro Gly
                85                  90                  95

Val Pro Ala Asn Ile Ala Ala Leu Ser Arg Thr Pro Cys Pro Pro Gly
            100                 105                 110

Thr Cys Glu Pro Arg Pro Xaa Pro Ala Ala Pro Gln Ser Phe Asn
        115                 120                 125

Leu Arg Asp Ala Gly Val Asp Arg Pro Gly Leu Arg Asp Leu Leu His
    130                 135                 140

Pro Leu Leu Ile Gln Phe Gly Gln Leu Gly Ala Leu Leu Gly Ile Leu
145                 150                 155                 160

Thr Ala Gln Val Leu Gln Met His Ser Asn Gln Gly Trp Arg Val
                165                 170                 175

Val Arg Ala Phe Lys Arg Val Gly Val Ser Arg Gln Ala Gln Ser Gly
            180                 185                 190

Cys Val Lys Tyr Pro Ala Asx Pro Arg Trp Gly Arg Phe Ser Gly Ala
        195                 200                 205

Ala Ala Pro Pro Asp Cys Trp Ser Asp
```

-continued

```
              210                 215

<210> SEQ ID NO 38
<211> LENGTH: 217
<212> TYPE: PRT
<213> ORGANISM: Homosapiens
<220> FEATURE:
<223> OTHER INFORMATION: Xaa= any amino acid
<223> OTHER INFORMATION: Frame shift sequence
<223> OTHER INFORMATION: Reverse strand

<400> SEQUENCE: 38

Met Gly Xaa Gly Pro Ile Cys Cys Xaa His Xaa Val Glu Trp Gly Pro
 1               5                  10                  15

Pro Xaa Xaa Phe Lys Gly Trp Val Pro Gly Ala Arg Xaa Leu Lys Xaa
             20                  25                  30

Pro Trp Ser Phe Glu Xaa Leu Pro Ala Leu Phe Cys Val Pro Leu Gly
         35                  40                  45

Gln Asp Arg Xaa Asn Xaa Arg Val Pro Val Val Ile Xaa Arg Arg Ser
     50                  55                  60

Xaa Pro Arg Val Phe Val Glu Val Arg Arg Gln Xaa Ala Leu Val Ser
 65                  70                  75                  80

Ser Ser Phe Ala Pro Leu His Gln Asp Val Leu Leu His Pro Asp Gln
                 85                  90                  95

Phe Leu Glu Phe Leu Arg Ile Leu Gln Leu Ala Val Leu Pro Val Arg
            100                 105                 110

Gln Val Leu Ala Asn Pro Asp Pro Xaa Leu Gln His Arg Ser Lys Ala
        115                 120                 125

Ser Ile Phe Ala Met Leu Ala Ser Ile Val Leu Val Ser Ala Thr Phe
    130                 135                 140

Cys Thr Arg Cys Ser Ser Ser Asp Ser Leu Ala Arg Cys Ser Glu Ser
145                 150                 155                 160

Leu Arg Lys Tyr Ser Arg Cys Ile Arg Ile Lys Ala Gly Gly Val Ser
                165                 170                 175

Ser Gly Lys Pro Ser Ser Ala Ser Val Phe Pro Ala Lys Arg Arg Ala
            180                 185                 190

Val Ala Asn Thr Gln Gln Cys Arg Glu Lys Val Val Phe Gln Val Leu
        195                 200                 205

Gln Leu Arg Leu Ile Ala Gly Arg Ile
    210                 215

<210> SEQ ID NO 39
<211> LENGTH: 191
<212> TYPE: DNA
<213> ORGANISM: Homosapiens
<220> FEATURE:
<221> NAME/KEY: CDS
<222> LOCATION: (1)...(189)
<223> OTHER INFORMATION: N= A,T,C or G
      Xaa= any amino acid
<223> OTHER INFORMATION: Synthetically generated nucleic acid

<400> SEQUENCE: 39 cgc gct gga cta tcn cta aag ggt ctc cna cna cgt cca ncc gga cna      48
Arg Ala Gly Leu Ser Leu Lys Gly Leu Xaa Xaa Arg Pro Xaa Gly Xaa
  1               5                  10                  15 gct gac ctc gtt tcc ncn aag cgt gaa act gaa ggc cgg tga aac cnt      96
Ala Asp Leu Val Ser Xaa Lys Arg Glu Thr Glu Gly Arg  *  Asn Xaa
             20                  25                  30 cnt gtt cgc ctn gat cac cta cta gtc gcg cgc cnn gcg cga cag gat     144
```

```
Xaa Val Arg Leu Asp His Leu Leu Val Ala Arg Xaa Ala Arg Gln Asp
            35                  40                  45 caa cgc caa ggt gat ggc cga tcc ccg cct ggc gtc gtc gat gga         189
Gln Arg Gln Gly Asp Gly Arg Ser Pro Pro Gly Val Val Asp Gly
        50                  55                  60 tc                                                                  191
```

<210> SEQ ID NO 40
<211> LENGTH: 62
<212> TYPE: PRT
<213> ORGANISM: Homosapiens
<220> FEATURE:
<223> OTHER INFORMATION: Xaa= any amino acid
<223> OTHER INFORMATION: Frame shift sequence

<400> SEQUENCE: 40

```
Arg Ala Gly Leu Ser Leu Lys Gly Leu Xaa Xaa Arg Pro Xaa Gly Xaa
1               5                   10                  15

Ala Asp Leu Val Ser Xaa Lys Arg Glu Thr Glu Gly Arg Asn Xaa Xaa
            20                  25                  30

Val Arg Leu Asp His Leu Leu Val Ala Arg Xaa Ala Arg Gln Asp Gln
            35                  40                  45

Arg Gln Gly Asp Gly Arg Ser Pro Pro Gly Val Val Asp Gly
        50                  55                  60
```

<210> SEQ ID NO 41
<211> LENGTH: 191
<212> TYPE: DNA
<213> ORGANISM: Homosapiens
<220> FEATURE:
<221> NAME/KEY: CDS
<222> LOCATION: (2)...(191)
<223> OTHER INFORMATION: N= A,T,C or G
     Xaa= any amino acid
<223> OTHER INFORMATION: Synthetically generated nucleic acid

<400> SEQUENCE: 41

```
c gcg ctg gac tat cnc taa agg gtc tcc nac nac gtc can ccg gac nag   49
  Ala Leu Asp Tyr Xaa  *  Arg Val Ser Xaa Xaa Val Xaa Pro Asp Xaa
   1               5                   10                  15 ctg acc tcg ttt ccn cna agc gtg aaa ctg aag gcc ggt gaa acc ntc     97
Leu Thr Ser Phe Pro Xaa Ser Val Lys Leu Lys Ala Gly Glu Thr Xaa
                20                  25                  30 ntg ttc gcc tng atc acc tac tag tcg cgc gcc nng cgc gac agg atc    145
Xaa Phe Ala Xaa Ile Thr Tyr  *  Ser Arg Ala Xaa Arg Asp Arg Ile
            35                  40                  45 aac gcc aag gtg atg gcc gat ccc cgc ctg gcg tcg tcg atg gat c      191
Asn Ala Lys Val Met Ala Asp Pro Arg Leu Ala Ser Ser Met Asp
        50                  55                  60
```

<210> SEQ ID NO 42
<211> LENGTH: 61
<212> TYPE: PRT
<213> ORGANISM: Homosapiens
<220> FEATURE:
<223> OTHER INFORMATION: Xaa= any amino acid
<223> OTHER INFORMATION: Frame shift sequence

<400> SEQUENCE: 42

```
Ala Leu Asp Tyr Xaa Arg Val Ser Xaa Xaa Val Xaa Pro Asp Xaa Leu
1               5                   10                  15

Thr Ser Phe Pro Xaa Ser Val Lys Leu Lys Ala Gly Glu Thr Xaa Xaa
            20                  25                  30
```

```
Phe Ala Xaa Ile Thr Tyr Ser Arg Ala Xaa Arg Asp Arg Ile Asn Ala
        35                  40                  45

Lys Val Met Ala Asp Pro Arg Leu Ala Ser Ser Met Asp
 50                  55                  60

<210> SEQ ID NO 43
<211> LENGTH: 191
<212> TYPE: DNA
<213> ORGANISM: Homosapiens
<220> FEATURE:
<221> NAME/KEY: CDS
<222> LOCATION: (3)...(191)
<223> OTHER INFORMATION: N= A,T,C or G
      Xaa= any amino acid
<223> OTHER INFORMATION: Synthetically generated nucleic acid

<400> SEQUENCE: 43 cg cgc tgg act atc nct aaa ggg tct ccn acn acg tcc anc cgg acn        47
   Arg Trp Thr Ile Xaa Lys Gly Ser Pro Thr Thr Ser Xaa Arg Thr
    1               5                  10                  15 agc tga cct cgt ttc cnc naa gcg tga aac tga agg ccg gtg aaa ccn       95
Ser  *  Pro Arg Phe Xaa Xaa Ala  *  Asn  *  Arg Pro Val Lys Pro
                     20                  25 tcn tgt tcg cct nga tca cct act agt cgc gcg ccn ngc gcg aca gga      143
Ser Cys Ser Pro Xaa Ser Pro Thr Ser Arg Ala Pro Xaa Ala Thr Gly
         30                  35                  40 tca acg cca agg tga tgg ccg atc ccc gcc tgg cgt cgt cga tgg atc      191
Ser Thr Pro Arg  *  Trp Pro Ile Pro Ala Trp Arg Arg Trp Ile
 45                  50                  55

<210> SEQ ID NO 44
<211> LENGTH: 59
<212> TYPE: PRT
<213> ORGANISM: Homosapiens
<220> FEATURE:
<223> OTHER INFORMATION: Xaa= any amino acid
<223> OTHER INFORMATION: Frame shift sequence

<400> SEQUENCE: 44

Arg Trp Thr Ile Xaa Lys Gly Ser Pro Thr Thr Ser Xaa Arg Thr Ser
 1               5                  10                  15

Pro Arg Phe Xaa Xaa Ala Asn Arg Pro Val Lys Pro Ser Cys Ser Pro
             20                  25                  30

Xaa Ser Pro Thr Ser Arg Ala Pro Xaa Ala Thr Gly Ser Thr Pro Arg
         35                  40                  45

Trp Pro Ile Pro Ala Trp Arg Arg Trp Ile
     50                  55

<210> SEQ ID NO 45
<211> LENGTH: 190
<212> TYPE: DNA
<213> ORGANISM: Homosapiens
<220> FEATURE:
<223> OTHER INFORMATION: N= A,T,C or G
<223> OTHER INFORMATION: Synthetically generated nucleic acid
<223> OTHER INFORMATION: Reverse strand

<400> SEQUENCE: 45
gatccatcga cgacgccagg cgggatcggc catcaccttg gcgttgatcc tgtcgcgcnn     60
ggcgcgcgac tagtaggtga tcnaggcgaa cangangggtt tcaccggcct tcagtttcac   120
gcttngngga aacgaggtca gctngtccgg ntgacgtng tnggagaccc tttagngata    180
gtccagcgcg                                                            190
```

-continued

<210> SEQ ID NO 46
<211> LENGTH: 61
<212> TYPE: PRT
<213> ORGANISM: Homosapiens
<220> FEATURE:
<223> OTHER INFORMATION: Xaa= any amino acid
<223> OTHER INFORMATION: Frame shift sequence
<223> OTHER INFORMATION: Reverse strand

<400> SEQUENCE: 46

Asp Pro Ser Thr Thr Pro Gly Gly Asp Arg Pro Ser Pro Trp Arg Ser
1               5                   10                  15

Cys Arg Xaa Xaa Arg Ala Thr Ser Arg Xaa Arg Arg Thr Xaa Xaa Phe
            20                  25                  30

His Arg Pro Ser Val Ser Arg Xaa Xaa Glu Thr Arg Ser Ala Xaa Pro
        35                  40                  45

Xaa Gly Arg Xaa Xaa Arg Pro Phe Xaa Asp Ser Pro Ala
    50                  55                  60

<210> SEQ ID NO 47
<211> LENGTH: 63
<212> TYPE: PRT
<213> ORGANISM: Homosapiens
<220> FEATURE:
<223> OTHER INFORMATION: Xaa= any amino acid
<223> OTHER INFORMATION: Frame shift sequence
<223> OTHER INFORMATION: Reverse strand

<400> SEQUENCE: 47

Ile His Arg Arg Arg Gln Ala Gly Ile Gly His His Leu Gly Val Asp
1               5                   10                  15

Pro Val Ala Xaa Gly Ala Arg Leu Val Gly Asp Xaa Gly Glu Xaa Xaa
            20                  25                  30

Gly Phe Thr Gly Leu Gln Phe His Ala Xaa Xaa Lys Arg Gly Gln Xaa
        35                  40                  45

Val Arg Xaa Asp Xaa Xaa Gly Asp Pro Leu Xaa Ile Val Gln Arg
    50                  55                  60

<210> SEQ ID NO 48
<211> LENGTH: 59
<212> TYPE: PRT
<213> ORGANISM: Homosapiens
<220> FEATURE:
<223> OTHER INFORMATION: Xaa= any amino acid
<223> OTHER INFORMATION: Frame shift sequence
<223> OTHER INFORMATION: Reverse strand

<400> SEQUENCE: 48

Ser Ile Asp Asp Ala Arg Arg Gly Ser Ala Ile Thr Leu Ala Leu Ile
1               5                   10                  15

Leu Ser Arg Xaa Ala Arg Asp Val Ile Xaa Ala Asn Xaa Xaa Val Ser
            20                  25                  30

Pro Ala Phe Ser Phe Thr Leu Xaa Gly Asn Glu Val Ser Xaa Ser Xaa
        35                  40                  45

Trp Thr Xaa Xaa Glu Thr Leu Xaa Ser Ser Ala
    50                  55

<210> SEQ ID NO 49
<211> LENGTH: 552
<212> TYPE: DNA
<213> ORGANISM: Homosapiens
<220> FEATURE:
<221> NAME/KEY: CDS
<222> LOCATION: (1)...(552)
<223> OTHER INFORMATION: N= A,T,C or G
       Xaa= any amino acid
<223> OTHER INFORMATION: Synthetically generated nucleic acid

<400> SEQUENCE: 49

```
gat ccg ctc gat gcc cag gcc cag tac agc gaa ctg ttc gcc cat ggc      48
Asp Pro Leu Asp Ala Gln Ala Gln Tyr Ser Glu Leu Phe Ala His Gly
 1               5                  10                  15 cgc gcc acg tca ctg ttg cta ttc gaa cat gtt cac ggt gaa tcc cgt      96
Arg Ala Thr Ser Leu Leu Leu Phe Glu His Val His Gly Glu Ser Arg
             20                  25                  30 gac cgc ggc cag gcg atg gtg gac ctg ctg gcg cag tac gag cag cac     144
Asp Arg Gly Gln Ala Met Val Asp Leu Leu Ala Gln Tyr Glu Gln His
         35                  40                  45 ggt ttg cag tta aac agc cgc gaa tta ccg gac cac ctg ccg ctg tat     192
Gly Leu Gln Leu Asn Ser Arg Glu Leu Pro Asp His Leu Pro Leu Tyr
     50                  55                  60 ctg gag tac ctg tcg cag ctg ccg caa ggc gaa gcc gtg gaa ggt ttg     240
Leu Glu Tyr Leu Ser Gln Leu Pro Gln Gly Glu Ala Val Glu Gly Leu
 65                  70                  75                  80 aaa gat atc gcg ccg att ctg gca ttg ctg agc gcg cgt ctg caa cag     288
Lys Asp Ile Ala Pro Ile Leu Ala Leu Leu Ser Ala Arg Leu Gln Gln
                 85                  90                  95 cgt gaa agc cgt tat gcc gtg atg ttt gat ctg ctg ctg aaa ttg gcc     336
Arg Glu Ser Arg Tyr Ala Val Met Phe Asp Leu Leu Leu Lys Leu Ala
            100                 105                 110 gat acc gct atc gac agc gac aaa gtg gcg gaa aaa att gcc gac gaa     384
Asp Thr Ala Ile Asp Ser Asp Lys Val Ala Glu Lys Ile Ala Asp Glu
        115                 120                 125 gcg cgc gat gat acg ccg cag gcg ctg gat gct gtt tgg gaa gaa gag     432
Ala Arg Asp Asp Thr Pro Gln Ala Leu Asp Ala Val Trp Glu Glu Glu
    130                 135                 140 cag gtt aaa ttc ttt gct gac aaa ggc tgc ggc gat tca gca atc act     480
Gln Val Lys Phe Phe Ala Asp Lys Gly Cys Gly Asp Ser Ala Ile Thr
145                 150                 155                 160 gct cat cag cgt cgc ttt gcc ggt gcc gtc gcg ccg caa tat ctg aat     528
Ala His Gln Arg Arg Phe Ala Gly Ala Val Ala Pro Gln Tyr Leu Asn
                165                 170                 175 atc ctc ggt gag agg ctg gag agt                                     552
Ile Leu Gly Glu Arg Leu Glu Ser
            180
```

<210> SEQ ID NO 50
<211> LENGTH: 184
<212> TYPE: PRT
<213> ORGANISM: Homosapiens
<220> FEATURE:
<223> OTHER INFORMATION: Frame shift sequence
<223> OTHER INFORMATION: Frame shift sequence

<400> SEQUENCE: 50

```
Asp Pro Leu Asp Ala Gln Ala Gln Tyr Ser Glu Leu Phe Ala His Gly
 1               5                  10                  15

Arg Ala Thr Ser Leu Leu Leu Phe Glu His Val His Gly Glu Ser Arg
             20                  25                  30

Asp Arg Gly Gln Ala Met Val Asp Leu Leu Ala Gln Tyr Glu Gln His
         35                  40                  45

Gly Leu Gln Leu Asn Ser Arg Glu Leu Pro Asp His Leu Pro Leu Tyr
     50                  55                  60

Leu Glu Tyr Leu Ser Gln Leu Pro Gln Gly Glu Ala Val Glu Gly Leu
```

```
                65                    70                    75                    80
Lys Asp Ile Ala Pro Ile Leu Ala Leu Leu Ser Ala Arg Leu Gln Gln
                    85                    90                    95

Arg Glu Ser Arg Tyr Ala Val Met Phe Asp Leu Leu Lys Leu Ala
                100                   105                   110

Asp Thr Ala Ile Asp Ser Asp Lys Val Ala Glu Lys Ile Ala Asp Glu
            115                   120                   125

Ala Arg Asp Asp Thr Pro Gln Ala Leu Asp Ala Val Trp Glu Glu Glu
    130                   135                   140

Gln Val Lys Phe Phe Ala Asp Lys Gly Cys Gly Asp Ser Ala Ile Thr
145                   150                   155                   160

Ala His Gln Arg Arg Phe Ala Gly Ala Val Ala Pro Gln Tyr Leu Asn
                165                   170                   175

Ile Leu Gly Glu Arg Leu Glu Ser
            180

<210> SEQ ID NO 51
<211> LENGTH: 552
<212> TYPE: DNA
<213> ORGANISM: Homosapiens
<220> FEATURE:
<221> NAME/KEY: CDS
<222> LOCATION: (2)...(552)
<223> OTHER INFORMATION: N= A,T, C or G
      Xaa= any amino acid
<223> OTHER INFORMATION: Synthetically generated nucleic acid

<400> SEQUENCE: 51 g atc cgc tcg atg ccc agg ccc agt aca gcg aac tgt tcg ccc atg gcc      49
  Ile Arg Ser Met Pro Arg Pro Ser Thr Ala Asn Cys Ser Pro Met Ala
  1               5                   10                  15 gcg cca cgt cac tgt tgc tat tcg aac atg ttc acg gtg aat ccc gtg       97
Ala Pro Arg His Cys Cys Tyr Ser Asn Met Phe Thr Val Asn Pro Val
                20                  25                  30 acc gcg gcc agg cga tgg tgg acc tgc tgg cgc agt acg agc agc acg      145
Thr Ala Ala Arg Arg Trp Trp Thr Cys Trp Arg Ser Thr Ser Ser Thr
        35                  40                  45 gtt tgc agt taa aca gcc gcg aat tac cgg acc acc tgc cgc tgt atc      193
Val Cys Ser  *  Thr Ala Ala Asn Tyr Arg Thr Thr Cys Arg Cys Ile
50                  55                  60 tgg agt acc tgt cgc agc tgc cgc aag gcg aag ccg tgg aag gtt tga      241
Trp Ser Thr Cys Arg Ser Cys Arg Lys Ala Lys Pro Trp Lys Val  *
65                  70                  75 aag ata tcg cgc cga ttc tgg cat tgc tga gcg cgc gtc tgc aac agc      289
Lys Ile Ser Arg Arg Phe Trp His Cys  *  Ala Arg Val Cys Asn Ser
80                  85                  90 gtg aaa gcc gtt atg ccg tga tgt ttg atc tgc tgc tga aat tgg ccg      337
Val Lys Ala Val Met Pro  *  Cys Leu Ile Cys Cys  *  Asn Trp Pro
95                  100                 105 ata ccg cta tcg aca gcg aca aag tgg cgg aaa aaa ttg ccg acg aag      385
Ile Pro Leu Ser Thr Ala Thr Lys Trp Arg Lys Lys Leu Pro Thr Lys
        110                 115                 120 cgc gcg atg ata cgc cgc agg cgc tgg atg ctg ttt ggg aag aag agc      433
Arg Ala Met Ile Arg Arg Arg Trp Met Leu Phe Gly Lys Lys Ser
125                 130                 135 agg tta aat tct ttg ctg aca aag gct gcg gcg att cag caa tca ctg      481
Arg Leu Asn Ser Leu Leu Thr Lys Ala Ala Ala Ile Gln Gln Ser Leu
140                 145                 150                 155 ctc atc agc gtc gct ttg ccg gtg ccg tcg cgc cgc aat atc tga ata      529
Leu Ile Ser Val Ala Leu Pro Val Pro Ser Arg Arg Asn Ile  *  Ile
```

-continued

```
                 160                 165                 170
tcc tcg gtg aga ggc tgg aga gt                                              552
Ser Ser Val Arg Gly Trp Arg
                175
```

<210> SEQ ID NO 52
<211> LENGTH: 177
<212> TYPE: PRT
<213> ORGANISM: Homosapiens
<220> FEATURE:
<223> OTHER INFORMATION: Frame shift sequence

<400> SEQUENCE: 52

```
Ile Arg Ser Met Pro Arg Pro Ser Thr Ala Asn Cys Ser Pro Met Ala
 1               5                  10                  15

Ala Pro Arg His Cys Cys Tyr Ser Asn Met Phe Thr Val Asn Pro Val
                20                  25                  30

Thr Ala Ala Arg Arg Trp Trp Thr Cys Trp Arg Ser Thr Ser Ser Thr
            35                  40                  45

Val Cys Ser Thr Ala Ala Asn Tyr Arg Thr Thr Cys Arg Cys Ile Trp
 50                  55                  60

Ser Thr Cys Arg Ser Cys Arg Lys Ala Lys Pro Trp Lys Val Lys Ile
65                  70                  75                  80

Ser Arg Arg Phe Trp His Cys Ala Arg Val Cys Asn Ser Val Lys Ala
                85                  90                  95

Val Met Pro Cys Leu Ile Cys Cys Asn Trp Pro Ile Pro Leu Ser Thr
            100                 105                 110

Ala Thr Lys Trp Arg Lys Lys Leu Pro Thr Lys Arg Ala Met Ile Arg
        115                 120                 125

Arg Arg Arg Trp Met Leu Phe Gly Lys Lys Ser Arg Leu Asn Ser Leu
130                 135                 140

Leu Thr Lys Ala Ala Ala Ile Gln Gln Ser Leu Leu Ile Ser Val Ala
145                 150                 155                 160

Leu Pro Val Pro Ser Arg Arg Asn Ile Ile Ser Ser Val Arg Gly Trp
                165                 170                 175

Arg
```

<210> SEQ ID NO 53
<211> LENGTH: 552
<212> TYPE: DNA
<213> ORGANISM: Homosapiens
<220> FEATURE:
<221> NAME/KEY: CDS
<222> LOCATION: (3)...(552)
<223> OTHER INFORMATION: Synthetically generated nucleic acid

<400> SEQUENCE: 53

```
ga tcc gct cga tgc cca ggc cca gta cag cga act gtt cgc cca tgg        47
   Ser Ala Arg Cys Pro Gly Pro Val Gln Arg Thr Val Arg Pro Trp
     1               5                  10                  15 ccg cgc cac gtc act gtt gct att cga aca tgt tca cgg tga atc ccg        95
Pro Arg His Val Thr Val Ala Ile Arg Thr Cys Ser Arg  *  Ile Pro
                20                  25                  30 tga ccg cgg cca ggc gat ggt gga cct gct ggc gca gta cga gca gca       143
 *  Pro Arg Pro Gly Asp Gly Gly Pro Ala Gly Ala Val Arg Ala Ala
                35                  40                  45 cgg ttt gca gtt aaa cag ccg cga att acc gga cca cct gcc gct gta       191
Arg Phe Ala Val Lys Gln Pro Arg Ile Thr Gly Pro Pro Ala Ala Val
                50                  55                  60
```

-continued

```
tct gga gta cct gtc gca gct gcc gca agg cga agc cgt gga agg ttt           239
Ser Gly Val Pro Val Ala Ala Ala Ala Arg Arg Ser Arg Gly Arg Phe
            65                  70                  75 gaa aga tat cgc gcc gat tct ggc att gct gag cgc gcg tct gca aca           287
Glu Arg Tyr Arg Ala Asp Ser Gly Ile Ala Glu Arg Ala Ser Ala Thr
            80                  85                  90 gcg tga aag ccg tta tgc cgt gat gtt tga tct gct gct gaa att ggc           335
Ala  *  Lys Pro Leu Cys Arg Asp Val  *  Ser Ala Ala Glu Ile Gly
            95                  100                 105 cga tac cgc tat cga cag cga caa agt ggc gga aaa aat tgc cga cga           383
Arg Tyr Arg Tyr Arg Gln Arg Gln Ser Gly Gly Lys Asn Cys Arg Arg
            110                 115                 120 agc gcg cga tga tac gcc gca ggc gct gga tgc tgt ttg gga aga aga           431
Ser Ala Arg  *  Tyr Ala Ala Gly Ala Gly Cys Cys Leu Gly Arg Arg
            125                 130                 135 gca ggt taa att ctt tgc tga caa agg ctg cgg cga ttc agc aat cac           479
Ala Gly  *  Ile Leu Cys  *  Gln Arg Leu Arg Arg Phe Ser Asn His
            140                 145                 150 tgc tca tca gcg tcg ctt tgc cgg tgc cgt cgc gcc gca ata tct gaa           527
Cys Ser Ser Ala Ser Leu Cys Arg Cys Arg Arg Ala Ala Ile Ser Glu
            155                 160                 165 tat cct cgg tga gag gct gga gag t                                         552
Tyr Pro Arg  *  Glu Ala Gly Glu
            170                 175
```

<210> SEQ ID NO 54
<211> LENGTH: 175
<212> TYPE: PRT
<213> ORGANISM: Homosapiens
<220> FEATURE:
<223> OTHER INFORMATION: Frame shift sequence

<400> SEQUENCE: 54

```
Ser Ala Arg Cys Pro Gly Pro Val Gln Arg Thr Val Arg Pro Trp Pro
1               5                   10                  15

Arg His Val Thr Val Ala Ile Arg Thr Cys Ser Arg Ile Pro Pro Arg
            20                  25                  30

Pro Gly Asp Gly Gly Pro Ala Gly Ala Val Arg Ala Ala Arg Phe Ala
            35                  40                  45

Val Lys Gln Pro Arg Ile Thr Gly Pro Pro Ala Ala Val Ser Gly Val
    50                  55                  60

Pro Val Ala Ala Ala Arg Arg Ser Arg Gly Arg Phe Glu Arg Tyr
65                  70                  75                  80

Arg Ala Asp Ser Gly Ile Ala Glu Arg Ala Ser Ala Thr Ala Lys Pro
            85                  90                  95

Leu Cys Arg Asp Val Ser Ala Ala Glu Ile Gly Arg Tyr Arg Tyr Arg
            100                 105                 110

Gln Arg Gln Ser Gly Gly Lys Asn Cys Arg Arg Ser Ala Arg Tyr Ala
            115                 120                 125

Ala Gly Ala Gly Cys Cys Leu Gly Arg Arg Ala Gly Ile Leu Cys Gln
            130                 135                 140

Arg Leu Arg Arg Phe Ser Asn His Cys Ser Ser Ala Ser Leu Cys Arg
145                 150                 155                 160

Cys Arg Arg Ala Ala Ile Ser Glu Tyr Pro Arg Glu Ala Gly Glu
            165                 170                 175
```

<210> SEQ ID NO 55
<211> LENGTH: 554
<212> TYPE: DNA

<213> ORGANISM: Homosapiens
<220> FEATURE:
<223> OTHER INFORMATION: Synthetically generated nucleic acid
<223> OTHER INFORMATION: Reverse strand

<400> SEQUENCE: 55

```
actctccagc ctctcaccga ggatattcag atattgcggc gcgacggcac cggcaaagcg      60
acgctgatga gcagtgattg ctgaatcgcc gcagcctttg tcagcaaaga atttaacctg     120
ctcttcttcc caaacagcat ccagcgcctg cggcgtatca tcgcgcgctt cgtcggcaat     180
tttttccgcc actttgtcgc tgtcgatagc aggttatcgg ccaatttcag cagcagatca     240
aacatcacgg cataacggct ttcacgctgt tgcagacgcg cgctcagcaa tgccagaatc     300
ggcgcgatat ctttcaaacc ttccacggct tcgccttgcg gcagctgcga caggtactcc     360
agatatcagc ggcaggtggc cggtaattcg cggctgttta actgcaaacc gtgctgctcg     420
tactgcgcca gcaggtccac catcgcctgg ccgcggtcac gggattcacc gtgaacatgt     480
tcgaatagca acagtgacgt ggcgcggcca tgggcgaaca gttcgctgta ctgggcctgg     540
gcatcgagcg gatc                                                      554
```

<210> SEQ ID NO 56
<211> LENGTH: 179
<212> TYPE: PRT
<213> ORGANISM: Homosapiens
<220> FEATURE:
<223> OTHER INFORMATION: Frame shift sequence
<223> OTHER INFORMATION: Reverse strand

<400> SEQUENCE: 56

```
Thr Leu Gln Pro Leu Thr Glu Asp Ile Gln Ile Leu Arg Arg Asp Gly
  1               5                  10                  15

Thr Gly Lys Ala Thr Leu Met Ser Ser Asp Cys Ile Ala Ala Ala Phe
                 20                  25                  30

Val Ser Lys Glu Phe Asn Leu Leu Phe Phe Pro Asn Ser Ile Gln Arg
             35                  40                  45

Leu Arg Arg Ile Ile Ala Arg Phe Val Gly Asn Phe Phe Arg His Phe
         50                  55                  60

Val Ala Val Asp Ser Gly Ile Gly Gln Phe Gln Gln Ile Lys His
 65                  70                  75                  80

His Gly Ile Thr Ala Phe Thr Leu Leu Gln Thr Arg Ala Gln Gln Cys
                 85                  90                  95

Gln Asn Arg Arg Asp Ile Phe Gln Arg Phe His Gly Phe Ala Leu Arg
                100                 105                 110

Gln Leu Arg Gln Val Leu Gln Ile Gln Arg Gln Val Val Arg Arg Ala
            115                 120                 125

Ala Val Leu Gln Thr Val Leu Leu Val Leu Arg Gln Gln Val His His
        130                 135                 140

Arg Leu Ala Ala Val Thr Gly Phe Thr Val Asn Met Phe Glu Gln Gln
145                 150                 155                 160

Arg Gly Ala Ala Met Gly Glu Gln Phe Ala Val Leu Gly Leu Gly Ile
                165                 170                 175

Glu Arg Ile
```

<210> SEQ ID NO 57
<211> LENGTH: 179
<212> TYPE: PRT
<213> ORGANISM: Homosapiens
<220> FEATURE:

-continued

<223> OTHER INFORMATION: Frame shift sequence
<223> OTHER INFORMATION: Reverse strand

<400> SEQUENCE: 57

Leu Ser Ser Leu Ser Pro Arg Ile Phe Arg Tyr Cys Gly Ala Thr Ala
1               5                   10                  15

Pro Ala Lys Arg Arg Ala Val Ile Ala Glu Ser Pro Gln Pro Leu Ser
            20                  25                  30

Ala Lys Asn Leu Thr Cys Ser Ser Gln Thr Ala Ser Ser Ala Cys
        35                  40                  45

Gly Val Ser Ser Arg Ala Ser Ser Ala Ile Phe Ser Ala Thr Leu Ser
    50                  55                  60

Leu Ser Ile Ala Val Ser Ala Asn Phe Ser Ser Arg Ser Asn Ile Thr
65                  70                  75                  80

Ala Arg Leu Ser Arg Cys Cys Arg Arg Ala Leu Ser Asn Ala Arg Ile
                85                  90                  95

Gly Ala Ile Ser Phe Lys Pro Ser Thr Ala Ser Pro Cys Gly Ser Cys
                100                 105                 110

Asp Arg Tyr Ser Arg Tyr Ser Gly Arg Trp Ser Gly Asn Ser Arg Leu
            115                 120                 125

Phe Asn Cys Lys Pro Cys Cys Ser Tyr Cys Ala Ser Arg Ser Thr Ile
130                 135                 140

Ala Trp Pro Arg Ser Arg Asp Ser Pro Thr Cys Ser Asn Ser Asn Ser
145                 150                 155                 160

Asp Val Ala Arg Pro Trp Ala Asn Ser Ser Leu Tyr Trp Ala Trp Ala
                165                 170                 175

Ser Ser Gly

<210> SEQ ID NO 58
<211> LENGTH: 180
<212> TYPE: PRT
<213> ORGANISM: Homosapiens
<220> FEATURE:
<223> OTHER INFORMATION: Frame shift sequence
<223> OTHER INFORMATION: Reverse strand

<400> SEQUENCE: 58

Ser Pro Ala Ser His Arg Gly Tyr Ser Asp Ile Ala Ala Arg Arg His
1               5                   10                  15

Arg Gln Ser Asp Ala Asp Glu Gln Leu Leu Asn Arg Arg Ser Leu Cys
            20                  25                  30

Gln Gln Arg Ile Pro Ala Leu Leu Pro Lys Gln His Pro Ala Pro Ala
        35                  40                  45

Ala Tyr His Arg Ala Leu Arg Arg Gln Phe Phe Pro Pro Leu Cys Arg
    50                  55                  60

Cys Arg Arg Tyr Arg Pro Ile Ser Ala Ala Asp Gln Thr Ser Arg His
65                  70                  75                  80

Asn Gly Phe His Ala Val Ala Asp Ala Arg Ser Ala Met Pro Glu Ser
                85                  90                  95

Ala Arg Tyr Leu Ser Asn Leu Pro Arg Leu Arg Leu Ala Ala Ala Ala
                100                 105                 110

Thr Gly Thr Pro Asp Thr Ala Ala Gly Gly Pro Val Ile Arg Gly Cys
            115                 120                 125

Leu Arg Ala Asn Arg Ala Ala Arg Thr Ala Pro Ala Gly Pro Pro Ser
130                 135                 140

Pro Gly Arg Gly His Gly Ile His Arg Glu His Val Arg Ile Ala Thr

```
                145                 150                 155                 160
Val Thr Trp Arg Gly His Gly Arg Thr Val Arg Cys Thr Gly Pro Gly
                165                 170                 175

His Arg Ala Asp
            180

<210> SEQ ID NO 59
<211> LENGTH: 265
<212> TYPE: DNA
<213> ORGANISM: Homosapiens
<220> FEATURE:
<221> NAME/KEY: CDS
<222> LOCATION: (1)...(265)
<223> OTHER INFORMATION: N= A,T, C or G
      Xaa= any amino acid
<223> OTHER INFORMATION: Synthetically generated nucleic acid

<400> SEQUENCE: 59 gat cct nac aca nta gcc cgt gga cgc att tgc gtc gac cct cat ang        48
Asp Pro Xaa Thr Xaa Ala Arg Gly Arg Ile Cys Val Asp Pro His Xaa
  1               5                  10                  15 gaa gcg ata cga ggc ggg tna aag tga aca tcc gcc gag cac ggc agc        96
Glu Ala Ile Arg Gly Gly Xaa Lys  *  Thr Ser Ala Glu His Gly Ser
             20                  25                  30 gac gcc tcc gct cac cgt cng cgc agt act tcc tcg ggt cgc cgc gcc      144
Asp Ala Ser Ala His Arg Xaa Arg Ser Thr Ser Ser Gly Arg Arg Ala
         35                  40                  45 tag cac tct gcg ccg tga cat caa ncc gtg aac cca cgg gag act ttg      192
 *  His Ser Ala Pro  *  His Gln Xaa Val Asn Pro Arg Glu Thr Leu
         50                  55                  60 cgc cgc naa ggg atg agt cca cta tta gat gac gca tgg cta cga gcc      240
Arg Arg Xaa Gly Met Ser Pro Leu Leu Asp Asp Ala Trp Leu Arg Ala
         65                  70                  75 nat cct cgg tga naa gct gga gag t                                    265
Xaa Pro Arg  *  Xaa Ala Gly Glu
         80

<210> SEQ ID NO 60
<211> LENGTH: 84
<212> TYPE: PRT
<213> ORGANISM: Homosapiens
<220> FEATURE:
<223> OTHER INFORMATION: Xaa= any amino acid
<223> OTHER INFORMATION: Frame shift sequence

<400> SEQUENCE: 60

Asp Pro Xaa Thr Xaa Ala Arg Gly Arg Ile Cys Val Asp Pro His Xaa
  1               5                  10                  15

Glu Ala Ile Arg Gly Gly Xaa Lys Thr Ser Ala Glu His Gly Ser Asp
             20                  25                  30

Ala Ser Ala His Arg Xaa Arg Ser Thr Ser Ser Gly Arg Arg Ala His
         35                  40                  45

Ser Ala Pro His Gln Xaa Val Asn Pro Arg Glu Thr Leu Arg Arg Xaa
     50                  55                  60

Gly Met Ser Pro Leu Leu Asp Asp Ala Trp Leu Arg Ala Xaa Pro Arg
 65                  70                  75                  80

Xaa Ala Gly Glu

<210> SEQ ID NO 61
<211> LENGTH: 265
<212> TYPE: DNA
<213> ORGANISM: Homosapiens
```

-continued

```
<220> FEATURE:
<221> NAME/KEY: CDS
<222> LOCATION: (2)...(265)
<223> OTHER INFORMATION: N= A,T, C or G
      Xaa= any amino acid
<223> OTHER INFORMATION: Synthetically generated nucleic acid

<400> SEQUENCE: 61 g atc ctn aca can tag ccc gtg gac gca ttt gcg tcg acc ctc ata ngg     49
  Ile Leu Thr Xaa  *  Pro Val Asp Ala Phe Ala Ser Thr Leu Ile Xaa
   1               5                  10                  15 aag cga tac gag gcg ggt naa agt gaa cat ccg ccg agc acg gca gcg       97
Lys Arg Tyr Glu Ala Gly Xaa Ser Glu His Pro Pro Ser Thr Ala Ala
                 20                  25                  30 acg cct ccg ctc acc gtc ngc gca gta ctt cct cgg gtc gcc gcg cct      145
Thr Pro Pro Leu Thr Val Xaa Ala Val Leu Pro Arg Val Ala Ala Pro
             35                  40                  45 agc act ctg cgc cgt gac atc aan ccg tga acc cac ggg aga ctt tgc      193
Ser Thr Leu Arg Arg Asp Ile Xaa Pro  *  Thr His Gly Arg Leu Cys
         50                  55                      60 gcc gcn aag gga tga gtc cac tat tag atg acg cat ggc tac gag ccn      241
Ala Ala Lys Gly  *  Val His Tyr  *  Met Thr His Gly Tyr Glu Pro
         65                          70                  75 atc ctc ggt gan aag ctg gag agt                                      265
Ile Leu Gly Xaa Lys Leu Glu Ser
             80

<210> SEQ ID NO 62
<211> LENGTH: 84
<212> TYPE: PRT
<213> ORGANISM: Homosapiens
<220> FEATURE:
<223> OTHER INFORMATION: Xaa=any amino acid
<223> OTHER INFORMATION: Frame shift sequence

<400> SEQUENCE: 62

Ile Leu Thr Xaa Pro Val Asp Ala Phe Ala Ser Thr Leu Ile Xaa Lys
1               5                   10                  15

Arg Tyr Glu Ala Gly Xaa Ser Glu His Pro Pro Ser Thr Ala Ala Thr
            20                  25                  30

Pro Pro Leu Thr Val Xaa Ala Val Leu Pro Arg Val Ala Ala Pro Ser
        35                  40                  45

Thr Leu Arg Arg Asp Ile Xaa Pro Thr His Gly Arg Leu Cys Ala Ala
    50                  55                  60

Lys Gly Val His Tyr Met Thr His Gly Tyr Glu Pro Ile Leu Gly Xaa
65                  70                  75                  80

Lys Leu Glu Ser

<210> SEQ ID NO 63
<211> LENGTH: 265
<212> TYPE: DNA
<213> ORGANISM: Homosapiens
<220> FEATURE:
<221> NAME/KEY: CDS
<222> LOCATION: (3)...(265)
<223> OTHER INFORMATION: N= A, T, C or G
      Xaa= any amino acid
<223> OTHER INFORMATION: Frame shift sequence

<400> SEQUENCE: 63 ga tcc tna cac ant agc ccg tgg acg cat ttg cgt cga ccc tca tan       47
   Ser Xaa His Xaa Ser Pro Trp Thr His Leu Arg Arg Pro Ser Xaa
    1               5                  10                  15
```

```
gga agc gat acg agg cgg gtn aaa gtg aac atc cgc cga gca cgg cag      95
Gly Ser Asp Thr Arg Arg Val Lys Val Asn Ile Arg Arg Ala Arg Gln
            20                  25                  30 cga cgc ctc cgc tca ccg tcn gcg cag tac ttc ctc ggg tcg ccg cgc     143
Arg Arg Leu Arg Ser Pro Ser Ala Gln Tyr Phe Leu Gly Ser Pro Arg
            35                  40                  45 cta gca ctc tgc gcc gtg aca tca anc cgt gaa ccc acg gga gac ttt     191
Leu Ala Leu Cys Ala Val Thr Ser Xaa Arg Glu Pro Thr Gly Asp Phe
            50                  55                  60 gcg ccg cna agg gat gag tcc act att aga tga cgc atg gct acg agc     239
Ala Pro Xaa Arg Asp Glu Ser Thr Ile Arg  *  Arg Met Ala Thr Ser
        65                  70                  75 cna tcc tcg gtg ana agc tgg aga gt                                   265
Xaa Ser Ser Val Xaa Ser Trp Arg
        80                  85

<210> SEQ ID NO 64
<211> LENGTH: 86
<212> TYPE: PRT
<213> ORGANISM: Homosapiens
<220> FEATURE:
<223> OTHER INFORMATION: Xaa=any amino acid
<223> OTHER INFORMATION: Frame shift sequence

<400> SEQUENCE: 64

Ser Xaa His Xaa Ser Pro Trp Thr His Leu Arg Arg Pro Ser Xaa Gly
1               5                   10                  15

Ser Asp Thr Arg Arg Val Lys Val Asn Ile Arg Arg Ala Arg Gln Arg
            20                  25                  30

Arg Leu Arg Ser Pro Ser Ala Gln Tyr Phe Leu Gly Ser Pro Arg Leu
        35                  40                  45

Ala Leu Cys Ala Val Thr Ser Xaa Arg Glu Pro Thr Gly Asp Phe Ala
    50                  55                  60

Pro Xaa Arg Asp Glu Ser Thr Ile Arg Arg Met Ala Thr Ser Xaa Ser
65                  70                  75                  80

Ser Val Xaa Ser Trp Arg
            85

<210> SEQ ID NO 65
<211> LENGTH: 265
<212> TYPE: DNA
<213> ORGANISM: Homosapiens
<220> FEATURE:
<223> OTHER INFORMATION: N= A, T, C or G
<223> OTHER INFORMATION: Synthetically generated nucleic acid
<223> OTHER INFORMATION: Reverse strand

<400> SEQUENCE: 65
actctccagc ttntcaccga ggatnggctc gtagccatgc gtcatctaat agtggactca      60
tcccttngcg gcgcaaagtc tcccgtgggt tcacggnttg atgtcacggc gcagagtgct    120
aggcgcggcg acccgaggaa gtactgcgcn gacggtgagc ggaggcgtcg ctgccgtgct    180
cggcggatgt tcactttnac ccgcctcgta tcgcttccnt atgagggtcg acgcaaatgc    240
gtccacgggc tantgtgtna ggatc                                          265

<210> SEQ ID NO 66
<211> LENGTH: 88
<212> TYPE: PRT
<213> ORGANISM: Homosapiens
<220> FEATURE:
<223> OTHER INFORMATION: Xaa= any amino acid
<223> OTHER INFORMATION: Frame shift sequence
```

<223> OTHER INFORMATION: Reverse strand

<400> SEQUENCE: 66

Thr Leu Gln Leu Xaa Thr Glu Asp Xaa Leu Val Ala Met Arg His Leu
1               5                   10                  15

Ile Val Asp Ser Ser Leu Xaa Gly Ala Lys Ser Pro Val Gly Ser Arg
            20                  25                  30

Xaa Asp Val Thr Ala Gln Ser Ala Arg Arg Gly Asp Pro Arg Lys Tyr
            35                  40                  45

Cys Xaa Asp Gly Glu Arg Arg Arg Cys Arg Ala Arg Arg Met Phe
    50                  55                  60

Thr Xaa Thr Arg Leu Val Ser Leu Xaa Tyr Glu Gly Arg Arg Lys Cys
65                  70                  75                  80

Val His Gly Leu Xaa Cys Xaa Asp
                85

<210> SEQ ID NO 67
<211> LENGTH: 85
<212> TYPE: PRT
<213> ORGANISM: Homosapiens
<220> FEATURE:
<223> OTHER INFORMATION: Xaa= any amino acid
<223> OTHER INFORMATION: Frame shift sequence
<223> OTHER INFORMATION: Reverse strand

<400> SEQUENCE: 67

Leu Ser Ser Xaa Ser Pro Arg Xaa Gly Ser Pro Cys Val Ile Trp Thr
1               5                   10                  15

His Pro Xaa Ala Ala Gln Ser Leu Pro Trp Val His Xaa Leu Met Ser
            20                  25                  30

Arg Arg Arg Val Leu Gly Ala Ala Thr Arg Gly Ser Thr Ala Xaa Thr
            35                  40                  45

Val Ser Gly Gly Val Ala Ala Val Leu Gly Gly Cys Ser Leu Xaa Pro
    50                  55                  60

Ala Ser Tyr Arg Phe Xaa Met Arg Val Asp Ala Asn Ala Ser Thr Gly
65                  70                  75                  80

Xaa Cys Xaa Arg Ile
            85

<210> SEQ ID NO 68
<211> LENGTH: 83
<212> TYPE: PRT
<213> ORGANISM: Homosapiens
<220> FEATURE:
<223> OTHER INFORMATION: Xaa= any amino acid
<223> OTHER INFORMATION: Frame shift sequence
<223> OTHER INFORMATION: Reverse strand

<400> SEQUENCE: 68

Ser Pro Ala Xaa His Arg Gly Xaa Ala Arg Ser His Ala Ser Ser Asn
1               5                   10                  15

Ser Gly Leu Ile Pro Xaa Arg Arg Lys Val Ser Arg Gly Phe Thr Xaa
            20                  25                  30

Cys His Gly Ala Glu Cys Ala Arg Arg Pro Glu Glu Val Leu Arg Xaa
            35                  40                  45

Arg Ala Glu Ala Ser Leu Pro Cys Ser Ala Asp Val His Phe Xaa Pro
    50                  55                  60

Pro Arg Ile Ala Ser Xaa Gly Ser Thr Gln Met Arg Pro Arg Ala Xaa
65                  70                  75                  80

```
Val Xaa Gly

<210> SEQ ID NO 69
<211> LENGTH: 317
<212> TYPE: DNA
<213> ORGANISM: Homosapiens
<220> FEATURE:
<221> NAME/KEY: CDS
<222> LOCATION: (1)...(317)
<223> OTHER INFORMATION: N= A,T, C or G
      Xaa= any amino acid
<223> OTHER INFORMATION: Synthetically generated nucleic acid

<400> SEQUENCE: 69 gat ccg gcc ncg cac gan ctt acc ggt naa aac ttc cnc ncc nat aat      48
Asp Pro Ala Xaa His Xaa Leu Thr Gly Xaa Asn Phe Xaa Xaa Xaa Asn
 1               5                  10                  15 att tgc cgc gcg agc cgc cct gan gct ctc ggc gta act ccg gat gca      96
Ile Cys Arg Ala Ser Arg Pro Xaa Ala Leu Gly Val Thr Pro Asp Ala
             20                  25                  30 cgg ggg acc gtg acg gtt gta ntg ccc tgg ctt ttc tca gcn gaa atc     144
Arg Gly Thr Val Thr Val Val Xaa Pro Trp Leu Phe Ser Ala Glu Ile
         35                  40                  45 tgc aca gcc atc ttc cga tcg atc tgg cgc agg tgg ggc ggc nca aaa     192
Cys Thr Ala Ile Phe Arg Ser Ile Trp Arg Arg Trp Gly Gly Xaa Lys
     50                  55                  60 cgg tgg gca tct cca aac cgc agg aac gtg ttt tgc agg atg tcg aac     240
Arg Trp Ala Ser Pro Asn Arg Arg Asn Val Phe Cys Arg Met Ser Asn
 65                  70                  75                  80 atc atc cac gct tcg gtn ccc aac ggc tac ttc gcc cgg tac cgg gcc     288
Ile Ile His Ala Ser Val Pro Asn Gly Tyr Phe Ala Arg Tyr Arg Ala
                 85                  90                  95 atg tca tcc tcg gtg ana agc tgg ana nt                              317
Met Ser Ser Ser Val Xaa Ser Trp Xaa
             100                 105

<210> SEQ ID NO 70
<211> LENGTH: 105
<212> TYPE: PRT
<213> ORGANISM: Homosapiens
<220> FEATURE:
<223> OTHER INFORMATION: Xaa= any amino acid
<223> OTHER INFORMATION: Frame shift sequence

<400> SEQUENCE: 70

Asp Pro Ala Xaa His Xaa Leu Thr Gly Xaa Asn Phe Xaa Xaa Xaa Asn
 1               5                  10                  15

Ile Cys Arg Ala Ser Arg Pro Xaa Ala Leu Gly Val Thr Pro Asp Ala
             20                  25                  30

Arg Gly Thr Val Thr Val Xaa Pro Trp Leu Phe Ser Ala Glu Ile
         35                  40                  45

Cys Thr Ala Ile Phe Arg Ser Ile Trp Arg Arg Trp Gly Gly Xaa Lys
     50                  55                  60

Arg Trp Ala Ser Pro Asn Arg Arg Asn Val Phe Cys Arg Met Ser Asn
 65                  70                  75                  80

Ile Ile His Ala Ser Val Pro Asn Gly Tyr Phe Ala Arg Tyr Arg Ala
                 85                  90                  95

Met Ser Ser Ser Val Xaa Ser Trp Xaa
             100                 105

<210> SEQ ID NO 71
<211> LENGTH: 317
```

-continued

```
<212> TYPE: DNA
<213> ORGANISM: Homosapiens
<220> FEATURE:
<221> NAME/KEY: CDS
<222> LOCATION: (2)...(317)
<223> OTHER INFORMATION: N= A, T, C or G
      Xaa= any amino acid
<223> OTHER INFORMATION: Synthetically generated nucleic acid

<400> SEQUENCE: 71 g atc cgg ccn cgc acg anc tta ccg gtn aaa act tcc ncn ccn ata ata        49
  Ile Arg Pro Arg Thr Xaa Leu Pro Val Lys Thr Ser Xaa Pro Ile Ile
  1               5                   10                  15 ttt gcc gcg cga gcc gcc ctg ang ctc tcg gcg taa ctc cgg atg cac          97
Phe Ala Ala Arg Ala Ala Leu Xaa Leu Ser Ala  *  Leu Arg Met His
             20                  25                  30 ggg gga ccg tga cgg ttg tan tgc cct ggc ttt tct cag cng aaa tct         145
Gly Gly Pro  *  Arg Leu Xaa Cys Pro Gly Phe Ser Gln Xaa Lys Ser
             35                  40                  45 gca cag cca tct tcc gat cga tct ggc gca ggt ggg gcg gcn caa aac         193
Ala Gln Pro Ser Ser Asp Arg Ser Gly Ala Gly Gly Ala Ala Gln Asn
             50                  55                  60 ggt ggg cat ctc caa acc gca gga acg tgt ttt gca gga tgt cga aca         241
Gly Gly His Leu Gln Thr Ala Gly Thr Cys Phe Ala Gly Cys Arg Thr
             65                  70                  75 tca tcc acg ctt cgg tnc cca acg gct act tcg ccc ggt acc ggg cca         289
Ser Ser Thr Leu Arg Xaa Pro Thr Ala Thr Ser Pro Gly Thr Gly Pro
 80                  85                  90 tgt cat cct cgg tga naa gct gga nan t                                   317
Cys His Pro Arg  *  Xaa Ala Gly Xaa
 95                  100

<210> SEQ ID NO 72
<211> LENGTH: 102
<212> TYPE: PRT
<213> ORGANISM: Homosapiens
<220> FEATURE:
<223> OTHER INFORMATION: Xaa= any amino acid
<223> OTHER INFORMATION: Frame shift sequence

<400> SEQUENCE: 72

Ile Arg Pro Arg Thr Xaa Leu Pro Val Lys Thr Ser Xaa Pro Ile Ile
1               5                   10                  15

Phe Ala Ala Arg Ala Ala Leu Xaa Leu Ser Ala Leu Arg Met His Gly
             20                  25                  30

Gly Pro Arg Leu Xaa Cys Pro Gly Phe Ser Gln Xaa Lys Ser Ala Gln
         35                  40                  45

Pro Ser Ser Asp Arg Ser Gly Ala Gly Ala Ala Gln Asn Gly Gly
     50                  55                  60

His Leu Gln Thr Ala Gly Thr Cys Phe Ala Gly Cys Arg Thr Ser Ser
65                  70                  75                  80

Thr Leu Arg Xaa Pro Thr Ala Thr Ser Pro Gly Thr Gly Pro Cys His
                 85                  90                  95

Pro Arg Xaa Ala Gly Xaa
            100

<210> SEQ ID NO 73
<211> LENGTH: 317
<212> TYPE: DNA
<213> ORGANISM: Homosapiens
<220> FEATURE:
<221> NAME/KEY: CDS
<222> LOCATION: (3)...(317)
```

```
<223> OTHER INFORMATION: N= A, T, C or G
     Xaa= any amino acid
<223> OTHER INFORMATION: Synthetically generated nucleic acid

<400> SEQUENCE: 73 ga tcc ggc cnc gca cga nct tac cgg tna aaa ctt ccn cnc cna taa       47
   Ser Gly Xaa Ala Arg Xaa Tyr Arg Xaa Lys Leu Pro Xaa Xaa  *
    1               5                  10 tat ttg ccg cgc gag ccg ccc tga ngc tct cgg cgt aac tcc gga tgc      95
Tyr Leu Pro Arg Glu Pro Pro  *  Xaa Ser Arg Arg Asn Ser Gly Cys
 15              20                  25 acg ggg gac cgt gac ggt tgt ant gcc ctg gct ttt ctc agc nga aat     143
Thr Gly Asp Arg Asp Gly Cys Xaa Ala Leu Ala Phe Leu Ser Xaa Asn
 30              35                  40                  45 ctg cac agc cat ctt ccg atc gat ctg gcg cag gtg ggg cgg cnc aaa     191
Leu His Ser His Leu Pro Ile Asp Leu Ala Gln Val Gly Arg Xaa Lys
             50                  55                  60 acg gtg ggc atc tcc aaa ccg cag gaa cgt gtt ttg cag gat gtc gaa     239
Thr Val Gly Ile Ser Lys Pro Gln Glu Arg Val Leu Gln Asp Val Glu
             65                  70                  75 cat cat cca cgc ttc ggt ncc caa cgg cta ctt cgc ccg gta ccg ggc     287
His His Pro Arg Phe Gly Xaa Gln Arg Leu Leu Arg Pro Val Pro Gly
             80                  85                  90 cat gtc atc ctc ggt gan aag ctg gan ant                             317
His Val Ile Leu Gly Xaa Lys Leu Xaa Xaa
             95                 100

<210> SEQ ID NO 74
<211> LENGTH: 103
<212> TYPE: PRT
<213> ORGANISM: Homosapiens
<220> FEATURE:
<223> OTHER INFORMATION: Xaa= any amino acid
<223> OTHER INFORMATION: Frame shift sequence

<400> SEQUENCE: 74

Ser Gly Xaa Ala Arg Xaa Tyr Arg Xaa Lys Leu Pro Xaa Xaa Tyr Leu
 1               5                  10                  15

Pro Arg Glu Pro Pro Xaa Ser Arg Arg Asn Ser Gly Cys Thr Gly Asp
             20                  25                  30

Arg Asp Gly Cys Xaa Ala Leu Ala Phe Leu Ser Xaa Asn Leu His Ser
         35                  40                  45

His Leu Pro Ile Asp Leu Ala Gln Val Gly Arg Xaa Lys Thr Val Gly
     50                  55                  60
65
Ile Ser Lys Pro Gln Glu Arg Val Leu Gln Asp Val Glu His His Pro
65                  70                  75                  80

Arg Phe Gly Xaa Gln Arg Leu Leu Arg Pro Val Pro Gly His Val Ile
             85                  90                  95

Leu Gly Xaa Lys Leu Xaa Xaa
            100

<210> SEQ ID NO 75
<211> LENGTH: 316
<212> TYPE: DNA
<213> ORGANISM: Homosapiens
<220> FEATURE:
<223> OTHER INFORMATION: N= A, T, C or G
<223> OTHER INFORMATION: Synthetically generated nucleic acid
<223> OTHER INFORMATION: Reverse strand

<400> SEQUENCE: 75
antntccagc ttntcaccga ggatgacatg gcccggtacc gggcgaagta gccgttgggn     60
```

```
accgaagcgt ggatgatgtt cgacatcctg caaaacacgt tcctgcggtt tggagatgcc    120
caccgttttg ngccgcccac ctgcgccaga tcgatcggaa gatggctgtg cagatttcng    180
ctgagaaaag ccagggcant acaaccgtca cggtccccg tgcatccgga gttacgccga    240
gagcntcagg gcggctcgcg cggcaaatat tatnggngng aagttttna ccggtaagnt    300 cgtgcgnggc cggatc                                                   316
```

<210> SEQ ID NO 76
<211> LENGTH: 104
<212> TYPE: PRT
<213> ORGANISM: Homosapiens
<220> FEATURE:
<223> OTHER INFORMATION: Xaa= any amino acid
<223> OTHER INFORMATION: Frame shift sequence
<223> OTHER INFORMATION: Reverse strand

<400> SEQUENCE: 76

```
Xaa Xaa Gln Leu Xaa Thr Glu Asp Asp Met Ala Arg Tyr Arg Ala Lys
1               5                   10                  15

Pro Leu Xaa Thr Glu Ala Trp Met Met Phe Asp Ile Leu Gln Asn Thr
            20                  25                  30

Phe Leu Arg Phe Gly Asp Ala His Arg Phe Xaa Pro Pro His Leu Arg
        35                  40                  45

Gln Ile Asp Arg Lys Met Ala Val Gln Ile Xaa Ala Glu Lys Ser Gln
    50                  55                  60

Gly Xaa Thr Thr Val Thr Val Pro Arg Ala Ser Gly Val Thr Pro Arg
65                  70                  75                  80

Xaa Ser Gly Arg Leu Ala Arg Gln Ile Leu Xaa Xaa Xaa Lys Phe Xaa
                85                  90                  95

Pro Val Xaa Ser Cys Xaa Ala Gly
            100
```

<210> SEQ ID NO 77
<211> LENGTH: 103
<212> TYPE: PRT
<213> ORGANISM: Homosapiens
<220> FEATURE:
<223> OTHER INFORMATION: Xaa= any amino acid
<223> OTHER INFORMATION: Frame shift sequence
<223> OTHER INFORMATION: Reverse strand

<400> SEQUENCE: 77

```
Xaa Ser Ser Xaa Ser Pro Arg Met Thr Trp Pro Gly Thr Gly Arg Ser
1               5                   10                  15

Ser Arg Trp Xaa Pro Lys Arg Gly Cys Ser Thr Ser Cys Lys Thr Arg
            20                  25                  30

Ser Cys Gly Leu Arg Met Pro Thr Val Leu Xaa Arg Pro Thr Cys Ala
        35                  40                  45

Arg Ser Ile Gly Arg Trp Leu Cys Arg Phe Xaa Leu Arg Lys Ala Arg
    50                  55                  60

Ala Xaa Gln Pro Ser Arg Ser Pro Val His Pro Glu Leu Arg Arg Glu
65                  70                  75                  80

Xaa Gln Gly Gly Ser Arg Gly Lys Tyr Tyr Xaa Xaa Gly Ser Phe Xaa
                85                  90                  95

Arg Xaa Arg Ala Xaa Pro Asp
            100
```

<210> SEQ ID NO 78

-continued

```
<211> LENGTH: 103
<212> TYPE: PRT
<213> ORGANISM: Homosapiens
<220> FEATURE:
<223> OTHER INFORMATION: Xaa= any amino acid
<223> OTHER INFORMATION: Frame shift sequence
<223> OTHER INFORMATION: Reverse strand

<400> SEQUENCE: 78

Xaa Pro Ala Xaa His Arg Gly His Gly Pro Val Pro Gly Glu Val Ala
1               5                   10                  15

Val Gly Xaa Arg Ser Val Asp Asp Val Arg His Pro Ala Lys His Val
            20                  25                  30

Pro Ala Val Trp Arg Cys Pro Pro Phe Xaa Ala Ala Pro Pro Ala Pro
        35                  40                  45

Asp Arg Ser Glu Asp Gly Cys Ala Asp Phe Xaa Glu Lys Pro Gly Xaa
    50                  55                  60

Tyr Asn Arg His Gly Pro Pro Cys Ile Arg Ser Tyr Ala Glu Ser Xaa
65                  70                  75                  80

Arg Ala Ala Arg Ala Ala Asn Ile Xaa Xaa Xaa Glu Val Xaa Thr Gly
                85                  90                  95

Lys Xaa Val Xaa Gly Arg Ile
            100

<210> SEQ ID NO 79
<211> LENGTH: 341
<212> TYPE: DNA
<213> ORGANISM: Homosapiens
<220> FEATURE:
<221> NAME/KEY: CDS
<222> LOCATION: (1)...(341)
<223> OTHER INFORMATION: N= A, T, C or G
      Xaa= any amino acid
<223> OTHER INFORMATION: Synthetically generated nucleic acid

<400> SEQUENCE: 79 act ctc cag cct cgc acc gag gat cag ggc gtc gtc gac tcc gtc gac        48
Thr Leu Gln Pro Arg Thr Glu Asp Gln Gly Val Val Asp Ser Val Asp
1               5                   10                  15 ctg acc gcc tcc ccn ccg ctg ctc tcg atc ggc ggc cag acc tac acc        96
Leu Thr Ala Ser Pro Pro Leu Leu Ser Ile Gly Gly Gln Thr Tyr Thr
            20                  25                  30 anc gac gta gat caa gcg cgt ggt gcg cgg cgc nac nag can can cta       144
Xaa Asp Val Asp Gln Ala Arg Gly Ala Arg Arg Xaa Xaa Xaa Xaa Leu
        35                  40                  45 ant caa ggc ctc gct gca tcc cgc caa tcc agc gct cag ctt cgc ggg       192
Xaa Gln Gly Leu Ala Ala Ser Arg Gln Ser Ser Ala Gln Leu Arg Gly
    50                  55                  60 aat tgc gcg anc gct ttt gcg cgt cnc gag tna ccg cat aca cac ctg       240
Asn Cys Ala Xaa Ala Phe Ala Arg Xaa Glu Xaa Pro His Thr His Leu
65                  70                  75                  80 ccg tcc ctg cga aag caa gga ccc ata ctc cgc ngc ggg tgt tgt tga       288
Pro Ser Leu Arg Lys Gln Gly Pro Ile Leu Arg Xaa Gly Cys Cys  *
                85                  90                  95 cgg gac tcg tca tgg cgg caa cgc aca acg tnn aac ttc tgt ggt tat       336
Arg Asp Ser Ser Trp Arg Gln Arg Thr Thr Xaa Asn Phe Cys Gly Tyr
                100                 105                 110 gga tc                                                                 341
Gly

<210> SEQ ID NO 80
<211> LENGTH: 112
```

-continued

```
<212> TYPE: PRT
<213> ORGANISM: Homosapiens
<220> FEATURE:
<223> OTHER INFORMATION: Xaa= any amino acid
<223> OTHER INFORMATION: Frame shift sequence

<400> SEQUENCE: 80

Thr Leu Gln Pro Arg Thr Glu Asp Gln Gly Val Val Asp Ser Val Asp
1               5                   10                  15

Leu Thr Ala Ser Pro Pro Leu Leu Ser Ile Gly Gly Gln Thr Tyr Thr
            20                  25                  30

Xaa Asp Val Asp Gln Ala Arg Gly Ala Arg Arg Xaa Xaa Xaa Leu
        35                  40                  45

Xaa Gln Gly Leu Ala Ala Ser Arg Gln Ser Ser Ala Gln Leu Arg Gly
    50                  55                  60

Asn Cys Ala Xaa Ala Phe Ala Arg Xaa Glu Xaa Pro His Thr His Leu
65                  70                  75                  80

Pro Ser Leu Arg Lys Gln Gly Pro Ile Leu Arg Xaa Gly Cys Cys Arg
                85                  90                  95

Asp Ser Ser Trp Arg Gln Arg Thr Thr Xaa Asn Phe Cys Gly Tyr Gly
            100                 105                 110

<210> SEQ ID NO 81
<211> LENGTH: 341
<212> TYPE: DNA
<213> ORGANISM: Homosapiens
<220> FEATURE:
<221> NAME/KEY: CDS
<222> LOCATION: (2)...(341)
<223> OTHER INFORMATION: N= A, T, C or G
      Xaa= any amino acid
<223> OTHER INFORMATION: Synthetically generated nucleic acid

<400> SEQUENCE: 81 a ctc tcc agc ctc gca ccg agg atc agg gcg tcg tcg act ccg tcg acc      49
  Leu Ser Ser Leu Ala Pro Arg Ile Arg Ala Ser Ser Thr Pro Ser Thr
  1               5                   10                  15 tga ccg cct ccc cnc cgc tgc tct cga tcg gcg gcc aga cct aca cca        97
 *  Pro Pro Pro Xaa Arg Cys Ser Arg Ser Ala Ala Arg Pro Thr Pro
                20                  25                  30 ncg acg tag atc aag cgc gtg gtg cgc ggc gcn acn agc anc anc taa       145
Xaa Thr  *  Ile Lys Arg Val Val Arg Gly Ala Thr Ser Xaa Xaa  *
         35                  40                  45 ntc aag gcc tcg ctg cat ccc gcc aat cca gcg ctc agc ttc gcg gga       193
Xaa Lys Ala Ser Leu His Pro Ala Asn Pro Ala Leu Ser Phe Ala Gly
        50                  55                  60 att gcg cga ncg ctt ttg cgc gtc ncg agt nac cgc ata cac acc tgc       241
Ile Ala Arg Xaa Leu Leu Arg Val Xaa Ser Xaa Arg Ile His Thr Cys
            65                  70                  75 cgt ccc tgc gaa agc aag gac cca tac tcc gcn gcg ggt gtt gtt gac       289
Arg Pro Cys Glu Ser Lys Asp Pro Tyr Ser Ala Ala Gly Val Val Asp
        80                  85                  90 ggg act cgt cat ggc ggc aac gca caa cgt nna act tct gtg gtt atg       337
Gly Thr Arg His Gly Gly Asn Ala Gln Arg Xaa Thr Ser Val Val Met
    95                  100                 105 gat c                                                                  341
Asp
110

<210> SEQ ID NO 82
<211> LENGTH: 110
<212> TYPE: PRT
```

<213> ORGANISM: Homosapiens
<220> FEATURE:
<223> OTHER INFORMATION: Xaa= any amino acid
<223> OTHER INFORMATION: Frame shift sequence

<400> SEQUENCE: 82

```
Leu Ser Ser Leu Ala Pro Arg Ile Arg Ala Ser Ser Thr Pro Ser Thr
1               5                   10                  15

Pro Pro Pro Xaa Arg Cys Ser Arg Ser Ala Ala Arg Pro Thr Pro Xaa
                20                  25                  30

Thr Ile Lys Arg Val Val Arg Gly Ala Thr Ser Xaa Xaa Xaa Lys Ala
            35                  40                  45

Ser Leu His Pro Ala Asn Pro Ala Leu Ser Phe Ala Gly Ile Ala Arg
        50                  55                  60

Xaa Leu Leu Arg Val Xaa Ser Xaa Arg Ile His Thr Cys Arg Pro Cys
65                  70                  75                  80

Glu Ser Lys Asp Pro Tyr Ser Ala Ala Gly Val Val Asp Gly Thr Arg
                85                  90                  95

His Gly Gly Asn Ala Gln Arg Xaa Thr Ser Val Val Met Asp
            100                 105                 110
```

<210> SEQ ID NO 83
<211> LENGTH: 341
<212> TYPE: DNA
<213> ORGANISM: Homosapiens
<220> FEATURE:
<221> NAME/KEY: CDS
<222> LOCATION: (3)...(341)
<223> OTHER INFORMATION: N= A, T, C or G
      Xaa= any amino acid
<223> OTHER INFORMATION: Synthetically generated nucleic acid

<400> SEQUENCE: 83

```
ac tct cca gcc tcg cac cga gga tca ggg cgt cgt cga ctc cgt cga        47
   Ser Pro Ala Ser His Arg Gly Ser Gly Arg Arg Arg Leu Arg Arg
   1               5                   10                  15 cct gac cgc ctc ccc ncc gct gct ctc gat cgg cgg cca gac cta cac       95
Pro Asp Arg Leu Pro Xaa Ala Ala Leu Asp Arg Arg Pro Asp Leu His
                20                  25                  30 can cga cgt aga tca agc gcg tgg tgc gcg gcg cna cna gca nca nct       143
Xaa Arg Arg Arg Ser Ser Ala Trp Cys Ala Ala Xaa Xaa Ala Xaa Xaa
                35                  40                  45 aan tca agg cct cgc tgc atc ccg cca atc cag cgc tca gct tcg cgg       191
Xaa Ser Arg Pro Arg Cys Ile Pro Pro Ile Gln Arg Ser Ala Ser Arg
        50                  55                  60 gaa ttg cgc gan cgc ttt tgc gcg tcn cga gtn acc gca tac aca cct       239
Glu Leu Arg Xaa Arg Phe Cys Ala Ser Arg Val Thr Ala Tyr Thr Pro
65                  70                  75 gcc gtc cct gcg aaa gca agg acc cat act ccg cng cgg gtg ttg ttg       287
Ala Val Pro Ala Lys Ala Arg Thr His Thr Pro Xaa Arg Val Leu Leu
 80                  85                  90                  95 acg gga ctc gtc atg gcg gca acg cac aac gtn naa ctt ctg tgg tta       335
Thr Gly Leu Val Met Ala Ala Thr His Asn Val Xaa Leu Leu Trp Leu
                100                 105                 110 tgg atc                                                               341
Trp Ile
```

<210> SEQ ID NO 84
<211> LENGTH: 113
<212> TYPE: PRT
<213> ORGANISM: Homosapiens
<220> FEATURE:

```
<223> OTHER INFORMATION: Xaa= any amino acid
<223> OTHER INFORMATION: Frame shift sequence

<400> SEQUENCE: 84

Ser Pro Ala Ser His Arg Gly Ser Gly Arg Arg Leu Arg Arg Pro
1               5                   10                  15

Asp Arg Leu Pro Xaa Ala Ala Leu Asp Arg Arg Pro Asp Leu His Xaa
                20                  25                  30

Arg Arg Arg Ser Ser Ala Trp Cys Ala Ala Xaa Xaa Ala Xaa Xaa Xaa
            35                  40                  45

Ser Arg Pro Arg Cys Ile Pro Pro Ile Gln Arg Ser Ala Ser Arg Glu
50                  55                  60

Leu Arg Xaa Arg Phe Cys Ala Ser Arg Val Thr Ala Tyr Thr Pro Ala
65                  70                  75                  80

Val Pro Ala Lys Ala Arg Thr His Thr Pro Xaa Arg Val Leu Leu Thr
                85                  90                  95

Gly Leu Val Met Ala Ala Thr His Asn Val Xaa Leu Leu Trp Leu Trp
                100                 105                 110

Ile

<210> SEQ ID NO 85
<211> LENGTH: 342
<212> TYPE: DNA
<213> ORGANISM: Homosapiens
<220> FEATURE:
<223> OTHER INFORMATION: N= A, T, C or G
<223> OTHER INFORMATION: synthetically generated nucleic acid
<223> OTHER INFORMATION: Reverse strand

<400> SEQUENCE: 85
gatccataac cacagaagtt nnacgttgtg cgttgccgcc atgacgagtc ccgtcaacaa      60
cacccgcngc ggagtatggg tccttgcttt cgcaggacg gcaggtgtgt atgcggtnac      120
tcgngacgcg caaaagcgnt cgcgcaattc ccgcgaagct gagcgcgtgg attggcggga    180
tgcagcgagg ccttganttta gntgntgctn gtngcgccgc gcaccacgcg cttgatctac    240
gtcgntggtg taggtctggc cgccgatcga gagcagcggn ggggaggcgg tcaggtcgac    300
ggagtcgacg acgccctgat cctcggtgcg aggctggaga gt                       342

<210> SEQ ID NO 86
<211> LENGTH: 107
<212> TYPE: PRT
<213> ORGANISM: Homosapiens
<220> FEATURE:
<223> OTHER INFORMATION: Xaa= any amino acid
<223> OTHER INFORMATION: Frame shift sequence
<223> OTHER INFORMATION: Reverse strand

<400> SEQUENCE: 86

Asp Pro Pro Gln Lys Xaa Xaa Val Val Arg Cys Arg His Asp Glu Ser
1               5                   10                  15

Arg Gln Gln His Pro Xaa Arg Ser Met Gly Pro Cys Phe Arg Arg Asp
                20                  25                  30

Gly Arg Cys Val Cys Gly Xaa Ser Xaa Arg Ala Lys Ala Xaa Ala Gln
            35                  40                  45

Phe Pro Arg Ser Ala Leu Asp Trp Arg Asp Ala Ala Arg Pro Xaa Xaa
50                  55                  60

Xaa Cys Xaa Xaa Arg Arg Ala Pro Arg Ala Ser Thr Ser Xaa Val Val
65                  70                  75                  80
```

```
Trp Pro Pro Ile Glu Ser Ser Xaa Gly Glu Ala Val Arg Ser Thr Glu
                85                  90                  95

Ser Thr Thr Pro Ser Ser Val Arg Gly Trp Arg
                100                 105
```

<210> SEQ ID NO 87
<211> LENGTH: 113
<212> TYPE: PRT
<213> ORGANISM: Homosapiens
<220> FEATURE:
<223> OTHER INFORMATION: Xaa= any amino acid
<223> OTHER INFORMATION: Frame shift sequence
<223> OTHER INFORMATION: Reverse strand

<400> SEQUENCE: 87

```
Ile His Asn His Arg Ser Xaa Thr Leu Cys Val Ala Ala Met Thr Ser
1               5                   10                  15

Pro Val Asn Asn Thr Arg Xaa Gly Val Trp Val Leu Ala Phe Ala Gly
                20                  25                  30

Arg Ala Gly Val Tyr Ala Xaa Thr Xaa Asp Ala Gln Lys Xaa Ser Arg
            35                  40                  45

Asn Ser Arg Glu Ala Glu Arg Trp Ile Gly Gly Met Gln Arg Gly Leu
        50                  55                  60

Xaa Leu Xaa Xaa Ala Xaa Xaa Ala Ala His His Ala Leu Asp Leu Arg
65                  70                  75                  80

Xaa Trp Cys Arg Ser Gly Arg Arg Ser Arg Ala Ala Xaa Gly Arg Arg
                85                  90                  95

Ser Gly Arg Arg Ser Arg Arg Pro Asp Pro Arg Cys Glu Ala Gly
                100                 105                 110

Glu
```

<210> SEQ ID NO 88
<211> LENGTH: 111
<212> TYPE: PRT
<213> ORGANISM: Homosapiens
<220> FEATURE:
<223> OTHER INFORMATION: Xaa= any amino acid
<223> OTHER INFORMATION: Frame shift sequence
<223> OTHER INFORMATION: Reverse strand

<400> SEQUENCE: 88

```
Ser Ile Thr Thr Glu Val Xaa Arg Cys Ala Leu Pro Pro Arg Val Pro
1               5                   10                  15

Ser Thr Thr Pro Xaa Ala Glu Tyr Gly Ser Leu Leu Ser Gln Gly Arg
                20                  25                  30

Gln Val Cys Met Arg Xaa Leu Xaa Thr Arg Lys Ser Xaa Arg Ala Ile
            35                  40                  45

Pro Ala Lys Leu Ser Ala Gly Leu Ala Gly Cys Ser Glu Ala Leu Xaa
        50                  55                  60

Xaa Xaa Xaa Xaa Ala Pro Arg Thr Thr Arg Leu Ile Tyr Val Xaa Gly
65                  70                  75                  80

Val Gly Leu Ala Ala Asp Arg Glu Gln Arg Xaa Gly Gly Gly Gln Val
                85                  90                  95

Asp Gly Val Asp Asp Ala Leu Ile Leu Gly Ala Arg Leu Glu Ser
                100                 105                 110
```

<210> SEQ ID NO 89
<211> LENGTH: 256
<212> TYPE: DNA
<213> ORGANISM: Homosapiens -continued

```
<220> FEATURE:
<221> NAME/KEY: CDS
<222> LOCATION: (1)...(256)
<223> OTHER INFORMATION: N= A, T, C or G
      Xaa= any amino acid
<223> OTHER INFORMATION: Synthetically generated nucleic acid

<400> SEQUENCE: 89 gat ccg cgc atc ctc tct gtg gct ctc gcg ggg tca gag gtg gat aag      48
Asp Pro Arg Ile Leu Ser Val Ala Leu Ala Gly Ser Glu Val Asp Lys
 1               5                  10                  15 gcc ggc cgc aag ctc gga ctt ccc gtc nca atc naa ggc ttc tgc gat      96
Ala Gly Arg Lys Leu Gly Leu Pro Val Xaa Ile Xaa Gly Phe Cys Asp
             20                  25                  30 cnc can tac aac tac nac ggc aat ctn aca tca cgc aag atc gca ngc     144
Xaa Xaa Tyr Asn Tyr Xaa Gly Asn Leu Thr Ser Arg Lys Ile Ala Xaa
         35                  40                  45 tcn gtc atc aag gac gcn gcg gtc ncc ncc cgg cag gtg ctc nat atn     192
Ser Val Ile Lys Asp Ala Ala Val Xaa Xaa Arg Gln Val Leu Xaa Xaa
     50                  55                  60 gtg ttg aan aac acc atc gct cct gca acg gca aga aga tca cat gca     240
Val Leu Xaa Asn Thr Ile Ala Pro Ala Thr Ala Arg Arg Ser His Ala
 65                  70                  75                  80 agg tcc act cgc tgt g                                               256
Arg Ser Thr Arg Cys
             85

<210> SEQ ID NO 90
<211> LENGTH: 85
<212> TYPE: PRT
<213> ORGANISM: Homosapiens
<220> FEATURE:
<223> OTHER INFORMATION: Xaa= any amino acid
<223> OTHER INFORMATION: Frame shift sequence

<400> SEQUENCE: 90

Asp Pro Arg Ile Leu Ser Val Ala Leu Ala Gly Ser Glu Val Asp Lys
 1               5                  10                  15

Ala Gly Arg Lys Leu Gly Leu Pro Val Xaa Ile Xaa Gly Phe Cys Asp
             20                  25                  30

Xaa Xaa Tyr Asn Tyr Xaa Gly Asn Leu Thr Ser Arg Lys Ile Ala Xaa
         35                  40                  45

Ser Val Ile Lys Asp Ala Ala Val Xaa Xaa Arg Gln Val Leu Xaa Xaa
     50                  55                  60

Val Leu Xaa Asn Thr Ile Ala Pro Ala Thr Ala Arg Arg Ser His Ala
 65                  70                  75                  80

Arg Ser Thr Arg Cys
             85

<210> SEQ ID NO 91
<211> LENGTH: 256
<212> TYPE: DNA
<213> ORGANISM: Homosapiens
<220> FEATURE:
<221> NAME/KEY: CDS
<222> LOCATION: (2)...(256)
<223> OTHER INFORMATION: N= A, T, C or G
      Xaa= any amino acid
<223> OTHER INFORMATION: Synthetically generated nucleic acid

<400> SEQUENCE: 91 g atc cgc gca tcc tct ctg tgg ctc tcg cgg ggt cag agg tgg ata agg    49
  Ile Arg Ala Ser Ser Leu Trp Leu Ser Arg Gly Gln Arg Trp Ile Arg
   1               5                  10                  15
```

```
ccg gcc gca agc tcg gac ttc ccg tcn caa tcn aag gct tct gcg atc      97
Pro Ala Ala Ser Ser Asp Phe Pro Ser Gln Ser Lys Ala Ser Ala Ile
            20                  25                  30 ncc ant aca act acn acg gca atc tna cat cac gca aga tcg can gct     145
Xaa Xaa Thr Thr Thr Thr Ala Ile Xaa His His Ala Arg Ser Xaa Ala
        35                  40                  45 cng tca tca agg acg cng cgg tcn ccn ccc ggc agg tgc tcn ata tng     193
Xaa Ser Ser Arg Thr Xaa Arg Ser Pro Pro Gly Arg Cys Ser Ile Xaa
    50                  55                  60 tgt tga ana aca cca tcg ctc ctg caa cgg caa gaa gat cac atg caa     241
Cys  *  Xaa Thr Pro Ser Leu Leu Gln Arg Gln Glu Asp His Met Gln
65                  70                  75 ggt cca ctc gct gtg                                                  256
Gly Pro Leu Ala Val
 80
```

```
<210> SEQ ID NO 92
<211> LENGTH: 84
<212> TYPE: PRT
<213> ORGANISM: Homosapiens
<220> FEATURE:
<223> OTHER INFORMATION: Xaa= any amino acid
<223> OTHER INFORMATION: Frame shift sequence

<400> SEQUENCE: 92

Ile Arg Ala Ser Ser Leu Trp Leu Ser Arg Gly Gln Arg Trp Ile Arg
1               5                   10                  15

Pro Ala Ala Ser Ser Asp Phe Pro Ser Gln Ser Lys Ala Ser Ala Ile
            20                  25                  30

Xaa Xaa Thr Thr Thr Thr Ala Ile Xaa His His Ala Arg Ser Xaa Ala
        35                  40                  45

Xaa Ser Ser Arg Thr Xaa Arg Ser Pro Pro Gly Arg Cys Ser Ile Xaa
    50                  55                  60

Cys Xaa Thr Pro Ser Leu Leu Gln Arg Gln Glu Asp His Met Gln Gly
65                  70                  75                  80

Pro Leu Ala Val
```

```
<210> SEQ ID NO 93
<211> LENGTH: 256
<212> TYPE: DNA
<213> ORGANISM: Homosapiens
<220> FEATURE:
<221> NAME/KEY: CDS
<222> LOCATION: (3)...(256)
<223> OTHER INFORMATION: N= A, T, C or G
      Xaa= any amino acid
<223> OTHER INFORMATION: Synthetically generated nucleic acid

<400> SEQUENCE: 93 ga tcc gcg cat cct ctc tgt ggc tct cgc ggg gtc aga ggt gga taa      47
   Ser Ala His Pro Leu Cys Gly Ser Arg Gly Val Arg Gly Gly  *
    1               5                   10 ggc cgg ccg caa gct cgg act tcc cgt cnc aat cna agg ctt ctg cga     95
Gly Arg Pro Gln Ala Arg Thr Ser Arg Xaa Asn Xaa Arg Leu Leu Arg
 15                  20                  25                  30 tcn cca nta caa cta cna cgg caa tct nac atc acg caa gat cgc ang    143
Ser Pro Xaa Gln Leu Xaa Arg Gln Ser Xaa Ile Thr Gln Asp Arg Xaa
            35                  40                  45 ctc ngt cat caa gga cgc ngc ggt cnc cnc ccg gca ggt gct cna tat    191
Leu Xaa His Gln Gly Arg Xaa Gly Xaa Xaa Pro Ala Gly Ala Xaa Tyr
        50                  55                  60
```

-continued

```
ngt gtt gaa naa cac cat cgc tcc tgc aac ggc aag aag atc aca tgc    239
Xaa Val Glu Xaa His His Arg Ser Cys Asn Gly Lys Lys Ile Thr Cys
        65                  70                  75 aag gtc cac tcg ctg tg                                             256
Lys Val His Ser Leu
    80
```

<210> SEQ ID NO 94
<211> LENGTH: 83
<212> TYPE: PRT
<213> ORGANISM: Homosapiens
<220> FEATURE:
<223> OTHER INFORMATION: Xaa= any amino acid
<223> OTHER INFORMATION: Frame shift sequence

<400> SEQUENCE: 94

Ser Ala His Pro Leu Cys Gly Ser Arg Gly Val Arg Gly Gly Gly Arg
1               5                   10                  15

Pro Gln Ala Arg Thr Ser Arg Xaa Asn Xaa Arg Leu Leu Arg Ser Pro
            20                  25                  30

Xaa Gln Leu Xaa Arg Gln Ser Xaa Ile Thr Gln Asp Arg Xaa Leu Xaa
        35                  40                  45

His Gln Gly Arg Xaa Gly Xaa Xaa Pro Ala Gly Ala Xaa Tyr Xaa Val
    50                  55                  60

Glu Xaa His His Arg Ser Cys Asn Gly Lys Lys Ile Thr Cys Lys Val
65                  70                  75                  80

His Ser Leu

<210> SEQ ID NO 95
<211> LENGTH: 256
<212> TYPE: DNA
<213> ORGANISM: Homosapiens
<220> FEATURE:
<223> OTHER INFORMATION: N= A, T, C or G
<223> OTHER INFORMATION: Sythetically generated nucleic acid
<223> OTHER INFORMATION: Reverse strand

<400> SEQUENCE: 95
cacagcgagt ggaccttgca tgtgatcttc ttgccgttgc aggagcgatg gtgttnttca     60
acacnatatn gagcacctgc cgggnggnga ccgcggcgtc cttgatgacn gagcntgcga    120
tcttgcgtga tgtnagattg ccgtngtagt tgtantggng atcgcagaag ccttngattg    180
ngacgggaag tccgagcttg cggccggcct tatccacctc tgaccccgcg agagccacag    240
agaggatgcg cggatc                                                    256

<210> SEQ ID NO 96
<211> LENGTH: 83
<212> TYPE: PRT
<213> ORGANISM: Homosapiens
<220> FEATURE:
<223> OTHER INFORMATION: Xaa= any amino acid
<223> OTHER INFORMATION: Frame shift sequence
<223> OTHER INFORMATION: Reverse strand

<400> SEQUENCE: 96

His Ser Glu Gln Thr Leu His Val Ile Phe Leu Pro Leu Gln Glu Arg
1               5                   10                  15

```
Trp Cys Xaa Ser Thr Ser Tyr Xaa Ala Pro Ala Gly Xaa Xaa Pro Xaa
            20                  25                  30

Arg Pro Xaa Ser Xaa Arg Ser Cys Val Met Xaa Asp Cys Arg Xaa Ser
            35                  40                  45

Cys Xaa Xaa Asp Arg Arg Ser Leu Xaa Leu Xaa Arg Glu Val Arg Ala
        50                  55                  60

Cys Gly Arg Pro Tyr Pro Pro Leu Thr Pro Arg Glu Pro Gln Arg Gly
65                  70                  75                  80

Cys Ala Asp

<210> SEQ ID NO 97
<211> LENGTH: 82
<212> TYPE: PRT
<213> ORGANISM: Homosapiens
<220> FEATURE:
<223> OTHER INFORMATION: Xaa= any amino acid
<223> OTHER INFORMATION: Frame shift sequence
<223> OTHER INFORMATION: Reverse strand

<400> SEQUENCE: 97

Thr Ala Ser Gly Pro Cys Met Ser Ser Cys Arg Cys Arg Ser Asp Gly
1               5                   10                  15

Val Xaa Gln His Xaa Xaa Glu His Leu Pro Xaa Xaa Asp Arg Xaa Val
            20                  25                  30

Leu Asp Asp Xaa Xaa Cys Asp Leu Ala Cys Xaa Ile Ala Xaa Val Val
            35                  40                  45

Val Xaa Xaa Ile Ala Glu Ala Xaa Asp Xaa Asp Gly Lys Ser Glu Leu
        50                  55                  60

Ala Ala Gly Leu Ile His Leu Pro Arg Glu Ser His Arg Glu Asp Ala
65                  70                  75                  80

Arg Ile

<210> SEQ ID NO 98
<211> LENGTH: 83
<212> TYPE: PRT
<213> ORGANISM: Homosapiens
<220> FEATURE:
<223> OTHER INFORMATION: Xaa= any amino acid
<223> OTHER INFORMATION: Frame shift sequence
<223> OTHER INFORMATION: Reverse strand

<400> SEQUENCE: 98

Gln Arg Val Asp Leu Ala Cys Asp Leu Leu Ala Val Ala Gly Ala Met
1               5                   10                  15

Val Xaa Phe Asn Xaa Ile Xaa Ser Thr Cys Arg Xaa Xaa Thr Xaa Ala
            20                  25                  30

Ser Leu Met Xaa Glu Xaa Ala Ile Leu Arg Asp Xaa Arg Leu Pro Xaa
            35                  40                  45

Leu Xaa Trp Xaa Ser Gln Lys Pro Xaa Ile Xaa Thr Gly Ser Pro Ser
        50                  55                  60

Leu Arg Pro Ala Leu Ser Thr Ser Asp Pro Ala Arg Ala Thr Glu Arg
65                  70                  75                  80

Met Arg Gly
```